US006392026B1

(12) United States Patent
Sim et al.

(10) Patent No.: US 6,392,026 B1
(45) Date of Patent: May 21, 2002

(54) BINDING DOMAINS FROM PLASMODIUM VIVAX AND PLASMODIUM FALCIPARUM ERYTHROCYTE BINDING PROTEINS

(75) Inventors: Kim Lee Sim, Gaithersburg, MD (US); Chetan Chitnis, Washington, DC (US); Louis H. Miller, Bethesda, MD (US); David S. Peterson, Rockville, MD (US); Xin-Zhuan Su, Rockville, MD (US); Thomas E. Wellems, Rockville, MD (US)

(73) Assignee: The United States of America as represented by the Department of Health and Human Services, Washington, DC (US)

( * ) Notice: Subject to any disclaimer, the term of this patent is extended or adjusted under 35 U.S.C. 154(b) by 0 days.

(21) Appl. No.: 09/210,288

(22) Filed: Dec. 11, 1998

Related U.S. Application Data

(62) Division of application No. 08/568,459, filed on Dec. 7, 1995, now Pat. No. 5,849,306, which is a continuation of application No. 08/119,677, filed on Sep. 10, 1993, now abandoned.

(51) Int. Cl.$^7$ .......................... C07H 21/04; A01N 43/04
(52) U.S. Cl. ......................................... 536/23.5; 514/44
(58) Field of Search ............................. 536/23.5; 514/44

(56) References Cited

U.S. PATENT DOCUMENTS 5,198,347 A   3/1993  Miller et al.
5,849,306 A   12/1998 Sim et al.

FOREIGN PATENT DOCUMENTS

WO        WO 93/18160        9/1993

OTHER PUBLICATIONS

Fang, et al., Cloning of the plasmodium vivax Duffy receptor; Mol and Biochem Parasitology; vol. 44(1), pp. 125–132; Jan. 1991.
Adams, J.H., at al., A family of erythrocyte binding protesins of malaria parasites, Proc. Natl. Acad. Sci. USA., 89:7085–7089, Aug., 1992.
Barnwell, J.W. , et al., In vitro Evaluation of the Role of the duffy Blood Group in Erythrocyte by Plasmodium Vivax, J. Exp. Med., 169:1795–1802, May 1989.
Borst, et al., Antigenic Variation in Malaria, Cell 82:1–4, Jul. 14, 1995.

Chitnis, C., et al., Identification of the Erythrocyte Binding Domains... J. Exper. Med. 180:497–506, Aug., 1994.
Dalton, J.P., et al., Blocking the receptor–mediated invasion of erythrocytes by Plasmodioum knolesi malaria with sulfated polysaccharides and glycosaminoglyans, Eur. J. Biochem., 195:789–794, 1991.
Haynes, J.D., et al., Receptor–Like Specificity of a Plasmodium Knowlesi Malaria Protein the Binds to Duffy Antigen Ligands on Erythrocytges, J. Expl. Med., 167:1873–1881, Jun. 1988.
Holt, E.H., et al., Erythrocyte Invasion by two Plasmodium Falciparum Isolates Differing in Sialic Acid Dependency in the Presence of Glycophorin A Antibodies, Am. J. Trop. Med. Hyg., 40(3): 245–251, Mar., 1989.
Miller, L.H., et al., Identification of Plasmodium knowlesi erythrocyte binding proteins, Molecular and Biochemical Parasitology, 31:217–222, 1988.
Orlandi, P.A., et al., Characterization of the 175–kilodalton erythrocyte binding antigen of Plasmodium falciparum, Molecular and Biochemical Parasitology, 40:285–294, 1990.
Perkins, M.E., et al., Sialic Acid–Dependent Binding of Plasmodium falciparum Merozoite Surface Antigen, Pf200, to Human Erythrocytes, J. of Immunology, 141(9):3190–3196, Nov. 1, 1988.
Sim, et al., Receptor ad Ligand Domains for Invasion of Erythrocytes by Plasmodium Falciparum, Science 264:1941–1944, Jun. 24, 1994.
Sim, B.K.L., et al., Primary Structure of the 175K Plasmodium falciparum Erythrocyte Binding Antigen and Identification of a Peptide Which Elicits Antibodies that Inhibit Malaria Merozite Invasion, J. of Cell Biology, 111:1877–1884, Nov., 1990.
Su, et al., the Large Diverse gene Family var Encodes Proteins Involved in Cytoadherence and Antigenic... Cell 82:89–100, Jul. 14, 1995.
Wertheimer, S.P., et al., Plasmodium vivax Interaction with the Human Duffy Blood Group glycoprotein: Identification of a Parasite Receptor–like Protein, Experimental Parasitology, 69:340–350, 1989.

*Primary Examiner*—Mark Navarro
(74) *Attorney, Agent, or Firm*—Knobbe, Martens, Olson & Bear LLP

(57) ABSTRACT

The present invention provides isolated polypeptides useful in the treatment and prevention of malaria caused by *Plasmodium falciparum* or *P. vivax*. In particular, the polypeptides are derived from the binding domains of the proteins in the EBL family as well as the sialic acid binding protein (SABP) on *P. falciparum* merozoites. The polypeptides may also be derived from the Duffy antigen binding protein (DABP) on *P. vivax* merozoites.

18 Claims, 7 Drawing Sheets

Family 1

| | | |
|---|---|---|
| DABP | $C-X_{12}-C-X_5$---VCIPDRRYQLCMKEL-$X_{47}$- | DFCKDIRWSLGDFGDIIMGTDMEGIGYSK-$X_{11}$- |
| SABP F1 | $C-X_{10}-C-X_9$---VCIPDRRIQLCIVNL-$X_{36}$- | KFCNDLKNSFLDYGHLAMGNDMDFGGYST-$X_{17}$- |
| SABP F2 | $C-X_{13}-C-X_{10}$-VCVPPRRQELCLGNI-$X_{36}$- | EVCKIINKTFADIRDIIGGTDYWNDLSNR-$X_{15}$- |
| EBL-e1 | $C-X_{12}-C-X_{11}$-VCGPPRRQQLCLGYI-$X_{36}$- | KICNAILGSYADIGDIVRGLDVWRDINTN-$X_{17}$- |

Family 2

| | | |
|---|---|---|
| EBL-e2 | ---------ACAPYRRLHLCDYNL-$X_{43}$- | QLCTVLARSFADIGDIVRGKDLYLGYDNK-$X_{37}$- |
| Proj3 F1 | $C-X_{15}-C-X_{15}$-ACAPYRRLHVCDQNL-$X_{45}$- | QICTMLARSFADIGDIVRGRDLYLGNPQE-$X_{30}$- |
| Proj3 F2 | $C-X_{17}-C-X_{31}$-VFLPPRREHMCTSNL-$X_{55}$- | AMCRAVRYSFADLGDIIRGRDMWDEDKSS-$X_{32}$- |
| Proj3 F3 | $C-X_{10}-C-X_{10}$-ACMPPRRQKLCLYYI-$X_{52}$- | QFLRSMMYTFGDYRDICLNTDISKKQNDV-$X_{15}$- |
| E31a | $C-X_{10}-C-X_{11}$-ACIPPRRQKLCLHYL-$X_{51}$- | DFKRQMFYTFADYRDICLGTDISSKKDTS-$X_{15}$- |

Family 1 Cont'd

| | |
|---|---|
| DABP | TDEKAQQRRKQWWNESKAQIWTAMMYSV-$X_{11}$-$C$-$X_8$---ePQIYRWIREWGRDYVSELPTEVQKLKEKC--$X_{11}$---$C$-$X_1$-- |
| SABP F1 | SEHKIKNFRKEWWNEFREKLWEAMLSEH-$X_6$---$C$-$X_6$---eLQITOWIKEWHGEELLERDNRSKLPKSKC--$X_8$---$C$-$X_0$-- |
| SABP F2 | NKKNDKLFRDEWWKVIKKDVWNVISWVF-$X_5$---$C$-$X_7$---IPQFFRWFSEWGDDYCQDKTKMIETLLVEC--$X_4$---$C$-$X_1$-- |
| EBL-e1 | KKQNDNNERNKWWEKQRNLIWSSMVKHI-$X_5$---$C$-$X_8$---IPQFLRWLKEWGDEFCEEMGTEVKQLEKIC--$X_4$---$C$-$X_1$-- |

FIG. 1B

Family 2 Cont'd

| | | | |
|---|---|---|---|
| EBL-e2 | KGGDFFQLREDWTSNRETVWKALICHA-$X_{11}$ | -C-$X_{23}$ -VPQYLRWFEEWAEDF | CRKKKKLENLQKQC--$X_6$ ---C-$X_{15}$-- |
| Proj3 F1 | NDPEFFKLREDWTANRETVWKAITCNA-$X_9$ | -C-$X_{23}$ -VPQYLRWFEEWAEDF | CRKKNKKIKDVKRNC--$X_{12}$ ---C-$X_{22}$-- |
| Proj3 F2 | KKPAYKKLRADWWEANRHQVWRAMKCAT-$X_4$ | -C-$X_8$ ---IPQRLRWMTEWAEWYCKAQSQEYDKLKKIC--$X_{11}$ ---C-$X_6$-- |
| Proj3 F3 | SKSPSGLSRQEWWKTNGPEIWKGMLCAL-$X_{37}$ | -------KPQFLRWMIEWGEEFCAERQKKENIIKDAC--$X_8$ ---C-$X_3$-- |
| E31a | KISNSIRYRKSWWETNGPVIWEGMLCAL-$X_{42}$ | -------RPQFLRWLTEWGENFCKEQKKEYKVLLAKC--$X_{11}$ ---C-$X_3$-- |

Family 1 Cont'd

| | | |
|---|---|---|
| DABP | VPPCQNACKSYDQ | WITRKKN-$X_{56}$ ----------CX---C |
| SABP F1 | EKECIDPCMKYRD | WIIRSKF-$X_{41}$-C-$X_7$ ----CX---C |
| SABP F2 | DDNCKSKCNSYKE | WISKKKK-$X_{36}$-C-$X_{20}$ ----CXX---C |
| EBL-e1 | EKKCKNACSSYEK | WIKERKN-$X_{38}$-C-$X_{19}$ ----CXX---C |

Family 2 Cont'd

| | | |
|---|---|---|
| EBL-e2 | CTNCSVWCRMYET | WIDNQKK-$X_{68}$-C-$X_{30}$ ----CXX---C |
| Proj3 F1 | CISCLYACNPYVD | WIDNQKK-$X_{69}$-C-$X_{40}$ ----CXX---C |
| Proj3 F2 | CGKCKAACDKYKEEIEKWNEQWRK-$X_{73}$-C-$X_6$-C-$X_{30}$ ----CXX---C |
| Proj3 F3 | KHRCNQACRAYQE | YVENKKK-$X_{43}$-C-$X_4$ ----CX---C |
| E31a | CVACKDQCKQYHS | WIGIWID-$X_{42}$-C-$X_8$ ----CXXXC |

Concensus amino acid sequences and the synthetic oligonucleotide primers designed from them.

I. UNIEBP5 and 5A: PRRQK/ELC  (SEQ ID NO: 22)

UNIEBP5, for A+T biased condon usage:
CC(A/G)-AG(G/A)-AG(G/A)-CAA-(G/A)AA-(C/T)TA-TG  (SEQ ID NO: 23)

UNIEBP5A, for G+C biased codon usage:
CC(C/G)-(C/A)G(C/G)-(C/A)G(C/G)-CAG-CAG-(C/T)T(C/G)-TG  (SEQ ID NO: 24)

II. UNIEBP5 B and C:  FADI/YG/RDI  (SEQ ID NO: 25)

UNIEBP5B, for A+T biased codon usage:
TTT-GC(A/T)-GAT-(A/T)(A/T)-(G/C)G(A/T)-GAT-AT  (SEQ ID NO: 26)

UNIEBP5C, for G+C biased codon usage:
TTC-GC(G/C)-GAT-(A/T)(A/T)C-(G/C)G(G/C)-GAC-AT  (SEQ ID NO: 27)

FIG. 3B

III. UNIEBP3 and 3A: PQFL/FRW (SEQ ID NO: 28)

UNIEBP3, for A+T biased codon usage:
CCA-(A/T)C(T/G)-(T/G)A(A/G)-(A/G)AA-TTG-(A/T)GG (SEQ ID NO: 29)

UNIEBP3A, for G+C biased codon usage:
CCA-(C/G)C(G/T)-G(A/T)A-GA(A/T)-CTG-(C/G)GG (SEQ ID NO: 30)

IV. UNIEBP3 and C: EWGD/ED/EY/FC (SEQ ID NO: 31)

UNIEBP3B, for A+T biased codon usage:
CA-A(A/T)A-(A/T)TC-(A/T)TC-(A/T)CC-CCA-TTC (SEQ ID NO: 32)

UNIEBP3C, for G+C biased codon usage:
CA-G(A/T)A-(G/C)TC-(G/C)TC-(G/C)CC-CCA-CTC (SEQ ID NO: 33)

SEQUENCE LISTING (1) GENERAL INFORMATION:

(iii) NUMBER OF SEQUENCES: 37

(2) INFORMATION FOR SEQ ID NO:1:

(i) SEQUENCE CHARACTERISTICS:
      (A) LENGTH: 4084 base pairs
      (B) TYPE: nucleic acid
      (C) STRANDEDNESS: single
      (D) TOPOLOGY: linear (ii) MOLECULE TYPE: DNA (genomic)

(iii) HYPOTHETICAL: NO (vi) ORIGINAL SOURCE:
      (A) ORGANISM: Plasmodium vivax (xi) SEQUENCE DESCRIPTION: SEQ ID NO:1:

```
AAGCTTTTAA AAATAGCAAC AAAATTTCGA AACATTGCCA CAAAAATTTT A TGTTTTACA      60
TATATTTAGA TTCATACAAT TTAGGTGTAC CCTGTTTTTT GATATATGCG C TTAAATTTT    120
TTTTTCGCTC ATATGTTTAG TTATATGTGT AGAACAACTT GCTGAATAAA T TACGTACAC    180
TTTCTGTTCT GAATAATATT ACCACATACA TTTAATTTTA AATACTATGA A AGGAAAAAA    240
CCGCTCTTTA TTTGTTCTCC TAGTTTTATT ATTGTTACAC AAGGTATCAT A TAAGGATGA    300
TTTTTCTATC ACACTAATAA ATTATCATGA AGGAAAAAAA TATTTAATTA T ACTAAAAAG    360
AAAATTAGAA AAAGCTAATA ATCGTGATGT TTGCAATTTT TTTCTTCATT T CTCTCAGGT    420
AAATAATGTA TTATTAGAAC GAACAATTGA AACCCTTCTA GAATGCAAAA A TGAATATGT    480
GAAAGGTGAA AATGGTTATA AATTAGCTAA AGGCACCAC TGTGTTGAGG A AGATAACTT    540
AGAACGATGG TTACAAGGAA CCAATGAAAG AAGAAGTGAG GAAAATATAA A ATATAAATA    600
TGGAGTAACG GAACTAAAAA TAAAGTATGC GCAAATGAAT GGAAAAAGAA G CAGCCGCAT    660
TTTGAAGGAA TCAATTTACG GGGCGCATAA CTTTGGAGGC AACAGTTACA T GGAGGGAAA    720
AGATGGAGGA GATAAAACTG GGGAGGAAAA AGATGGAGAA CATAAAACTG A TAGTAAAAC    780
TGATAACGGG AAAGGTGCAA ACAATTTGGT AATGTTAGAT TATGAGACAT C TAGCAATGG    840
CCAGCCAGCG GGAACCCTTG ATAATGTTCT TGAATTTGTG ACTGGGCATG A GGGAAATTC    900
TCGTAAAAAT TCCTCGAATG GTGGCAATCC TTACGATATT GATCATAAGA A AACGATCTC    960
TAGTGCTATT ATAAATCATG CTTTTCTTCA AAATACTGTA ATGAAAAACT G TAATTATAA   1020
GAGAAAACGT CGGGAAAGAG ATTGGGACTG TAACACTAAG AAGGATGTTT G TATACCAGA   1080
TCGAAGATAT CAATTATGTA TGAAGGAACT TACGAATTTG GTAAATAATA C AGACACAAA   1140
TTTTCATAGG GATATAACAT TTCGAAAATT ATATTTGAAA AGGAAACTTA T TTATGATGC   1200
TGCAGTAGAG GGCGATTTAT TACTTAAGTT GAATAACTAC AGATATAACA A AGACTTTTG   1260
```

```
CAAGGATATA AGATGGAGTT TGGGAGATTT TGGAGATATA ATTATGGGAA C GGATATGGA    1320

AGGCATCGGA TATTCCAAAG TAGTGGAAAA TAATTTGCGC AGCATCTTTG G AACTGATGA    1380

AAAGGCCCAA CAGCGTCGTA ACAGTGGTG GAATGAATCT AAAGCACAAA T TTGGACAGC    1440

AATGATGTAC TCAGTTAAAA AAAGATTAAA GGGGAATTTT TATGGATTT G TAAATTAAA    1500

TGTTGCGGTA AATATAGAAC CGCAGATATA TAGATGGATT CGAGAATGGG G AAGGGATTA    1560

CGTGTCAGAA TTGCCCACAG AAGTGCAAAA ACTGAAAGAA AAATGTGATG G AAAAATCAA    1620

TTATACTGAT AAAAAAGTAT GTAAGGTACC ACCATGTCAA AATGCGTGTA A ATCATATGA    1680

TCAATGGATA ACCAGAAAAA AAAATCAATG GGATGTTCTG TCAAATAAAT T CATAAGTGT    1740

AAAAAACGCA GAAAAGGTTC AGACGGCAGG TATCGTAACT CCTTATGATA T ACTAAAACA    1800

GGAGTTAGAT GAATTTAACG AGGTGGCTTT TGAGAATGAA ATTAACAAAC G TGATGGTGC    1860

ATATATTGAG TTATGCGTTT GTTCCGTTGA AGAGGCTAAA AAAAATACTC A GGAAGTTGT    1920

GACAAATGTG GACAATGCTG CTAAATCTCA GGCCACCAAT TCAAATCCGA T AAGTCAGCC    1980

TGTAGATAGT AGTAAAGCGG AGAAGGTTCC AGGAGATTCT ACGCATGGAA A TGTTAACAG    2040

TGGCCAAGAT AGTTCTACCA CAGGTAAAGC TGTTACGGGG GATGGTCAAA A TGGAAATCA    2100

GACACCTGCA GAAAGCGATG TACAGCGAAG TGATATTGCC GAAAGTGTAA G TGCTAAAAA    2160

TGTTGATCCG CAGAAATCTG TAAGTAAAAG AAGTGACGAC ACTGCAAGCG T TACAGGTAT    2220

TGCCGAAGCT GGAAAGGAAA ACTTAGGCGC ATCAAATAGT CGACCTTCTG A GTCCACCGT    2280

TGAAGCAAAT AGCCCAGGTG ATGATACTGT GAACAGTGCA TCTATACCTG T AGTGAGTGG    2340

TGAAAACCCA TTGGTAACCC CCTATAATGG TTTGAGGCAT TCGAAAGACA A TAGTGATAG    2400

CGATGGACCT GCGGAATCAA TGGCGAATCC TGATTCAAAT AGTAAAGGTG A GACGGGAAA    2460

GGGGCAAGAT AATGATATGG CGAAGGCTAC TAAAGATAGT AGTAATAGTT C AGATGGTAC    2520

CAGCTCTGCT ACGGGTGATA CTACTGATGC AGTTGATAGG GAAATTAATA A AGGTGTTCC    2580

TGAGGATAGG GATAAAACTG TAGGAAGTAA AGATGGAGGG GGGGAAGATA A CTCTGCAAA    2640

TAAGGATGCA GCGACTGTAG TTGGTGAGGA TAGAATTCGT GAGAACAGCG C TGGTGGTAG    2700

CACTAATGAT AGATCAAAAA ATGACACGGA AAAGAACGGG GCCTCTACCC C TGACAGTAA    2760

ACAAAGTGAG GATGCAACTG CGCTAAGTAA AACCGAAAGT TTAGAATCAA C AGAAAGTGG    2820

AGATAGAACT ACTAATGATA CAACTAACAG TTTAGAAAAT AAAAATGGAG G AAAAGAAAA    2880

GGATTTACAA AAGCATGATT TTAAAAGTAA TGATACGCCG AATGAAGAAC C AAATTCTGA    2940

TCAAACTACA GATGCAGAAG GACATGACAG GGATAGCATC AAAAATGATA A AGCAGAAAG    3000

GAGAAAGCAT ATGAATAAAG ATACTTTTAC GAAAAATACA AATAGTCACC A TTTAAATAG    3060

TAATAATAAT TTGAGTAATG GAAAATTAGA TATAAAAGAA TACAAATACA G AGATGTCAA    3120

AGCAACAAGG GAAGATATTA TATTAATGTC TTCAGTACGC AAGTGCAACA A TAATATTTC    3180

TTTAGAGTAC TGTAACTCTG TAGAGGACAA AATATCATCG AATACTTGTT C TAGAGAGAA    3240

AAGTAAAAAT TTATGTTGCT CAATATCGGA TTTTTGTTTG AACTATTTTG A CGTGTATTC    3300

TTATGAGTAT CTTAGCTGCA TGAAAAAGGA ATTTGAAGAT CCATCCTACA A GTGCTTTAC    3360

GAAAGGGGGC TTTAAAGGTA TGCAGAAAAA GATGCTGAAT AGAAAAGGT G TTGAGTAAA    3420

TTAAAAAGGA ATTAATTTTA GGAATGTTAT AAACATTTTT GTACCCAAAA T TCTTTTTGC    3480

AGACAAGACT TACTTTGCCG CGGCGGGAGC GTTGCTGATA CTGCTGTTGT T AATTGCTTC    3540

AAGGAAGATG ATCAAAAATG AGTAACCAGA AAATAAAATA AATAACATA A AATAAAATA    3600
```

-continued

```
AAAACTAGAA TAACAATTAA AATAAAATAA AATGAGAAAT GCCTGTTAAT G CACAGTTAA    3660

TTCTAACGAT TCCATTTGTG AAGTTTTAAA GAGAGCACAA ATGCATAGTC A TTATGTCCA    3720

TGCATATATA CACATATATG TACGTATATA TAATAAACGC ACACTTTCTT G TTCGTACAG    3780

TTCTGAAGAA GCTACATTTA ATGAGTTTGA AGAATACTGT GATAATATTC A CAGAATCCC    3840

TCTGATGCCT AACAGTAATT CAAATTTCAA GAGCAAAATT CCATTTAAAA A GAAATGTTA    3900

CATCATTTTG CGTTTTTCTT TTTTTCTTTT TTTTTTCTTT TTTAGATATT G AACACATGC    3960

AGCCATCAAC CCCCCTGGAT TATTCATGAT GCTACTTTGG TAAGTAAAAG C AATTCTGAT    4020

TGTAGTGCTG ATGTAATTTT AGTCATTTTG CTTGCTGCAA TAAACGAGAA A ATATATCAA    4080

GCTT                                                                 4084
```

(2) INFORMATION FOR SEQ ID NO:2:

(i) SEQUENCE CHARACTERISTICS:
        (A) LENGTH: 1115 amino acids
        (B) TYPE: amino acid
        (C) STRANDEDNESS: single
        (D) TOPOLOGY: linear (ii) MOLECULE TYPE: protein (iii) HYPOTHETICAL: NO (vi) ORIGINAL SOURCE:
        (A) ORGANISM: Plasmodium vivax (xi) SEQUENCE DESCRIPTION: SEQ ID NO:2:

```
Met Lys Gly Lys Asn Arg Ser Leu Phe Val L eu Leu Val Leu Leu Leu
1               5                   10                  15

Leu His Lys Val Ser Tyr Lys Asp Asp Phe S er Ile Thr Leu Ile Asn
            20                  25                  30

Tyr His Glu Gly Lys Lys Tyr Leu Ile Ile L eu Lys Arg Lys Leu Glu
        35                  40                  45

Lys Ala Asn Asn Arg Asp Val Cys Asn Phe P he Leu His Phe Ser Gln
    50                  55                  60

Val Asn Asn Val Leu Leu Glu Arg Thr Ile G lu Thr Leu Leu Glu Cys
65                  70                  75                  80

Lys Asn Glu Tyr Val Lys Gly Glu Asn Gly T yr Lys Leu Ala Lys Gly
                85                  90                  95

His His Cys Val Glu Glu Asp Asn Leu Glu A rg Trp Leu Gln Gly Thr
            100                 105                 110

Asn Glu Arg Arg Ser Glu Glu Asn Ile Lys T yr Lys Tyr Gly Val Thr
        115                 120                 125

Glu Leu Lys Ile Lys Tyr Ala Gln Met Asn G ly Lys Arg Ser Ser Arg
    130                 135                 140

Ile Leu Lys Glu Ser Ile Tyr Gly Ala His A sn Phe Gly Gly Asn Ser
145                 150                 155                 160

Tyr Met Glu Gly Lys Asp Gly Asp Lys Thr G ly Glu Glu Lys Asp
                165                 170                 175

Gly Glu His Lys Thr Asp Ser Lys Thr Asp A sn Gly Lys Gly Ala Asn
            180                 185                 190

Asn Leu Val Met Leu Asp Tyr Glu Thr Ser S er Asn Gly Gln Pro Ala
        195                 200                 205

Gly Thr Leu Asp Asn Val Leu Glu Phe Val T hr Gly His Glu Gly Asn
    210                 215                 220

Ser Arg Lys Asn Ser Ser Asn Gly Gly Asn P ro Tyr Asp Ile Asp His
```

-continued

```
                225                 230                 235                 240
        Lys Lys Thr Ile Ser Ser Ala Ile Ile Asn His Ala Phe Leu Gln Asn
                        245                 250                 255
        Thr Val Met Lys Asn Cys Asn Tyr Lys Arg Lys Arg Arg Glu Arg Asp
                        260                 265                 270
        Trp Asp Cys Asn Thr Lys Lys Asp Val Cys Ile Pro Asp Arg Arg Tyr
                        275                 280                 285
        Gln Leu Cys Met Lys Glu Leu Thr Asn Leu Val Asn Asn Thr Asp Thr
                        290                 295                 300
        Asn Phe His Arg Asp Ile Thr Phe Arg Lys Leu Tyr Leu Lys Arg Lys
        305                 310                 315                 320
        Leu Ile Tyr Asp Ala Ala Val Glu Gly Asp Leu Leu Leu Lys Leu Asn
                        325                 330                 335
        Asn Tyr Arg Tyr Asn Lys Asp Phe Cys Lys Asp Ile Arg Trp Ser Leu
                        340                 345                 350
        Gly Asp Phe Gly Asp Ile Ile Met Gly Thr Asp Met Glu Gly Ile Gly
                        355                 360                 365
        Tyr Ser Lys Val Val Glu Asn Asn Leu Arg Ser Ile Phe Gly Thr Asp
                        370                 375                 380
        Glu Lys Ala Gln Gln Arg Arg Lys Gln Trp Trp Asn Glu Ser Lys Ala
        385                 390                 395                 400
        Gln Ile Trp Thr Ala Met Met Tyr Ser Val Lys Lys Arg Leu Lys Gly
                        405                 410                 415
        Asn Phe Ile Trp Ile Cys Lys Leu Asn Val Ala Val Asn Ile Glu Pro
                        420                 425                 430
        Gln Ile Tyr Arg Trp Ile Arg Glu Trp Gly Arg Asp Tyr Val Ser Glu
                        435                 440                 445
        Leu Pro Thr Glu Val Gln Lys Leu Lys Glu Lys Cys Asp Gly Lys Ile
                        450                 455                 460
        Asn Tyr Thr Asp Lys Lys Val Cys Lys Val Pro Pro Cys Gln Asn Ala
        465                 470                 475                 480
        Cys Lys Ser Tyr Asp Gln Trp Ile Thr Arg Lys Lys Asn Gln Trp Asp
                        485                 490                 495
        Val Leu Ser Asn Lys Phe Ile Ser Val Lys Asn Ala Glu Lys Val Gln
                        500                 505                 510
        Thr Ala Gly Ile Val Thr Pro Tyr Asp Ile Leu Lys Gln Glu Leu Asp
                        515                 520                 525
        Glu Phe Asn Glu Val Ala Phe Glu Asn Glu Ile Asn Lys Arg Asp Gly
                        530                 535                 540
        Ala Tyr Ile Glu Leu Cys Val Cys Ser Val Glu Glu Ala Lys Lys Asn
        545                 550                 555                 560
        Thr Gln Glu Val Val Thr Asn Val Asp Asn Ala Ala Lys Ser Gln Ala
                        565                 570                 575
        Thr Asn Ser Asn Pro Ile Ser Gln Pro Val Asp Ser Ser Lys Ala Glu
                        580                 585                 590
        Lys Val Pro Gly Asp Ser Thr His Gly Asn Val Asn Ser Gly Gln Asp
                        595                 600                 605
        Ser Ser Thr Thr Gly Lys Ala Val Thr Gly Asp Gly Gln Asn Gly Asn
                        610                 615                 620
        Gln Thr Pro Ala Glu Ser Asp Val Gln Arg Ser Asp Ile Ala Glu Ser
        625                 630                 635                 640
        Val Ser Ala Lys Asn Val Asp Pro Gln Lys Ser Val Ser Lys Arg Ser
                        645                 650                 655
```

-continued

Asp Asp Thr Ala Ser Val Thr Gly Ile Ala Glu Ala Gly Lys Glu Asn
        660                 665                 670

Leu Gly Ala Ser Asn Ser Arg Pro Ser Glu Ser Thr Val Glu Ala Asn
        675                 680                 685

Ser Pro Gly Asp Asp Thr Val Asn Ser Ala Ser Ile Pro Val Val Ser
        690                 695                 700

Gly Glu Asn Pro Leu Val Thr Pro Tyr Asn Gly Leu Arg His Ser Lys
705                 710                 715                 720

Asp Asn Ser Asp Ser Asp Gly Pro Ala Glu Ser Met Ala Asn Pro Asp
                725                 730                 735

Ser Asn Ser Lys Gly Glu Thr Gly Lys Gly Gln Asp Asn Asp Met Ala
        740                 745                 750

Lys Ala Thr Lys Asp Ser Ser Asn Ser Ser Asp Gly Thr Ser Ser Ala
        755                 760                 765

Thr Gly Asp Thr Thr Asp Ala Val Asp Arg Glu Ile Asn Lys Gly Val
        770                 775                 780

Pro Glu Asp Arg Asp Lys Thr Val Gly Ser Lys Asp Gly Gly Glu
785                 790                 795                 800

Asp Asn Ser Ala Asn Lys Asp Ala Ala Thr Val Val Gly Glu Asp Arg
                805                 810                 815

Ile Arg Glu Asn Ser Ala Gly Gly Ser Thr Asn Asp Arg Ser Lys Asn
                820                 825                 830

Asp Thr Glu Lys Asn Gly Ala Ser Thr Pro Asp Ser Lys Gln Ser Glu
        835                 840                 845

Asp Ala Thr Ala Leu Ser Lys Thr Glu Ser Leu Glu Ser Thr Glu Ser
        850                 855                 860

Gly Asp Arg Thr Thr Asn Asp Thr Thr Asn Ser Leu Glu Asn Lys Asn
865                 870                 875                 880

Gly Gly Lys Glu Lys Asp Leu Gln Lys His Asp Phe Lys Ser Asn Asp
                885                 890                 895

Thr Pro Asn Glu Glu Pro Asn Ser Asp Gln Thr Thr Asp Ala Glu Gly
                900                 905                 910

His Asp Arg Asp Ser Ile Lys Asn Asp Lys Ala Glu Arg Arg Lys His
        915                 920                 925

Met Asn Lys Asp Thr Phe Thr Lys Asn Thr Asn Ser His His Leu Asn
930                 935                 940

Ser Asn Asn Asn Leu Ser Asn Gly Lys Leu Asp Ile Lys Glu Tyr Lys
945                 950                 955                 960

Tyr Arg Asp Val Lys Ala Thr Arg Glu Asp Ile Ile Leu Met Ser Ser
                965                 970                 975

Val Arg Lys Cys Asn Asn Asn Ile Ser Leu Glu Tyr Cys Asn Ser Val
                980                 985                 990

Glu Asp Lys Ile Ser Ser Asn Thr Cys Ser Arg Glu Lys Ser Lys Asn
        995                 1000                1005

Leu Cys Cys Ser Ile Ser Asp Phe Cys Leu Asn Tyr Phe Asp Val Tyr
        1010                1015                1020

Ser Tyr Glu Tyr Leu Ser Cys Met Lys Lys Glu Phe Glu Asp Pro Ser
1025                1030                1035                1040

Tyr Lys Cys Phe Thr Lys Gly Gly Phe Lys Ile Asp Lys Thr Tyr Phe
                1045                1050                1055

Ala Ala Ala Gly Ala Leu Leu Ile Leu Leu Leu Ile Ala Ser Arg Lys
        1060                1065                1070

Met Ile Lys Asn Asp Ser Glu Glu Ala Thr P he Asn Glu Phe Glu Glu
            1075                1080             1085

Tyr Cys Asp Asn Ile His Arg Ile Pro Leu M et Pro Asn Asn Ile Glu
        1090            1095               1100

His Met Gln Pro Ser Thr Pro Leu Asp Tyr S er
1105                111 0                 1115

(2) INFORMATION FOR SEQ ID NO:3:

(i) SEQUENCE CHARACTERISTICS:
        (A) LENGTH: 4507 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (vi) ORIGINAL SOURCE:
        (A) ORGANISM: Plasmodium falciparum (xi) SEQUENCE DESCRIPTION: SEQ ID NO:3:

```
TATATATATA TATATATATA GATAATAACA TATAAATATA TTCAATGTGC A TACAATGAA      60
ATGTAATATT AGTATATATT TTTTTGCTTC CTTCTTTGTG TTATATTTTG C AAAAGCTAG     120
GAATGAATAT GATATAAAAG AGAATGAAAA ATTTTTAGAC GTGTATAAAG A AAAATTTAA     180
TGAATTAGAT AAAAAGAAAT ATGGAAATGT TCAAAAAACT GATAAGAAAA T ATTTACTTT     240
TATAGAAAAT AAATTAGATA TTTTAAATAA TTCAAAATTT AATAAAAGAT G AAGAGTTA      300
TGGAACTCCA GATAATATAG ATAAAAATAT GTCTTTAATA AATAAACATA A TAATGAAGA     360
AATGTTTAAC AACAATTATC AATCATTTTT ATCGACAAGT TCATTAATAA A GCAAAATAA     420
ATATGTTCCT ATTAACGCTG TACGTGTGTC TAGGATATTA AGTTTCCTGG A TTCTAGAAT     480
TAATAATGGA AGAAATACTT CATCTAATAA CGAAGTTTTA AGTAATTGTA G GGAAAAAAG    540
GAAAGGAATG AAATGGGATT GTAAAAAGAA AAATGATAGA AGCAACTATG T ATGTATTCC    600
TGATCGTAGA ATCCAATTAT GCATTGTTAA TCTTAGCATT ATTAAAACAT A TACAAAAGA    660
GACCATGAAG GATCATTTCA TTGAAGCCTC TAAAAAAGAA TCTCAACTTT T GCTTAAAAA    720
AAATGATAAC AAATATAATT CTAAATTTTG TAATGATTTG AAGAATAGTT T TTTAGATTA    780
TGGACATCTT GCTATGGGAA ATGATATGGA TTTTGGAGGT TATTCAACTA A GGCAGAAAA    840
CAAAATTCAA GAAGTTTTTA AAGGGGCTCA TGGGGAAATA AGTGAACATA A AATTAAAAA    900
TTTTAGAAAA GAATGGTGGA ATGAATTTAG AGAGAAACTT TGGGAAGCTA T GTTATCTGA    960
GCATAAAAAT AATATAAATA ATTGTAAAAA TATTCCCCAA GAAGAATTAC A AATTACTCA   1020
ATGGATAAAA GAATGGCATG GAGAATTTTT GCTTGAAAGA GATAATAGAT C AAAATTGCC   1080
AAAAAGTAAA TGTAAAAATA ATACATTATA TGAAGCATGT GAGAAGGAAT G TATTGATCC   1140
ATGTATGAAA TATAGAGATT GGATTATTAG AAGTAAATTT GAATGGCATA C GTTATCGAA   1200
AGAATATGAA ACTCAAAAAG TTCCAAAGGA AAATGCGGAA AATTATTTAA T CAAAATTTC   1260
AGAAAACAAG AATGATGCTA AAGTAAGTTT ATTATTGAAT AATTGTGATG C TGAATATTC   1320
AAAATATTGT GATTGTAAAC ATACTACTAC TCTCGTTAAA AGCGTTTTAA T GGTAACGA    1380
CAATACAATT AAGGAAAAGC GTGAACATAT TGATTTAGAT GATTTTTCTA A ATTTGGATG   1440
TGATAAAAAT TCCGTTGATA CAAACACAAA GGTGTGGGAA TGTAAAAACC C TTATATATT   1500
ATCCACTAAA GATGTATGTG TACCTCCGAG GAGGCAAGAA TTATGTCTTG G AAACATTGA   1560
```

```
TAGAATATAC GATAAAAACC TATTAATGAT AAAAGAGCAT ATTCTTGCTA T TGCAATATA     1620

TGAATCAAGA ATATTGAAAC GAAAATATAA GAATAAAGAT GATAAAGAAG T TTGTAAAAT     1680

CATAAATAAA ACTTTCGCTG ATATAAGAGA TATTATAGGA GGTACTGATT A TTGGAATGA     1740

TTTGAGCAAT AGAAAATTAG TAGGAAAAAT TAACACAAAT TCAAAATATG T TCACAGGAA     1800

TAAAAAAAAT GATAAGCTTT TTCGTGATGA GTGGTGGAAA GTTATTAAAA A AGATGTATG     1860

GAATGTGATA TCATGGGTAT TCAAGGATAA AACTGTTTGT AAAGAAGATG A TATTGAAAA     1920

TATACCACAA TTCTTCAGAT GGTTTAGTGA ATGGGGTGAT GATTATTGCC A GGATAAAAC     1980

AAAAATGATA GAGACTCTGA AGGTTGAATG CAAAGAAAAA CCTTGTGAAG A TGACAATTG     2040

TAAAAGTAAA TGTAATTCAT ATAAAGAATG GATATCAAAA AAAAAAGAAG A GTATAATAA     2100

ACAAGCCAAA CAATACCAAG AATATCAAAA AGGAAATAAT TACAAAATGT A TTCTGAATT     2160

TAAATCTATA AAACCAGAAG TTTATTTAAA GAAATACTCG GAAAAATGTT C TAACCTAAA     2220

TTTCGAAGAT GAATTTAAGG AAGAATTACA TTCAGATTAT AAAAATAAAT G TACGATGTG     2280

TCCAGAAGTA AAGGATGTAC CAATTTCTAT AATAAGAAAT AATGAACAAA C TTCGCAAGA     2340

AGCAGTTCCT GAGGAAAACA CTGAAATAGC ACACAGAACG GAAACTCCAT C TATCTCTGA     2400

AGGACCAAAA GGAAATGAAC AAAAAGAACG TGATGACGAT AGTTTGAGTA A AATAAGTGT     2460

ATCACCAGAA AATTCAAGAC CTGAAACTGA TGCTAAAGAT ACTTCTAACT T GTTAAAATT     2520

AAAAGGAGAT GTTGATATTA GTATGCCTAA AGCAGTTATT GGGAGCAGTC C TAATGATAA     2580

TATAAATGTT ACTGAACAAG GGGATAATAT TTCCGGGGTG AATTCTAAAC C TTTATCTGA     2640

TGATGTACGT CCAGATAAAA AGGAATTAGA AGATCAAAAT AGTGATGAAT C GGAAGAAAC     2700

TGTAGTAAAT CATATATCAA AAAGTCCATC TATAAATAAT GGAGATGATT C AGGCAGTGG     2760

AAGTGCAACA GTGAGTGAAT CTAGTAGTTC AAATACTGGA TTGTCTATTG A TGATGATAG     2820

AAATGGTGAT ACATTTGTTC GAACACAAGA TACAGCAAAT ACTGAAGATG T TATTAGAAA     2880

AGAAAATGCT GACAAGGATG AAGATGAAAA AGGCGCAGAT GAAGAAAGAC A TAGTACTTC     2940

TGAAAGCTTA AGTTCACCTG AAGAAAAAAT GTTAACTGAT AATGAAGGAG G AAATAGTTT     3000

AAATCATGAA GAGGTGAAAG AACATACTAG TAATTCTGAT AATGTTCAAC A GTCTGGAGG     3060

AATTGTTAAT ATGAATGTTG AGAAAGAACT AAAAGATACT TTAGAAAATC C TTCTAGTAG     3120

CTTGGATGAA GGAAAAGCAC ATGAAGAATT ATCAGAACCA AATCTAAGCA G TGACCAAGA     3180

TATGTCTAAT ACACCTGGAC CTTTGGATAA CACCAGTGAA GAAACTACAG A AAGAATTAG     3240

TAATAATGAA TATAAAGTTA ACGAGAGGGA AGATGAGAGA ACGCTTACTA A GGAATATGA     3300

AGATATTGTT TTGAAAAGTC ATATGAATAG AGAATCAGAC GATGGTGAAT T ATATGACGA     3360

AAATTCAGAC TTATCTACTG TAAATGATGA ATCAGAAGAC GCTGAAGCAA A AATGAAAGG     3420

AAATGATACA TCTGAAATGT CGCATAAATAG TAGTCAACAT ATTGAGAGTG A TCAACAGAA     3480

AAACGATATG AAAACTGTTG GTGATTTGGG AACCACACAT GTACAAAACG A AATTAGTGT     3540

TCCTGTTACA GGAGAAATTG ATGAAAAATT AAGGGAAAGT AAAGAATCAA A AATTCATAA     3600

GGCTGAAGAG GAAAGATTAA GTCATACAGA TATACATAAA ATTAATCCTG A AGATAGAAA     3660

TAGTAATACA TTCACATTTAA AAGATATAAG AAATGAGGAA AACGAAAGAC A CTTAACTAA     3720

TCAAAACATT AATATTAGTC AAGAAAGGGA TTTGCAAAAA CATGGATTCC A TACCATGAA     3780

TAATCTACAT GGAGATGGAG TTTCCGAAAG AAGTCAAATT AATCATAGTC A TCATGGAAA     3840

CAGACAAGAT CGGGGGGGAA ATTCTGGGAA TGTTTTAAAT ATGAGATCTA A TAATAATAA     3900

TTTTAATAAT ATTCCAAGTA GATATAATTT ATATGATAAA AAATTAGATT T AGATCTTTA     3960
```

-continued

```
TGAAAACAGA AATGATAGTA CAACAAAAGA ATTAATAAAG AAATTAGCAG A AATAAATAA         4020

ATGTGAGAAC GAAATTTCTG TAAAATATTG TGACCATATG ATTCATGAAG A AATCCCATT         4080

AAAAACATGC ACTAAAGAAA AAACAAGAAA TCTGTGTTGT GCAGTATCAG A TTACTGTAT         4140

GAGCTATTTT ACATATGATT CAGAGGAATA TTATAATTGT ACGAAAAGGG A ATTTGATGA         4200

TCCATCTTAT ACATGTTTCA GAAGGAGGC TTTTTCAAGT ATGATATTCA A ATTTTTAAT          4260

AACAAATAAA ATATATTATT ATTTTTATAC TTACAAAACT GCAAAAGTAA C AATAAAAAA         4320

AATTAATTTC TCATTAATTT TTTTTTTCTT TTTTTCTTTT TAGGTATGCC A TATTATGCA         4380

GGAGCAGGTG TGTTATTTAT TATATTGGTT ATTTTAGGTG CTTCACAAGC C AAATATCAA         4440

AGGTTAGAAA AATAAATAA AATAAAAATT GAGAAGAATG TAAATTAAAT A TAGAATTCG          4500

AGCTCGG                                                                    4507
```

(2) INFORMATION FOR SEQ ID NO:4:

(i) SEQUENCE CHARACTERISTICS:
        (A) LENGTH: 1435 amino acids
        (B) TYPE: amino acid
        (C) STRANDEDNESS: single
        (D) TOPOLOGY: linear (ii) MOLECULE TYPE: protein (iii) HYPOTHETICAL: NO (vi) ORIGINAL SOURCE:
        (A) ORGANISM: Plasmodium falciparum (xi) SEQUENCE DESCRIPTION: SEQ ID NO:4:

```
Met Lys Cys Asn Ile Ser Ile Tyr Phe Phe A la Ser Phe Val Leu
 1               5                  10                  15

Tyr Phe Ala Lys Ala Arg Asn Glu Tyr Asp I le Lys Glu Asn Glu Lys
            20                  25                  30

Phe Leu Asp Val Tyr Lys Glu Lys Phe Asn G lu Leu Asp Lys Lys Lys
        35                  40                      45

Tyr Gly Asn Val Gln Lys Thr Asp Lys Lys I le Phe Thr Phe Ile Glu
    50                  55                  60

Asn Lys Leu Asp Ile Leu Asn Asn Ser Lys P he Asn Lys Arg Trp Lys
65                  70                  75                  80

Ser Tyr Gly Thr Pro Asp Asn Ile Asp Lys A sn Met Ser Leu Ile Asn
                85                  90                  95

Lys His Asn Asn Glu Glu Met Phe Asn Asn A sn Tyr Gln Ser Phe Leu
            100                 105                 110

Ser Thr Ser Ser Leu Ile Lys Gln Asn Lys T yr Val Pro Ile Asn Ala
        115                 120                 125

Val Arg Val Ser Arg Ile Leu Ser Phe Leu A sp Ser Arg Ile Asn Asn
    130                 135                 140

Gly Arg Asn Thr Ser Ser Asn Asn Glu Val L eu Ser Asn Cys Arg Glu
145                 150                 155                 160

Lys Arg Lys Gly Met Lys Trp Asp Cys Lys L ys Lys Asn Asp Arg Ser
                165                 170                 175

Asn Tyr Val Cys Ile Pro Asp Arg Arg Ile G ln Leu Cys Ile Val Asn
            180                 185                 190

Leu Ser Ile Ile Lys Thr Tyr Thr Lys Glu T hr Met Lys Asp His Phe
        195                 200                 205

Ile Glu Ala Ser Lys Lys Glu Ser Gln Leu L eu Leu Lys Lys Asn Asp
```

-continued

```
            210                 215                 220
Asn Lys Tyr Asn Ser Lys Phe Cys Asn Asp Leu Lys Asn Ser Phe Leu
225                 230                 235                 240
Asp Tyr Gly His Leu Ala Met Gly Asn Asp Met Asp Phe Gly Gly Tyr
                245                 250                 255
Ser Thr Lys Ala Glu Asn Lys Ile Gln Glu Val Phe Lys Gly Ala His
                260                 265                 270
Gly Glu Ile Ser Glu His Lys Ile Lys Asn Phe Arg Lys Glu Trp Trp
                275                 280                 285
Asn Glu Phe Arg Glu Lys Leu Trp Glu Ala Met Leu Ser Glu His Lys
290                 295                 300
Asn Asn Ile Asn Cys Lys Asn Ile Pro Gln Glu Glu Leu Gln Ile
305                 310                 315                 320
Thr Gln Trp Ile Lys Glu Trp His Gly Glu Phe Leu Leu Glu Arg Asp
                325                 330                 335
Asn Arg Ser Lys Leu Pro Lys Ser Lys Cys Lys Asn Asn Thr Leu Tyr
                340                 345                 350
Glu Ala Cys Glu Lys Glu Cys Ile Asp Pro Cys Met Lys Tyr Arg Asp
                355                 360                 365
Trp Ile Ile Arg Ser Lys Phe Glu Trp His Thr Leu Ser Lys Glu Tyr
370                 375                 380
Glu Thr Gln Lys Val Pro Lys Glu Asn Ala Glu Asn Tyr Leu Ile Lys
385                 390                 395                 400
Ile Ser Glu Asn Lys Asn Asp Ala Lys Val Ser Leu Leu Leu Asn Asn
                405                 410                 415
Cys Asp Ala Glu Tyr Ser Lys Tyr Cys Asp Cys Lys His Thr Thr Thr
                420                 425                 430
Leu Val Lys Ser Val Leu Asn Gly Asn Asp Asn Thr Ile Lys Glu Lys
                435                 440                 445
Arg Glu His Ile Asp Leu Asp Asp Phe Ser Lys Phe Gly Cys Asp Lys
                450                 455                 460
Asn Ser Val Asp Thr Asn Thr Lys Val Trp Glu Cys Lys Asn Pro Tyr
465                 470                 475                 480
Ile Leu Ser Thr Lys Asp Val Cys Val Pro Pro Arg Arg Gln Glu Leu
                485                 490                 495
Cys Leu Gly Asn Ile Asp Arg Ile Tyr Asp Lys Asn Leu Leu Met Ile
                500                 505                 510
Lys Glu His Ile Leu Ala Ile Ala Ile Tyr Glu Ser Arg Ile Leu Lys
                515                 520                 525
Arg Lys Tyr Lys Asn Lys Asp Asp Lys Glu Val Cys Lys Ile Ile Asn
                530                 535                 540
Lys Thr Phe Ala Asp Ile Arg Asp Ile Ile Gly Gly Thr Asp Tyr Trp
545                 550                 555                 560
Asn Asp Leu Ser Asn Arg Lys Leu Val Gly Lys Ile Asn Thr Asn Ser
                565                 570                 575
Lys Tyr Val His Arg Asn Lys Lys Asn Asp Lys Leu Phe Arg Asp Glu
                580                 585                 590
Trp Trp Lys Val Ile Lys Lys Asp Val Trp Asn Val Ile Ser Trp Val
                595                 600                 605
Phe Lys Asp Lys Thr Val Cys Lys Glu Asp Asp Ile Glu Asn Ile Pro
                610                 615                 620
Gln Phe Phe Arg Trp Phe Ser Glu Trp Gly Asp Asp Tyr Cys Gln Asp
625                 630                 635                 640
```

-continued

```
Lys Thr Lys Met Ile Glu Thr Leu Lys Val Glu Cys Lys Glu Lys Pro
            645                 650                 655
Cys Glu Asp Asp Asn Cys Lys Ser Lys Cys Asn Ser Tyr Lys Glu Trp
            660                 665                 670
Ile Ser Lys Lys Lys Glu Glu Tyr Asn Lys Gln Ala Lys Gln Tyr Gln
            675                 680                 685
Glu Tyr Gln Lys Gly Asn Asn Tyr Lys Met Tyr Ser Glu Phe Lys Ser
            690                 695                 700
Ile Lys Pro Glu Val Tyr Leu Lys Lys Tyr Ser Glu Lys Cys Ser Asn
705                 710                 715                 720
Leu Asn Phe Glu Asp Glu Phe Lys Glu Glu Leu His Ser Asp Tyr Lys
            725                 730                 735
Asn Lys Cys Thr Met Cys Pro Glu Val Lys Asp Val Pro Ile Ser Ile
            740                 745                 750
Ile Arg Asn Asn Glu Gln Thr Ser Gln Glu Ala Val Pro Glu Glu Asn
            755                 760                 765
Thr Glu Ile Ala His Arg Thr Glu Thr Pro Ser Ile Ser Glu Gly Pro
            770                 775                 780
Lys Gly Asn Glu Gln Lys Glu Arg Asp Asp Ser Leu Ser Lys Ile
785                 790                 795                 800
Ser Val Ser Pro Glu Asn Ser Arg Pro Glu Thr Asp Ala Lys Asp Thr
            805                 810                 815
Ser Asn Leu Leu Lys Leu Lys Gly Asp Val Asp Ile Ser Met Pro Lys
            820                 825                 830
Ala Val Ile Gly Ser Ser Pro Asn Asp Asn Ile Asn Val Thr Glu Gln
            835                 840                 845
Gly Asp Asn Ile Ser Gly Val Asn Ser Lys Pro Leu Ser Asp Asp Val
850                 855                 860
Arg Pro Asp Lys Lys Glu Leu Glu Asp Gln Asn Ser Asp Glu Ser Glu
865                 870                 875                 880
Glu Thr Val Val Asn His Ile Ser Lys Ser Pro Ser Ile Asn Asn Gly
            885                 890                 895
Asp Asp Ser Gly Ser Gly Ser Ala Thr Val Ser Glu Ser Ser Ser Ser
            900                 905                 910
Asn Thr Gly Leu Ser Ile Asp Asp Arg Asn Gly Asp Thr Phe Val
            915                 920                 925
Arg Thr Gln Asp Thr Ala Asn Thr Glu Asp Val Ile Arg Lys Glu Asn
            930                 935                 940
Ala Asp Lys Asp Glu Asp Glu Lys Gly Ala Asp Glu Glu Arg His Ser
945                 950                 955                 960
Thr Ser Glu Ser Leu Ser Ser Pro Glu Glu Lys Met Leu Thr Asp Asn
            965                 970                 975
Glu Gly Gly Asn Ser Leu Asn His Glu Glu Val Lys Glu His Thr Ser
            980                 985                 990
Asn Ser Asp Asn Val Gln Gln Ser Gly Gly Ile Val Asn Met Asn Val
            995                 1000                1005
Glu Lys Glu Leu Lys Asp Thr Leu Glu Asn Pro Ser Ser Ser Leu Asp
            1010                1015                1020
Glu Gly Lys Ala His Glu Glu Leu Ser Glu Pro Asn Leu Ser Ser Asp
1025                1030                1035                1040
Gln Asp Met Ser Asn Thr Pro Gly Pro Leu Asp Asn Thr Ser Glu Glu
            1045                1050                1055
```

-continued

```
Thr Thr Glu Arg Ile Ser Asn Asn Glu Tyr Lys Val Asn Glu Arg Glu
            1060                1065                1070

Asp Glu Arg Thr Leu Thr Lys Glu Tyr Glu Asp Ile Val Leu Lys Ser
        1075                1080                1085

His Met Asn Arg Glu Ser Asp Asp Gly Glu Leu Tyr Asp Glu Asn Ser
        1090                1095                1100

Asp Leu Ser Thr Val Asn Asp Glu Ser Glu Asp Ala Glu Ala Lys Met
1105                1110                1115                1120

Lys Gly Asn Asp Thr Ser Glu Met Ser His Asn Ser Ser Gln His Ile
                1125                1130                1135

Glu Ser Asp Gln Gln Lys Asn Asp Met Lys Thr Val Gly Asp Leu Gly
            1140                1145                1150

Thr Thr His Val Gln Asn Glu Ile Ser Val Pro Val Thr Gly Glu Ile
        1155                1160                1165

Asp Glu Lys Leu Arg Glu Ser Lys Glu Ser Lys Ile His Lys Ala Glu
    1170                1175                1180

Glu Glu Arg Leu Ser His Thr Asp Ile His Lys Ile Asn Pro Glu Asp
1185                1190                1195                1200

Arg Asn Ser Asn Thr Leu His Leu Lys Asp Ile Arg Asn Glu Glu Asn
                1205                1210                1215

Glu Arg His Leu Thr Asn Gln Asn Ile Asn Ile Ser Gln Glu Arg Asp
            1220                1225                1230

Leu Gln Lys His Gly Phe His Thr Met Asn Asn Leu His Gly Asp Gly
        1235                1240                1245

Val Ser Glu Arg Ser Gln Ile Asn His Ser His His Gly Asn Arg Gln
    1250                1255                1260

Asp Arg Gly Gly Asn Ser Gly Asn Val Leu Asn Met Arg Ser Asn Asn
1265                1270                1275                1280

Asn Asn Phe Asn Asn Ile Pro Ser Arg Tyr Asn Leu Tyr Asp Lys Lys
                1285                1290                1295

Leu Asp Leu Asp Leu Tyr Glu Asn Arg Asn Asp Ser Thr Thr Lys Glu
            1300                1305                1310

Leu Ile Lys Lys Leu Ala Glu Ile Asn Lys Cys Glu Asn Glu Ile Ser
        1315                1320                1325

Val Lys Tyr Cys Asp His Met Ile His Glu Glu Ile Pro Leu Lys Thr
    1330                1335                1340

Cys Thr Lys Glu Lys Thr Arg Asn Leu Cys Cys Ala Val Ser Asp Tyr
1345                1350                1355                1360

Cys Met Ser Tyr Phe Thr Tyr Asp Ser Glu Glu Tyr Tyr Asn Cys Thr
                1365                1370                1375

Lys Arg Glu Phe Asp Asp Pro Ser Tyr Thr Cys Phe Arg Lys Glu Ala
            1380                1385                1390

Phe Ser Ser Met Ile Phe Lys Phe Leu Ile Thr Asn Lys Ile Tyr Tyr
        1395                1400                1405

Tyr Phe Tyr Thr Tyr Lys Thr Ala Lys Val Thr Ile Lys Lys Ile Asn
    1410                1415                1420

Phe Ser Leu Ile Phe Phe Phe Phe Ser Phe
1425                1430                1435
```

(2) INFORMATION FOR SEQ ID NO:5:

(i) SEQUENCE CHARACTERISTICS:
        (A) LENGTH: 2288 base pairs
        (B) TYPE: nucleic acid
        (C) STRANDEDNESS: single (D) TOPOLOGY: linear (ii) MOLECULE TYPE: DNA (genomic)

(iii) HYPOTHETICAL: NO (vi) ORIGINAL SOURCE:
  (A) ORGANISM: Plasmodium falciparum (xi) SEQUENCE DESCRIPTION: SEQ ID NO:5:

```
CACTTTATGC TTCCGGCTCG TATGTTGTGT GGAATTGTGA GCGGATAACA A TTTCACACA    60
GGAAACAGCT ATGACCATGA TTACGCCAAG CTCTAATACG ACTCACTATA G GGAAAGCTG   120
GTACGCCTGC AGGTCCGGTC CGGAATTCAA TAAAATATTT CCAGAAAGGA A TGTGCAAAT   180
TCACATATCC AATATATTCA AGGAATATAA AGAAATAAT GTAGATATCA T ATTTGGAAC    240
GTTGAATTAT GAATATAATA ATTTCTGTAA AGAAAAACCT GAATTAGTAT C TGCTGCCAA   300
GTATAATCTG AAAGCTCCAA ATGCTAAATC CCCTAGAATA TACAAATCTA A GGAGCATGA   360
AGAATCAAGT GTGTTTGGTT GCAAAACGAA AATCAGTAAA GTTAAAAAA A ATGGAATTG    420
TTATAGTAAT AATAAAGTAA CTAAACCTGA AGGTGTATGT GGACCACCAA G AAGGCAACA   480
ATTATGTCTT GGATATATAT TTTTGATTCG CGACGGTAAC GAGGAAGGAT T AAAAGATCA   540
TATTAATAAG GCAGCTAATT ATGAGGCAAT GCATTTAAAA GAGAAATATG A GAATGCTGG   600
TGGTGATAAA ATTTGCAATG CTATATTGGG AAGTTATGCA GATATTGGAG A TATTGTAAG   660
AGGTTTGGAT GTTTGGAGGG ATATAAATAC TAATAAATTA TCAGAAAAAT T CCAAAAAAT   720
TTTTATGGGT GGTGGTAATT CTAGGAAAAA ACAAAACGAT AATAATGAAC G TAATAAATG   780
GTGGGAAAAA CAAAGGAATT TAATATGGTC TAGTATGGTA AAACACATTC C AAAAGGAAA   840
AACATGTAAA CGTCATAATA ATTTTGAGAA AATTCCTCAA TTTTTGAGAT G GTTAAAAGA   900
ATGGGGTGAT GAATTTTGTG AGGAAATGGG TACGGAAGTC AAGCAATTAG A GAAAATATG   960
TGAAAATAAA AATTGTTCGG AAAAAAAATG TAAAAATGCA TGTAGTTCCT A TGAAAAATG  1020
GATAAAGGAA CGAAAAAATG AATATAATTT GCAATCAAAG AAATTTGATA G TGATAAAAA  1080
ATTAAATAAA AAAAACAATC TTTATAATAA ATTTGAGGAT TCTAAAGCTT A TTTAAGGAG  1140
TGAATCAAAA CAGTGCTCAA ATATAGAATT TAATGATGAA ACATTTACAT T TCCTAATAA  1200
ATATAAAGAG GCTTGTATGG TATGTGAAAA TCCTTCATCT TCGAAAGCTC T TAAACCTAT  1260
AAAAACGAAT GTGTTTCCTA TAGAGGAATC AAAAAAATCT GAGTTATCAA G TTTAACAGA  1320
TAAATCTAAG AATACTCCTA ATAGTTCTGG TGGGGGAAAT TATGGAGATA G ACAAATATC  1380
AAAAAGAGAC GATGTTCATC ATGATGGTCC TAAGGAAGTG AAATCCGGAG A AAAAGAGGT  1440
ACCAAAAATA GATGCAGCTG TTAAAACAGA AAATGAATTT ACCTCTAATC G AAACGATAT  1500
TGAAGGAAAG GAAAAAAGTA AAGGTGATCA TTCTTCTCCT GTTCATTCTA A AGATATAAA  1560
AAATGAGGAA CCACAAAGGG TGGTGTCTGA AAATTTACCT AAAATTGAAG A GAAAATGGA  1620
ATCTTCTGAT TCTATACCAA TTACTCATAT AGAAGCTGAA AAGGGTCAGT C TTCTAATTC  1680
TAGCGATAAT GATCCTGCAG TAGTAAGTGG TAGAGAATCT AAAGATGTAA A TCTTCATAC  1740
TTCTGAAAGG ATTAAAGAAA ATGAAGAAGG TGTGATTAAA ACAGATGATA G TTCAAAAAG  1800
TATTGAAATT CTAAAATAC CATCTGACCA AAATAATCAT AGTGATTTAT C ACAGAATGC   1860
AAATGAGGAC TCTAATCAAG GGAATAAGGA AACAATAAAT CCTCCTTCTA C AGAAAAAAA  1920
TCTCAAAGAA ATTCATTATA AAACATCTGA TTCTGATGAT CATGGTTCTA A AATTAAAAG  1980
TGAAATTGAA CCAAAGGAGT TAACGGAGGA ATCACCTCTT ACTGATAAAA A AACTGAAAG  2040
```

```
TGCAGCGATT GGTGATAAAA ATCATGAATC AGTAAAAAGC GCTGATATTT T TCAATCTGA    2100

GATTCATAAT TCTGATAATA GAGATAGAAT TGTTTCTGAA AGTGTAGTTC A GGATTCTTC    2160

AGGAAGCTCT ATGAGTACTG AATCTATACG TACTGATAAC AAGGATTTTA A AACAAGTGA    2220

GGATATTGCA CCTTCTATTA ATGGTCGGAA TTCCCGGGTC GACGAGCTCA C TAGTCGGCG    2280

GCCGCTCT                                                              2288
```

(2) INFORMATION FOR SEQ ID NO:6:

(i) SEQUENCE CHARACTERISTICS:
        (A) LENGTH: 749 amino acids
        (B) TYPE: amino acid
        (C) STRANDEDNESS: single
        (D) TOPOLOGY: linear (ii) MOLECULE TYPE: protein (iii) HYPOTHETICAL: NO (vi) ORIGINAL SOURCE:
        (A) ORGANISM: Plasmodium falciparum (xi) SEQUENCE DESCRIPTION: SEQ ID NO:6:

```
Ala Asp Asn Asn Phe Thr Gln Glu Thr Ala M et Thr Met Ile Thr Pro
1               5                   10                  15

Ser Ser Asn Thr Thr His Tyr Arg Glu Ser T rp Tyr Ala Cys Arg Ser
            20                  25                  30

Gly Pro Glu Phe Asn Lys Ile Phe Pro Glu A rg Asn Val Gln Ile His
        35                  40                  45

Ile Ser Asn Ile Phe Lys Glu Tyr Lys Glu A sn Asn Val Asp Ile Ile
50                  55                  60

Phe Gly Thr Leu Asn Tyr Glu Tyr Asn Asn P he Cys Lys Glu Lys Pro
65                  70                  75                  80

Glu Leu Val Ser Ala Ala Lys Tyr Asn Leu L ys Ala Pro Asn Ala Lys
                85                  90                  95

Ser Pro Arg Ile Tyr Lys Ser Lys Glu His G lu Glu Ser Ser Val Phe
            100                 105                 110

Gly Cys Lys Thr Lys Ile Ser Lys Val Lys L ys Lys Trp Asn Cys Tyr
        115                 120                 125

Ser Asn Asn Lys Val Thr Lys Pro Glu Gly V al Cys Gly Pro Pro Arg
130                 135                 140

Arg Gln Gln Leu Cys Leu Gly Tyr Ile Phe L eu Ile Arg Asp Gly Asn
145                 150                 155                 160

Glu Glu Gly Leu Lys Asp His Ile Asn Lys A la Ala Asn Tyr Glu Ala
                165                 170                 175

Met His Leu Lys Glu Lys Tyr Glu Asn Ala G ly Gly Asp Lys Ile Cys
            180                 185                 190

Asn Ala Ile Leu Gly Ser Tyr Ala Asp Ile G ly Asp Ile Val Arg Gly
        195                 200                 205

Leu Asp Val Trp Arg Asp Ile Asn Thr Asn L ys Leu Ser Glu Lys Phe
210                 215                 220

Gln Lys Ile Phe Met Gly Gly Asn Ser Arg Lys Lys Gln Asn Asp
225                 230                 235                 240

Asn Asn Glu Arg Asn Lys Trp Trp Glu Lys G ln Arg Asn Leu Ile Trp
                245                 250                 255

Ser Ser Met Val Lys His Ile Pro Lys Gly L ys Thr Cys Lys Arg His
            260                 265                 270
```

```
Asn Asn Phe Glu Lys Ile Pro Gln Phe Leu Arg Trp Leu Lys Glu Trp
            275                 280                 285

Gly Asp Glu Phe Cys Glu Met Gly Thr Glu Val Lys Gln Leu Glu
        290                 295                 300

Lys Ile Cys Glu Asn Lys Asn Cys Ser Glu Lys Lys Cys Lys Asn Ala
305                 310                 315                 320

Cys Ser Ser Tyr Glu Lys Trp Ile Lys Glu Arg Lys Asn Glu Tyr Asn
                325                 330                 335

Leu Gln Ser Lys Lys Phe Asp Ser Asp Lys Lys Leu Asn Lys Lys Asn
            340                 345                 350

Asn Leu Tyr Asn Lys Phe Glu Asp Ser Lys Ala Tyr Leu Arg Ser Glu
            355                 360                 365

Ser Lys Gln Cys Ser Asn Ile Glu Phe Asn Asp Glu Thr Phe Thr Phe
        370                 375                 380

Pro Asn Lys Tyr Lys Glu Ala Cys Met Val Cys Glu Asn Pro Ser Ser
385                 390                 395                 400

Ser Lys Ala Leu Lys Pro Ile Lys Thr Asn Val Phe Pro Ile Glu Glu
                405                 410                 415

Ser Lys Lys Ser Glu Leu Ser Ser Leu Thr Asp Lys Ser Lys Asn Thr
            420                 425                 430

Pro Asn Ser Ser Gly Gly Asn Tyr Gly Asp Arg Gln Ile Ser Lys
        435                 440                 445

Arg Asp Asp Val His His Asp Gly Pro Lys Glu Val Lys Ser Gly Glu
450                 455                 460

Lys Glu Val Pro Lys Ile Asp Ala Ala Val Lys Thr Glu Asn Glu Phe
465                 470                 475                 480

Thr Ser Asn Arg Asn Asp Ile Glu Gly Lys Glu Lys Ser Lys Gly Asp
                485                 490                 495

His Ser Ser Pro Val His Ser Lys Asp Ile Lys Asn Glu Glu Pro Gln
            500                 505                 510

Arg Val Val Ser Glu Asn Leu Pro Lys Ile Glu Glu Lys Met Glu Ser
            515                 520                 525

Ser Asp Ser Ile Pro Ile Thr His Ile Glu Ala Glu Lys Gly Gln Ser
        530                 535                 540

Ser Asn Ser Ser Asp Asn Asp Pro Ala Val Val Ser Gly Arg Glu Ser
545                 550                 555                 560

Lys Asp Val Asn Leu His Thr Ser Glu Arg Ile Lys Glu Asn Glu Glu
                565                 570                 575

Gly Val Ile Lys Thr Asp Asp Ser Ser Lys Ser Ile Glu Ile Ser Lys
            580                 585                 590

Ile Pro Ser Asp Gln Asn Asn His Ser Asp Leu Ser Gln Asn Ala Asn
        595                 600                 605

Glu Asp Ser Asn Gln Gly Asn Lys Glu Thr Ile Asn Pro Pro Ser Thr
        610                 615                 620

Glu Lys Asn Leu Lys Glu Ile His Tyr Lys Thr Ser Asp Ser Asp Asp
625                 630                 635                 640

His Gly Ser Lys Ile Lys Ser Glu Ile Glu Pro Lys Glu Leu Thr Glu
                645                 650                 655

Glu Ser Pro Leu Thr Asp Lys Lys Thr Glu Ser Ala Ala Ile Gly Asp
            660                 665                 670

Lys Asn His Glu Ser Val Lys Ser Ala Asp Ile Phe Gln Ser Glu Ile
            675                 680                 685

His Asn Ser Asp Asn Arg Asp Arg Ile Val Ser Glu Ser Val Val Gln
```

-continued

```
            690             695             700
Asp Ser Ser Gly Ser Ser Met Ser Thr Glu S er Ile Arg Thr Asp Asn
705             710             715                 720

Lys Asp Phe Lys Thr Ser Glu Asp Ile Ala P ro Ser Ile Asn Gly Arg
                725             730                 735

Asn Ser Arg Val Asp Glu Leu Thr Ser Arg A rg Pro Leu
            740             745
```

(2) INFORMATION FOR SEQ ID NO:7:

(i) SEQUENCE CHARACTERISTICS:
        (A) LENGTH: 2606 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (vi) ORIGINAL SOURCE:
        (A) ORGANISM: Plasmodium falciparum (xi) SEQUENCE DESCRIPTION: SEQ ID NO:7:

```
AGCTCTATTA CGACTCACTA TAGGGAAAGC TGGTACGCCT GCAGGTACCG G TCCGGAATT     60

CCCGGGTCGA CGAGCTCACT AGTCGGCGGC CGCTCTAGAG GATCCAAGCT T AATAGTGTT    120

TATACGTCTA TTGGCTTATT TTTAAATAGC TTAAAAAGCG GACCATGTAA A AAGGATAAT    180

GATAATGCAG AGGATAATAT AGATTTTGGT GATGAAGGTA AAACATTTAA A GAGGCAGAT    240

AATTGTAAAC CATGTTCTCA ATTTACTGTT GATTGTAAAA ATTGTAATGG T GGTGATACA    300

AAAGGGAAGT GCAATGGCAG CAATGGCAAA AGAATGGAA ATGATTATAT T ACTGCAAGT    360

GATATTGAAA ATGGAGGGAA TTCTATTGGA AATATAGATA TGGTTGTTAG T GATAAGGAT    420

GCAAATGGAT TTAATGGTTT AGACGCTTGT GGAAGTGCAA ATATCTTTAA A GGTATTAGA    480

AAAGAACAAT GGAAATGTGC TAAAGTATGT GGTTTAGATG TATGTGGTCT T AAAAATGGT    540

AATGGTAGTA TAGATAAAGA TCAAAACAA ATTATAATTA TTAGAGCATT G CTTAAACGT    600

TGGGTAGAAT ATTTTTTAGA AGATTATAAT AAAATTAATG CCAAAATTTC A CATTGTACG    660

AAAAAGGATA ATGAATCCAC ATGTACAAAT GATTGTCCAA ATAAATGTAC A TGTGTAGAA    720

GAGTGGATAA ATCAGAAAAG GACAGAATGG AAAAATATAA AAAACATTA C AAAACACAA    780

AATGAAAATG GTGACAATAA CATGAAATCT TTGGTTACAG ATATTTTGGG T GCCTTGCAA    840

CCCCAAAGTG ATGTTAACAA AGCTATAAAA CCTTGTAGTG GTTTAACTGC G TTCGAGAGT    900

TTTTGTGGTC TTAATGGCGC TGATAACTCA GAAAAAAAG AAGGTGAAGA T TACGATCTT    960

GTTCTATGTA TGCTTAAAAA TCTTGAAAAA CAAATTCAGG AGTGCAAAAA G AAACATGGC   1020

GAAACTAGTG TCGAAAATGG TGGCAAATCA TGTACCCCCC TTGACAACAC C ACCCTTGAG   1080

GAGGAACCCA TAGAAGAGGA AAACCAAGTG GAAGCGCCGA ACATTTGTCC A AAACAAACA   1140

GTGGAAGATA AAAAAAAGA GGAAGAAGAA GAAACTTGTA CACCGGCATC A CCAGTACCA   1200

GAAAAACCGG TACCTCATGT GGCACGTTGG CGAACATTTA CACCACCTGA G GTATTCAAG   1260

ATATGGAGGG GAAGGAGAAA TAAAACTACG TGCGAAATAG TGGCAGAAAT G CTTAAAGAT   1320

AAGAATGGAA GGACTACAGT AGGTGAATGT TATAGAAAAG AAACTTATTC T GAATGGACG   1380

TGTGATGAAA GTAAGATTAA AATGGGACAG CATGGAGCAT GTATTCCTCC A AGAAGACAA   1440

AAATTATGTT TACATTATTT AGAAAAAATA ATGCAAATA CAAATGAATT G AAATACGCA   1500
```

```
TTTATTAAAT GTGCTGCAGC AGAAACTTTT TTGTTATGGC AAAACTACAA A AAAGATAAG    1560

AATGGTAATG CAGAAGATCT CGATGAAAAA TTAAAAGGTG GTATTATCCC C GAAGATTTT    1620

AAACGGCAAA TGTTCTATAC GTTTGCAGAT TATAGAGATA TATGTTTGGG T ACGGATATA    1680

TCATCAAAAA AAGATACAAG TAAAGGTGTA GGTAAAGTAA AATGCAATAT T GATGATGTT    1740

TTTTATAAAA TTAGCAATAG TATTCGTTAC CGTAAAAGTT GGTGGGAAAC A AATGGTCCA    1800

GTTATATGGG AAGGAATGTT ATGCGCTTTA AGTTATGATA CGAGCCTAAA T AATGTTAAT    1860

CCGGAAACTC ACAAAAAACT TACCGAAGGC AATAACAACT TTGAGAAAGT C ATATTTGGT    1920

AGTGATAGTA GCACTACTTT GTCCAAATTT TCTGAAAGAC CTCAATTTCT A AGATGGTTG    1980

ACTGAATGGG GAGAAAATTT CTGCAAAGAA CAAAAAAAGG AGTATAAGGT G TTGTTGGCA    2040

AAATGTAAGG ATTGTGATGT TGATGGTGAT GGTAAATGTA ATGGAAAATG T GTTGCGTGC    2100

AAAGATCAAT GTAAACAATA TCATAGTTGG ATTGGAATAT GGATAGATAA T TATAAAAAA    2160

CAAAAAGGAA GATATACTGA GGTTAAAAAA ATACCTCTGT ATAAGAAGA T AAAGACGTG     2220

AAAAACTCAG ATGATGCTCG CGATTATTTA AAAACACAAT TACAAATAT G AAATGTGTA     2280

AATGGAACTA CTGATGAAAA TTGTGAGTAT AAGTGTATGC ATAAAACCTC A TCCACAAAT    2340

AGTGATATGC CCGAATCGTT GGACGAAAAG CCGGAAAAGG TCAAAGACAA G TGTAATTGT    2400

GTACCTAATG AATGCAATGC ATTGAGTGTA AGTGGTAGCG GTTTTCCTGA T GGTCAAGCT    2460

TACGTACGCG TGCATGCGAC GTCATAGCTC TTCTATAGTG TCACCTAAAT T CAATTCACT    2520

GGCCGTCGTT TTACAACGTC GTGACTGGGA AAACCTGGCG TTACCCAACT T AATCGCCTT    2580

GCAGCACATC CCCCTTTCGC CAGCTG                                         2606
```

(2) INFORMATION FOR SEQ ID NO:8:

(i) SEQUENCE CHARACTERISTICS:
        (A) LENGTH: 921 amino acids
        (B) TYPE: amino acid
        (C) STRANDEDNESS: single
        (D) TOPOLOGY: linear (ii) MOLECULE TYPE: protein (iii) HYPOTHETICAL: NO (vi) ORIGINAL SOURCE:
        (A) ORGANISM: Plasmodium falciparum (xi) SEQUENCE DESCRIPTION: SEQ ID NO:8:

```
Lys Leu Asn Ser Val Tyr Thr Ser Ile Gly L eu Phe Leu Asn Ser Leu
1               5                   10                  15

Lys Ser Gly Pro Cys Lys Lys Asp Asn Asp A sn Ala Glu Asp Asn Ile
            20                  25                  30

Asp Phe Gly Asp Glu Gly Lys Thr Phe Lys G lu Ala Asp Asn Cys Lys
        35                  40                  45

Pro Cys Ser Gln Phe Thr Val Asp Cys Lys A sn Cys Asn Gly Gly Asp
    50                  55                  60

Thr Lys Gly Lys Cys Asn Gly Ser Asn Gly L ys Lys Asn Gly Asn Asp
65                  70                  75                  80

Tyr Ile Thr Ala Ser Asp Ile Glu Asn Gly G ly Asn Ser Ile Gly Asn
                85                  90                  95

Ile Asp Met Val Val Ser Asp Lys Asp Ala A sn Gly Phe Asn Gly Leu
            100                 105                 110

Asp Ala Cys Gly Ser Ala Asn Ile Phe Lys G ly Ile Arg Lys Glu Gln
        115                 120                 125
```

-continued

```
Trp Lys Cys Ala Lys Val Cys Gly Leu Asp Val Cys Gly Leu Lys Asn
    130                 135                 140
Gly Asn Gly Ser Ile Asp Lys Asp Gln Lys Gln Ile Ile Ile Ile Arg
145                 150                 155                 160
Ala Leu Leu Lys Arg Trp Val Glu Tyr Phe Leu Glu Asp Tyr Asn Lys
                165                 170                 175
Ile Asn Ala Lys Ile Ser His Cys Thr Lys Lys Asp Asn Glu Ser Thr
                180                 185                 190
Cys Thr Asn Asp Cys Pro Asn Lys Cys Thr Cys Val Glu Glu Trp Ile
                195                 200                 205
Asn Gln Lys Arg Thr Glu Trp Lys Asn Ile Lys Lys His Tyr Lys Thr
    210                 215                 220
Gln Asn Glu Asn Gly Asp Asn Asn Met Lys Ser Leu Val Thr Asp Ile
225                 230                 235                 240
Leu Gly Ala Leu Gln Pro Gln Ser Asp Val Asn Lys Ala Ile Lys Pro
                245                 250                 255
Cys Ser Gly Leu Thr Ala Phe Glu Ser Phe Cys Gly Leu Asn Gly Ala
                260                 265                 270
Asp Asn Ser Glu Lys Lys Glu Gly Glu Asp Tyr Asp Leu Val Leu Cys
                275                 280                 285
Met Leu Lys Asn Leu Glu Lys Gln Ile Gln Glu Cys Lys Lys Lys His
    290                 295                 300
Gly Glu Thr Ser Val Glu Asn Gly Gly Lys Ser Cys Thr Pro Leu Asp
305                 310                 315                 320
Asn Thr Thr Leu Glu Glu Glu Pro Ile Glu Glu Glu Asn Gln Val Glu
                325                 330                 335
Ala Pro Asn Ile Cys Pro Lys Gln Thr Val Glu Asp Lys Lys Lys Glu
                340                 345                 350
Glu Glu Glu Glu Thr Cys Thr Pro Ala Ser Pro Val Pro Glu Lys Pro
                355                 360                 365
Val Pro His Val Ala Arg Trp Arg Thr Phe Thr Pro Pro Glu Val Phe
    370                 375                 380
Lys Ile Trp Arg Gly Arg Arg Asn Lys Thr Thr Cys Glu Ile Val Ala
385                 390                 395                 400
Glu Met Leu Lys Asp Lys Asn Gly Arg Thr Thr Val Gly Glu Cys Tyr
                405                 410                 415
Arg Lys Glu Thr Tyr Ser Glu Trp Thr Cys Asp Glu Ser Lys Ile Lys
                420                 425                 430
Met Gly Gln His Gly Ala Cys Ile Pro Pro Arg Arg Gln Lys Leu Cys
    435                 440                 445
Leu His Tyr Leu Glu Lys Ile Met Thr Asn Thr Asn Glu Leu Lys Tyr
    450                 455                 460
Ala Phe Ile Lys Cys Ala Ala Ala Glu Thr Phe Leu Leu Trp Gln Asn
465                 470                 475                 480
Tyr Lys Lys Asp Lys Asn Gly Asn Ala Glu Asp Leu Asp Glu Lys Leu
                485                 490                 495
Lys Gly Gly Ile Ile Pro Glu Asp Phe Lys Arg Gln Met Phe Tyr Thr
                500                 505                 510
Phe Ala Asp Tyr Arg Asp Ile Cys Leu Gly Thr Asp Ile Ser Ser Lys
                515                 520                 525
Lys Asp Thr Ser Lys Gly Val Gly Lys Val Lys Cys Asn Ile Asp Asp
530                 535                 540
```

-continued

```
Val Phe Tyr Lys Ile Ser Asn Ser Ile Arg Tyr Arg Lys Ser Trp Trp
545                 550                 555                 560

Glu Thr Asn Gly Pro Val Ile Trp Glu Gly Met Leu Cys Ala Leu Ser
            565                 570                 575

Tyr Asp Thr Ser Leu Asn Asn Val Asn Pro Glu Thr His Lys Lys Leu
        580                 585                 590

Thr Glu Gly Asn Asn Asn Phe Glu Lys Val Ile Phe Gly Ser Asp Ser
    595                 600                 605

Ser Thr Thr Leu Ser Lys Phe Ser Glu Arg Pro Gln Phe Leu Arg Trp
610                 615                 620

Leu Thr Glu Trp Gly Glu Asn Phe Cys Lys Glu Gln Lys Lys Glu Tyr
625                 630                 635                 640

Lys Val Leu Leu Ala Lys Cys Lys Asp Cys Asp Val Asp Gly Asp Gly
            645                 650                 655

Lys Cys Asn Gly Lys Cys Val Ala Cys Lys Asp Gln Cys Lys Gln Tyr
            660                 665                 670

His Ser Trp Ile Gly Ile Trp Ile Asp Asn Tyr Lys Lys Gln Lys Gly
        675                 680                 685

Arg Tyr Thr Glu Val Lys Lys Ile Pro Leu Tyr Lys Glu Asp Lys Asp
    690                 695                 700

Val Lys Asn Ser Asp Asp Ala Arg Asp Tyr Leu Lys Thr Gln Leu Gln
705                 710                 715                 720

Asn Met Lys Cys Val Asn Gly Thr Thr Asp Glu Asn Cys Glu Tyr Lys
            725                 730                 735

Cys Met His Lys Thr Ser Ser Thr Asn Ser Asp Met Pro Glu Ser Leu
            740                 745                 750

Asp Glu Lys Pro Glu Lys Val Lys Asp Lys Cys Asn Cys Val Pro Asn
        755                 760                 765

Glu Cys Asn Ala Leu Ser Val Ser Gly Ser Gly Phe Pro Asp Gly Gln
    770                 775                 780

Ala Phe Gly Gly Gly Val Leu Glu Gly Thr Cys Lys Gly Leu Gly Glu
785                 790                 795                 800

Pro Lys Lys Lys Ile Glu Pro Pro Gln Tyr Asp Pro Thr Asn Asp Ile
            805                 810                 815

Leu Lys Ser Thr Ile Pro Val Thr Ile Val Leu Ala Leu Gly Ser Ile
            820                 825                 830

Ala Phe Leu Phe Met Lys Val Ile Tyr Ile Tyr Val Trp Tyr Ile Tyr
        835                 840                 845

Met Leu Cys Val Gly Ala Leu Asp Thr Tyr Ile Cys Gly Cys Ile Cys
850                 855                 860

Ile Cys Ile Phe Ile Cys Val Ser Val Tyr Val Cys Val Tyr Val Tyr
865                 870                 875                 880

Val Phe Leu Tyr Met Cys Val Phe Tyr Ile Tyr Phe Ile Tyr Ile Tyr
            885                 890                 895

Val Phe Ile Leu Lys Met Lys Lys Met Lys Lys Met Lys Lys Met Lys
            900                 905                 910

Lys Met Lys Lys Arg Lys Lys Arg Ile
915                 920
```

(2) INFORMATION FOR SEQ ID NO:9:

(i) SEQUENCE CHARACTERISTICS:
        (A) LENGTH: 2101 base pairs
        (B) TYPE: nucleic acid
        (C) STRANDEDNESS: single (D) TOPOLOGY: linear (ii) MOLECULE TYPE: DNA (genomic)

(iii) HYPOTHETICAL: NO (vi) ORIGINAL SOURCE:
         (A) ORGANISM: Plasmodium falciparum (xi) SEQUENCE DESCRIPTION: SEQ ID NO:9:

```
GGAACAGGGT GATAATAAAG TAGGAGCCTG TGCTCCGTAT AGACGATTAC A TTTATGTGA      60
TTATAATTTG GAATCTATAG ACACAACGTC GACGACGCAT AAGTTGTTGT T AGAGGTGTG     120
TATGGCAGCA AAATACGAAG GAAACTCAAT AAATACACAT TATACACAAC A TCAACGAAC     180
TAATGAGGAT TCTGCTTCCC AATTATGTAC TGTATTAGCA CGAAGTTTTG C AGATATAGG     240
TGATATCGTA AGAGGAAAAG ATCTATATCT CGGTTATGAT AATAAAGAAA A AGAACAAAG     300
AAAAAAATTA GAACAGAAAT TGAAAGATAT TTTCAAGAAA ATACATAAGG A CGTGATGAA     360
GACGAATGGC GCACAAGAAC GCTACATAGA TGATGCCAAA GGAGGAGATT T TTTTCAATT     420
AAGAGAAGAT TGGTGGACGT CGAATCGAGA AACAGTATGG AAAGCATTAA T ATGTCATGC     480
ACCAAAAGAA GCTAATTATT TTATAAAAAC AGCGTGTAAT GTAGGAAAAG G AACTAATGG     540
TCAATGCCAT TGCATTGGTG GAGATGTTCC CACATATTTC GATTATGTGC C GCAGTATCT     600
TCGCTGGTTC GAGGAATGGG CAGAAGACTT TTGCAGGAAA AAAAAAAAAA A ACTAGAAAA     660
TTTGCAAAAA CAGTGTCGTG ATTACGAACA AAATTTATAT TGTAGTGGTA A TGGCTACGA     720
TTGCACAAAA ACTATATATA AAAAGGTAA ACTTGTTATA GGTGAACATT G TACAAACTG     780
TTCTGTTTGG TGTCGTATGT ATGAAACTTG GATAGATAAC CAGAAAAAAG A ATTTCTAAA     840
ACAAAAAAGA AAATACGAAA CAGAAATATC AGGTGGTGGT AGTGGTAAGA G TCCTAAAAG     900
GACAAAACGG GCTGCACGTA GTAGTAGTAG TAGTGATGAT AATGGGTATG A AAGTAAATT     960
TTATAAAAAA CTGAAAGAAG TTGGCTACCA AGATGTCGAT AAATTTTTAA A AATATTAAA    1020
CAAAGAAGGA ATATGTCAAA AACAACCTCA GTAGGAAAT GAAAAAGCAG A TAATGTTGA    1080
TTTTACTAAT GAAAAATATG TAAAAACATT TTCTCGTACA GAAATTTGTG A ACCGTGCCC    1140
ATGGTGTGGA TTGGAAAAAG GTGGTCCACC ATGGAAAGTT AAAGGTGACA A AACCTGCGG    1200
AAGTGCAAAA ACAAAGACAT ACGATCCTAA AAATATTACC GATATACCAG T ACTCTACCC    1260
TGATAAATCA CAGCAAAATA TACTAAAAAA ATATAAAAAT TTTTGTGAAA A AGGTGCACC    1320
TGGTGGTGGT CAAATTAAAA AATGGCAATG TTATTATGAT GAACATAGGC C TAGTAGTAA    1380
AAATAATAAT AATTGTGTAG AAGGAACATG GGACAAGTTT ACACAAGGTA A ACAAACCGT    1440
TAAGTCCTAT AATGTTTTTT TTTGGGATTG GGTTCATGAT ATGTTACACG A TTCTGTAGA    1500
GTGGAAGACA GAACTTAGTA AGTGTATAAA TAATAACACT AATGGCAACA C ATGTAGAAA    1560
CAATAATAAA TGTAAAACAG ATTGTGGTTG TTTTCAAAAA TGGGTTGAAA A AAAACAACA    1620
AGAATGGATG GCAATAAAAG ACCATTTTGG AAAGCAAACA GATATTGTCC A ACAAAAAGG    1680
TCTTATCGTA TTTAGTCCCT ATGGAGTTCT TGACCTTGTT TTGAAGGGCG G TAATCTGTT    1740
GCAAAATATT AAAGATGTTC ATGGAGATAC AGATGACATA AAACACATTA A GAAACTGTT    1800
GGATGAGGAA GACGCAGTAG CAGTTGTTCT TGGTGGCAAG GACAATACCA C AATTGATAA    1860
ATTACTACAA CACGAAAAAG AACAAGCAGA ACAATGCAAA CAAAAGCAGG A AGAATGCGA    1920
GAAAAAGCA CAACAAGAAA GTCGTGGTCG CTCCGCCGAA ACCGCGAAG A CGAAAGGAC    1980
ACAACAACCT GCTGATAGTG CCGGCGAAGT CGAAGAAGAA GAAGACGACG A CGACTACGA    2040
```

```
CGAAGACGAC GAAGATGACG ACGTAGTCCA GGACGTAGAT GTAAGTGAAA T AAGAGGTCC       2100
G                                                                      2101
```

(2) INFORMATION FOR SEQ ID NO:10:

(i) SEQUENCE CHARACTERISTICS:
        (A) LENGTH: 700 amino acids
        (B) TYPE: amino acid
        (C) STRANDEDNESS: single
        (D) TOPOLOGY: linear (ii) MOLECULE TYPE: protein (iii) HYPOTHETICAL: NO (vi) ORIGINAL SOURCE:
        (A) ORGANISM: Plasmodium falciparum (xi) SEQUENCE DESCRIPTION: SEQ ID NO:10:

```
Glu Gln Gly Asp Asn Lys Val Gly Ala Cys A la Pro Tyr Arg Arg Leu
1               5                   10                  15

His Leu Cys Asp Tyr Asn Leu Glu Ser Ile A sp Thr Thr Ser Thr Thr
            20                  25                  30

His Lys Leu Leu Leu Glu Val Cys Met Ala A la Lys Tyr Glu Gly Asn
        35                  40                  45

Ser Ile Asn Thr His Tyr Thr Gln His Gln A rg Thr Asn Glu Asp Ser
50                  55                  60

Ala Ser Gln Leu Cys Thr Val Leu Ala Arg S er Phe Ala Asp Ile Gly
65                  70                  75                  80

Asp Ile Val Arg Gly Lys Asp Leu Tyr Leu G ly Tyr Asp Asn Lys Glu
                85                  90                  95

Lys Glu Gln Arg Lys Lys Leu Glu Gln Lys L eu Lys Asp Ile Phe Lys
            100                 105                 110

Lys Ile His Lys Asp Val Met Lys Thr Asn G ly Ala Gln Glu Arg Tyr
        115                 120                 125

Ile Asp Asp Ala Lys Gly Gly Asp Phe Phe G ln Leu Arg Glu Asp Trp
130                 135                 140

Trp Thr Ser Asn Arg Glu Thr Val Trp Lys A la Leu Ile Cys His Ala
145                 150                 155                 160

Pro Lys Glu Ala Asn Tyr Phe Ile Lys Thr A la Cys Asn Val Gly Lys
                165                 170                 175

Gly Thr Asn Gly Gln Cys His Cys Ile Gly G ly Asp Val Pro Thr Tyr
            180                 185                 190

Phe Asp Tyr Val Pro Gln Tyr Leu Arg Trp P he Glu Glu Trp Ala Glu
        195                 200                 205

Asp Phe Cys Arg Lys Lys Lys Lys Leu G lu Asn Leu Gln Lys Gln
210                 215                 220

Cys Arg Asp Tyr Glu Gln Asn Leu Tyr Cys S er Gly Asn Gly Tyr Asp
225                 230                 235                 240

Cys Thr Lys Thr Ile Tyr Lys Lys Gly Lys L eu Val Ile Gly Glu His
                245                 250                 255

Cys Thr Asn Cys Ser Val Trp Cys Arg Met T yr Glu Thr Trp Ile Asp
            260                 265                 270

Asn Gln Lys Lys Glu Phe Leu Lys Gln Lys A rg Lys Tyr Glu Thr Glu
        275                 280                 285

Ile Ser Gly Gly Gly Ser Gly Leu Ser Pro L ys Arg Thr Lys Arg Ala
290                 295                 300
```

```
Ala Arg Ser Ser Ser Ser Asp Asp Asn Gly Tyr Glu Ser Lys Phe
305                 310                 315                 320

Tyr Lys Lys Leu Lys Glu Val Gly Tyr Gln Asp Val Asp Lys Phe Leu
            325                 330                 335

Lys Ile Leu Asn Lys Glu Gly Ile Cys Gln Lys Gln Pro Gln Val Gly
            340                 345                 350

Asn Glu Lys Ala Asp Asn Val Asp Phe Thr Asn Glu Lys Tyr Val Lys
            355                 360                 365

Thr Phe Ser Arg Thr Glu Ile Cys Glu Pro Cys Pro Trp Cys Gly Leu
        370                 375                 380

Glu Lys Gly Gly Pro Pro Trp Lys Val Lys Gly Asp Lys Thr Cys Gly
385                 390                 395                 400

Ser Ala Lys Thr Lys Thr Tyr Asp Pro Lys Asn Ile Thr Asp Ile Pro
            405                 410                 415

Val Leu Tyr Pro Asp Lys Ser Gln Gln Asn Ile Leu Lys Lys Tyr Lys
            420                 425                 430

Asn Phe Cys Glu Lys Gly Ala Pro Gly Gly Gly Gln Ile Lys Lys Trp
        435                 440                 445

Gln Cys Tyr Tyr Asp Glu His Arg Pro Ser Ser Lys Asn Asn Asn Asn
    450                 455                 460

Cys Val Glu Gly Thr Trp Asp Lys Phe Thr Gln Gly Lys Gln Thr Val
465                 470                 475                 480

Lys Ser Tyr Asn Val Phe Phe Trp Asp Trp Val His Asp Met Leu His
            485                 490                 495

Asp Ser Val Glu Trp Lys Thr Glu Leu Ser Lys Cys Ile Asn Asn Asn
            500                 505                 510

Thr Asn Gly Asn Thr Cys Arg Asn Asn Lys Cys Lys Thr Asp Cys
        515                 520                 525

Gly Cys Phe Gln Lys Trp Val Glu Lys Gln Gln Glu Trp Met Ala
530                 535                 540

Ile Lys Asp His Phe Gly Lys Gln Thr Asp Ile Val Gln Lys Gly
545                 550                 555                 560

Leu Ile Val Phe Ser Pro Tyr Gly Val Leu Asp Leu Val Leu Lys Gly
            565                 570                 575

Gly Asn Leu Leu Gln Asn Ile Lys Asp Val His Gly Asp Thr Asp Asp
        580                 585                 590

Ile Lys His Ile Lys Lys Leu Leu Asp Glu Glu Asp Ala Val Ala Val
    595                 600                 605

Val Leu Gly Gly Lys Asp Asn Thr Thr Ile Asp Lys Leu Leu Gln His
610                 615                 620

Glu Lys Glu Gln Ala Glu Gln Cys Lys Gln Lys Gln Glu Glu Cys Glu
625                 630                 635                 640

Lys Lys Ala Gln Gln Glu Ser Arg Gly Arg Ser Ala Glu Thr Arg Glu
            645                 650                 655

Asp Glu Arg Thr Gln Gln Pro Ala Asp Ser Ala Gly Glu Val Glu Glu
            660                 665                 670

Glu Glu Asp Asp Asp Asp Tyr Asp Glu Asp Asp Glu Asp Asp Asp Val
        675                 680                 685

Val Gln Asp Val Asp Val Ser Glu Ile Arg Gly Pro
        690                 695                 700

(2) INFORMATION FOR SEQ ID NO:11:

(i) SEQUENCE CHARACTERISTICS:
```

(A) LENGTH: 8220 base pairs
(B) TYPE: nucleic acid
(C) STRANDEDNESS: single
(D) TOPOLOGY: linear (ii) MOLECULE TYPE: DNA (genomic)

(iii) HYPOTHETICAL: NO (vi) ORIGINAL SOURCE:
(A) ORGANISM: Plasmodium falciparum (xi) SEQUENCE DESCRIPTION: SEQ ID NO:11:

```
AAAAATGGGG CCCAAGGAGG CTGCAGGTGG GGATGATATT GAGGATGAAA G TGCCAAACA        60

TATGTTTGAT AGGATAGGAA AGATGTGTA CGATAAAGTA AAAGAGGAAG C TAAAGAACG       120

TGGTAAAGGC TTGCAAGGAC GTTTGTCAGA AGCAAAATTT GAGAAAAATG A AAGCGATCC      180

ACAAACACCA GAAGATCCAT GCGATCTTGA TCATAAATAT CATACAAATG T AACTACTAA      240

TGTAATTAAT CCGTGCGCTG ATAGATCTGA CGTGCGTTTT TCCGATGAAT A TGGAGGTCA      300

ATGTACACAT AATAGAATAA AAGATAGTCA ACAGGGTGAT AATAAAGGTG C ATGTGCTCC      360

ATATAGGCGA TTGCATGTAT GCGATCAAAA TTTAGAACAG ATAGAGCCTA T AAAAATAAC      420

AAATACTCAT AATTTATTGG TAGATGTGTG TATGGCAGCA AAATTTGAAG G ACAATCAAT      480

AACACAAGAT TATCCAAAAT ATCAAGCAAC ATATGGTGAT TCTCCTTCTC A AATATGTAC      540

TATGCTGGCA CGAAGTTTTG CGGACATAGG GGACATTGTC AGAGGAAGAG A TTTGTATTT      600

AGGTAATCCA CAAGAAATAA AACAAAGACA ACAATTAGAA AATAATTTGA A AACAATTTT      660

CGGGAAAATA TATGAAAAAT TGAATGGCGC AGAAGCACGC TACGGAAATG A TCCGGAATT      720

TTTTAAATTA CGAGAAGATT GGTGGACTGC TAATCGAGAA ACAGTATGGA A AGCCATCAC      780

ATGTAACGCT TGGGGTAATA CATATTTTCA TGCAACGTGC AATAGAGGAG A ACGAACTAA      840

AGGTTACTGC CGGTGTAACG ACGACCAAGT TCCCACATAT TTTGATTATG T GCCGCAGTA      900

TCTTCGCTGG TTCGAGGAAT GGGCAGAAGA TTTTTGTAGG AAAAAAAATA A AAAAATAAA      960

AGATGTTAAA AGAAATTGTC GTGGAAAAGA TAAAGAGGAT AAGGATCGAT A TTGTAGCCG     1020

TAATGGCTAC GATTGCGAAA AAACTAAACG AGCGATTGGT AAGTTGCGTT A TGGTAAGCA     1080

ATGCATTAGC TGTTTGTATG CATGTAATCC TTACGTTGAT TGGATAAATA A CCAAAAAGA     1140

ACAATTTGAC AAACAGAAAA AAAAATATGA TGAAGAAATA AAAAAATATG A AAATGGAGC     1200

ATCAGGTGGT AGTAGGCAAA AACGGGATGC AGGTGGTACA ACTACTACTA A TTATGATGG     1260

ATATGAAAAA AAATTTTATG ACGAACTTAA TAAAAGTGAA TATAGAACCG T TGATAAATT     1320

TTTGGAAAAA TTAAGTAATG AAGAAATATG CACAAAAGTT AAAGACGAAG A AGGAGGAAC     1380

AATTGATTTT AAAAACGTTA ATAGTGATAG TACTAGTGGT GCTAGTGGCA C TAATGTTGA     1440

AAGTCAAGGA ACATTTTATC GTTCAAAATA TTGCCAACCC TGCCCTTATT G TGGAGTGAA     1500

AAAGGTAAAT AATGGTGGTA GTAGTAATGA ATGGGAAGAG AAAAATAATG G CAAGTGCAA     1560

GAGTGGAAAA CTTTATGAGC CTAAACCCGA CAAAGAAGGT ACTACTATTA C AATCCTTAA     1620

AAGTGGTAAA GGACATGATG ATATTGAAGA AAAATTAAAC AAATTTTGTG A TGAAAAAAA     1680

TGGTGATACA ATAAATAGTG GTGGTAGTGG TACGGGTGGT AGTGGTGGTG G TAACAGTGG     1740

TAGACAGGAA TTGTATGAAG AATGGAAATG TTATAAAGGT GAAGATGTAG T GAAAGTTGG     1800

ACACGATGAG GATGACGAGG AGGATTATGA AAATGTAAAA AATGCAGGCG G ATTATGTAT     1860

ATTAAAAAAC CAAAAAAAGA ATAAAGAAGA AGGTGGAAAT ACGTCTGAAA A GGAGCCTGA     1920

TGAAATCCAA AAGACATTCA ATCCTTTTTT TTACTATTGG GTTGCACATA T GTTAAAAGA     1980
```

-continued

```
TTCCATACAT TGGAAAAAAA AACTTCAGAG ATGTTTACAA AATGGTAACA G AATAAAATG   2040

TGGAAACAAT AAATGTAATA ATGATTGTGA ATGTTTTAAA AGATGGATTA C ACAAAAAAA   2100

AGACGAATGG GGGAAAATAG TACAACATTT TAAAACGCAA AATATTAAAG G TAGAGGAGG   2160

TAGTGACAAT ACGGCAGAAT TAATCCCATT TGATCACGAT TATGTTCTTC A ATACAATTT   2220

GCAAGAAGAA TTTTTGAAAG GCGATTCCGA AGACGCTTCC GAAGAAAAT C CGAAAATAG   2280

TCTGGATGCA GAGGAGGCAG AGGAACTAAA ACACCTTCGC GAAATCATTG A AAGTGAAGA   2340

CAATAATCAA GAAGCATCTG TTGGTGGTGG CGTCACTGAA CAAAAAAATA T AATGGATAA   2400

ATTGCTCAAC TACGAAAAAG ACGAAGCCGA TTTATGCCTA GAAATTCACG A AGATGAGGA   2460

AGAGGAAAAA GAAAAAGGAG ACGGAAACGA ATGTATCGAA GAGGGCGAAA A TTTTCGTTA   2520

TAATCCATGT AGTGGCGAAA GTGGTAACAA ACGATACCCC GTTCTTGCGA A CAAAGTAGC   2580

GTATCAAATG CATCACAAGG CAAAGACACA ATTGGCTAGT CGTGCTGGTA G AAGTGCGTT   2640

GAGAGGTGAT ATATCCTTAG CGCAATTTAA AAATGGTCGT AACGGAAGTA C ATTGAAAGG   2700

ACAAATTTGC AAAATTAACG AAAACTATTC CAATGATAGT CGTGGTAATA G TGGTGGACC   2760

ATGTACAGGC AAAGATGGAG ATCACGGAGG TGTGCGCATG AGAATAGGAA C GGAATGGTC   2820

AAATATTGAA GGAAAAAAAC AAACGTCATA CAAAAACGTC TTTTTACCTC C CCGACGAGA   2880

ACACATGTGT ACATCCAATT TAGAAAATTT AGATGTTGGT AGTGTCACTA A AAATGATAA   2940

GGCTAGCCAC TCATTATTGG GAGATGTTCA GCTCGCAGCA AAAACTGATG C AGCTGAGAT   3000

AATAAAACGC TATAAAGATC AAAATAATAT ACAACTAACT GATCCAATAC A ACAAAAAGA   3060

CCAGGAGGCT ATGTGTCGAG CTGTACGTTA TAGTTTTGCC GATTTAGGAG A CATTATTCG   3120

AGGAAGAGAT ATGTGGGATG AGGATAAGAG CTCAACAGAC ATGGAAACAC G TTTGATAAC   3180

CGTATTTAAA AACATTAAAG AAAAACATGA TGGAATCAAA GACAACCCTA A ATATACCGG   3240

TGATGAAAGC AAAAAGCCCG CATATAAAAA ATTACGAGCA GATTGGTGGG A AGCAAATAG   3300

ACATCAAGTG TGGAGAGCCA TGAAATGCGC AACAAAAGGC ATCATATGTC C TGGTATGCC   3360

AGTTGACGAT TATATCCCCC AACGTTTACG CTGGATGACT GAATGGGCTG A ATGGTATTG   3420

TAAAGCGCAA TCACAGGAGT ATGACAAGTT AAAAAAAATC TGTGCAGATT G TATGAGTAA   3480

GGGTGATGGA AAATGTACGC AAGGTGATGT CGATTGTGGA AAGTGCAAAG C AGCATGTGA   3540

TAAATATAAA GAGGAAATAG AAAAATGGAA TGAACAATGG AGAAAAATAT C AGATAAATA   3600

CAATCTATTA TACCTACAAG CAAAAACTAC TTCTACTAAT CCTGGCCGTA C TGTTCTTGG   3660

TGATGACGAT CCCGACTATC AACAAATGGT AGATTTTTTG ACCCCAATAC A CAAAGCAAG   3720

TATTGCCGCA CGTGTTCTTG TTAAACGTGC TGCTGGTAGT CCCACTGAGA T CGCCGCCGC   3780

CGCCCCGATC ACCCCCTACA GTACTGCTGC CGGATATATA CACCAGGAAA T AGGATATGG   3840

GGGGTGCCAG GAACAAACAC AATTTTGTGA AAAAAAACAT GGTGCAACAT C AACTAGTAC   3900

CACGAAAGAA AACAAAGAAT ACACCTTTAA ACAACCTCCG CCGGAGTATG C TACAGCGTG   3960

TGATTGCATA AATAGGTCGC AAACAGAGGA GCCGAAGAAA AAGGAAGAAA A TGTAGAGAG   4020

TGCCTGCAAA ATAGTGGAGA AAATACTTGA GGGTAAGAAT GGAAGGACTA C AGTAGGTGA   4080

ATGTAATCCA AAAGAGAGTT ATCCTGATTG GGATTGCAAA AACAATATTG A CATTAGTCA   4140

TGATGGTGCT TGTATGCCTC CAAGGAGACA AAAACTATGT TTATATTATA T AGCACATGA   4200

GAGTCAAACA GAAAATATAA AAACAGACGA TAATTTGAAA GATGCTTTTA T TAAAACTGC   4260

AGCAGCAGAA ACTTTTCTTT CATGGCAATA TTATAAGAGT AAGAATGATA G TGAAGCTAA   4320
```

```
AATATTAGAT AGAGGCCTTA TTCCATCCCA ATTTTTAAGA TCCATGATGT A CACGTTTGG    4380

AGATTATAGA GATATATGTT TGAACACAGA TATATCTAAA AAACAAAATG A TGTAGCTAA    4440

GGCAAAAGAT AAAATAGGTA AATTTTTCTC AAAAGATGGC AGCAAATCTC C TAGTGGCTT    4500

ATCACGCCAA GAATGGTGGA AAACAAATGG TCCAGAGATT TGGAAAGGAA T GTTATGTGC    4560

CTTAACAAAA TACGTCACAG ATACCGAATA CAAAAGAAAA ATCAAAAACG A CTACTCATA    4620

CGATAAAGTC AACCAATCCC AAAATGGCAA CCCTTCCCTT GAAGAGTTTG C TGCTAAACC    4680

TCAATTTCTA CGTTGGATGA TCGAATGGGG AGAAGAGTTT TGTGCTGAAC G TCAGAAGAA    4740

GGAAAATATC ATAAAAGATG CATGTAATGA AATAAATTCT ACACAACAGT G TAATGATGC    4800

GAAACATCGT TGTAATCAAG CATGTAGAGC ATATCAAGAA TATGTTGAAA A TAAAAAAAA    4860

AGAATTTTCG GGACAAACAA ATAACTTTGT TCTAAAGGCA AATGTTCAGC C CCAAGATCC    4920

AGAATATAAA GGATATGAAT ATAAAGACGG CGTACAACCG ATACAGGGGA A TGAGTATTT    4980

ACTGCAAAAA TGTGATAATA ATAAATGTTC TTGCATGGAT GGAAATGTAC T TTCCGTCTC    5040

TCCAAAAGAA AAACCTTTTG GAAAATATGC CCATAAATAT CCTGAGAAAT G TGATTGTTA    5100

TCAAGGAAAA CATGTACCTA GCATACCACC TCCCCCCCCA CCTGTACAAC C ACAACCGGA    5160

AGCACCAACA GTAACAGTAG ACGTTTGCAG CATAGTAAAA ACACTATTTA A AGACACAAA    5220

CAATTTTTCC GACGCTTGTG GTCTAAAATA CGGCAAAACC GCACCATCCA G TTGGAAATG    5280

TATACCAAGT GACACAAAAA GTGGTGCTGG TGCCACCACC GGCAAAAGTG G TAGTGATAG    5340

TGGTAGTATT TGTATCCCAC CCAGGAGGCG ACGATTATAT GTGGGGAAAC T ACAGGAGTG    5400

GGCTACCGCG CTCCCACAAG GTGAGGGCGC CGCGCCGTCC CACTCACGCG C CGACGACTT    5460

GCGCAATGCG TTCATCCAAT CTGCTGCAAT AGAGACTTTT TTCTTATGGG A TAGATATAA    5520

AGAAGAGAAA AAACCACAGG GTGATGGGTC ACAACAAGCA CTATCACAAC T AACCAGTAC    5580

ATACAGTGAT GACGAGGAGG ACCCCCCCGA CAAACTGTTA CAAATGGTA A GATACCCCC    5640

CGATTTTTTG AGATTAATGT TCTATACATT AGGAGATTAT AGGGATATTT T AGTACACGG    5700

TGGTAACACA AGTGACAGTG GTAACACAAA TGGTAGTAAC AACAACAATA T TGTGCTTGA    5760

AGCGAGTGGT AACAAGGAGG ACATGCAAAA AATACAAGAG AAAATAGAAC A AATTCTCCC    5820

AAAAAATGGT GGCACACCTC TTGTCCCAAA ATCTAGTGCC CAAACACCTG A TAAATGGTG    5880

GAATGAACAC GCCGAATCTA TCTGGAAAGG TATGATATGT GCATTGACAT A TACAGAAAA    5940

GAACCCTGAC ACCAGTGCAA GAGGCGACGA AAACAAAATA GAAAAGGATG A TGAAGTGTA    6000

CGAGAAATTT TTTGGCAGCA CAGCCGACAA ACATGGCACA GCCTCAACCC C AACCGGCAC    6060

ATACAAAACC CAATACGACT ACGAAAAAGT CAAACTTGAG GATACAAGTG G TGCCAAAAC    6120

CCCCTCAGCC TCTAGTGATA CACCCCTTCT CTCCGATTTC GTGTTACGCC C CCCCTACTT    6180

CCGTTACCTT GAAGAATGGG GTCAAAATTT TTGTAAAAAA AGAAAGCATA A ATTGGCACA    6240

AATAAAACAT GAGTGTAAAG TAGAAGAAAA TGGTGGTGGT AGTCGTCGTG G TGGTATAAC    6300

AAGACAATAT AGTGGGGATG GCGAAGCGTG TAATGAGATG CTTCCAAAAA A CGATGGAAC    6360

TGTTCCGGAT TTAGAAAAGC CGAGTTGTGC CAAACCTTGT AGTTCTTATA G AAAATGGAT    6420

AGAAAGCAAG GGAAAAGAGT TTGAGAAACA AGAAAAGGCA TATGAACAAC A AAAAGACAA    6480

ATGTGTAAAT GGAAGTAATA AGCATGATAA TGGATTTTGT GAAACACTAA C AACGTCCTC    6540

TAAAGCTAAA GACTTTTTAA AAACGTTAGG ACCATGTAAA CCTAATAATG T AGAGGGTAA    6600

AACAATTTTT GATGATGATA AAACCTTTAA ACATACAAAA GATTGTGATC C ATGTCTTAA    6660

ATTTAGTGTT AATTGTAAAA AAGATGAATG TGATAATTCT AAAGGAACCG A TTGCCGAAA    6720
```

-continued

```
TAAAAATAGT ATTGATGCAA CAGATATTGA AAATGGAGTG GATTCTACTG T ACTAGAAAT     6780

GCGTGTCAGT GCTGATAGTA AAAGTGGATT TAATGGTGAT GGTTTAGAGA A TGCTTGTAG     6840

AGGTGCTGGT ATCTTTGAAG GTATTAGAAA AGATGAATGG AAATGTCGTA A TGTATGTGG    6900

TTATGTTGTA TGTAAACCGG AAAACGTTAA TGGGGAAGCA AAGGGAAAAC A CATTATACA    6960

AATTAGAGCA CTGGTTAAAC GTTGGGTAGA ATATTTTTTT GAAGATTATA A TAAAATAAA    7020

ACATAAAATT TCACATCGCA TAAAAAATGG TGAAATATCT CCATGTATAA A AAATTGTGT    7080

AGAAAAATGG GTAGATCAGA AAAGAAAAGA ATGGAAGGAA ATTACTGAAC G TTTCAAAGA   7140

TCAATATAAA AATGACAATT CAGATGATGA CAATGTGAGA AGTTTTTTGG A GACCTTGAT   7200

ACCTCAAATT ACTGATGCAA ACGCTAAAAA TAAGGTTATA AAATTAAGTA A GTTCGGTAA   7260

TTCTTGTGGA TGTAGTGCCA GTGCGAACGA ACAAACAAA AATGGTGAAT A CAAGGACGC   7320

TATAGATTGT ATGCTTAAAA AGCTTAAAGA TAAAATTGGC GAGTGCGAAA A GAAACACCA   7380

TCAAACTAGT GATACCGAGT GTTCCGACAC ACCACAACCG CAAACCCTTG A AGACGAAAC   7440

TTTGGATGAT GATATAGAAA CAGAGGAGGC GAAGAAGAAC ATGATGCCGA A AATTTGTGA   7500

AAATGTGTTA AAAACAGCAC AACAAGAGGA TGAAGGCGGT TGTGTCCCAG C AGAAAATAG   7560

TGAAGAACCG GCAGCAACAG ATAGTGGTAA GGAAACCCCC GAACAAACCC C CGTTCTCAA   7620

ACCCGAAGAA GAAGCAGTAC CGGAACCACC ACCTCCACCC CCACAGGAAA A AGCCCCGGC   7680

ACCAATACCC CAACCACAAC CACCAACCCC CCCCACACAA CTCTTGGATA A TCCCCACGT   7740

TCTAACCGCC CTGGTGACCT CCACCCTCGC CTGGAGCGTT GGCATCGGTT T TGCTACATT   7800

CACTTATTTT TATCTAAAGG TAAATGGAAG TATATATATG GGGATGTGGA T GTATGTGGA   7860

TGTATGTGAA TGTATGTGGA TGTATGTGGA TGTATGTGGA TGTGTTTTAT G GATATGTAT   7920

TTGTGATTAT GTTTGGATAT ATATATATAT ATATATATGT TTATGTATAT G TGTTTTTGG   7980

ATATATATAT GTGTATGTAT ATGATTTTCT GTATATGTAT TTGTGGGTTA A GGATATATA   8040

TATATGGATG TACTTGTATG TGTTTTATAT ATATATTTTA TATATATGTA T TTATATTAA   8100

AAAAGAAATA TAAAAACAAA TTTATTAAAA TGAAAAAAG AAAAATGAAA T ATAAAAAAA   8160

AATTTATTAA ATAAAAAAA AAAAAAAAA AAAAGGAGAA AAATTTTTTA A AAAATAATA   8220
```

(2) INFORMATION FOR SEQ ID NO:12:

(i) SEQUENCE CHARACTERISTICS:
        (A) LENGTH: 2710 amino acids
        (B) TYPE: amino acid
        (C) STRANDEDNESS: single
        (D) TOPOLOGY: linear (ii) MOLECULE TYPE: protein (iii) HYPOTHETICAL: NO (vi) ORIGINAL SOURCE:
        (A) ORGANISM: Plasmodium falciparum (xi) SEQUENCE DESCRIPTION: SEQ ID NO:12:

```
Asn Val Met Val Glu Leu Ala Lys Met Gly P ro Lys Glu Ala Ala Gly
 1               5                  10                  15

Gly Asp Asp Ile Glu Asp Glu Ser Ala Lys H is Met Phe Asp Arg Ile
            20                  25                  30

Gly Lys Asp Val Tyr Asp Lys Val Lys Glu G lu Ala Lys Glu Arg Gly
        35                  40                  45

Lys Gly Leu Gln Gly Arg Leu Ser Glu Ala L ys Phe Glu Lys Asn Glu
```

```
               50                  55                  60
Ser Asp Pro Gln Thr Pro Glu Asp Pro Cys Asp Leu Asp His Lys Tyr
65                  70                  75                  80

His Thr Asn Val Thr Thr Asn Val Ile Asn Pro Cys Ala Asp Arg Ser
                85                  90                  95

Asp Val Arg Phe Ser Asp Glu Tyr Gly Gly Gln Cys Thr His Asn Arg
                100                 105                 110

Ile Lys Asp Ser Gln Gln Gly Asp Asn Lys Gly Ala Cys Ala Pro Tyr
                115                 120                 125

Arg Arg Leu His Val Cys Asp Gln Asn Leu Glu Gln Ile Glu Pro Ile
                130                 135                 140

Lys Ile Thr Asn Thr His Asn Leu Leu Val Asp Val Cys Met Ala Ala
145                 150                 155                 160

Lys Phe Glu Gly Gln Ser Ile Thr Gln Asp Tyr Pro Lys Tyr Gln Ala
                165                 170                 175

Thr Tyr Gly Asp Ser Pro Ser Gln Ile Cys Thr Met Leu Ala Arg Ser
                180                 185                 190

Phe Ala Asp Ile Gly Asp Ile Val Arg Gly Arg Asp Leu Tyr Leu Gly
                195                 200                 205

Asn Pro Gln Glu Ile Lys Gln Arg Gln Gln Leu Glu Asn Asn Leu Lys
                210                 215                 220

Thr Ile Phe Gly Lys Ile Tyr Glu Lys Leu Asn Gly Ala Glu Ala Arg
225                 230                 235                 240

Tyr Gly Asn Asp Pro Glu Phe Phe Lys Leu Arg Glu Asp Trp Trp Thr
                245                 250                 255

Ala Asn Arg Glu Thr Val Trp Lys Ala Ile Thr Cys Asn Ala Trp Gly
                260                 265                 270

Asn Thr Tyr Phe His Ala Thr Cys Asn Arg Gly Glu Arg Thr Lys Gly
                275                 280                 285

Tyr Cys Arg Cys Asn Asp Asp Gln Val Pro Thr Tyr Phe Asp Tyr Val
                290                 295                 300

Pro Gln Tyr Leu Arg Trp Phe Glu Glu Trp Ala Asp Phe Cys Arg
305                 310                 315                 320

Lys Lys Asn Lys Lys Ile Lys Asp Val Lys Arg Asn Cys Arg Gly Lys
                325                 330                 335

Asp Lys Glu Asp Lys Asp Arg Tyr Cys Ser Arg Asn Gly Tyr Asp Cys
                340                 345                 350

Glu Lys Thr Lys Arg Ala Ile Gly Lys Leu Arg Tyr Gly Lys Gln Cys
                355                 360                 365

Ile Ser Cys Leu Tyr Ala Cys Asn Pro Tyr Val Asp Trp Ile Asn Asn
                370                 375                 380

Gln Lys Glu Gln Phe Asp Lys Gln Lys Lys Lys Tyr Asp Glu Glu Ile
385                 390                 395                 400

Lys Lys Tyr Glu Asn Gly Ala Ser Gly Gly Ser Arg Gln Lys Arg Asp
                405                 410                 415

Ala Gly Gly Thr Thr Thr Thr Asn Tyr Asp Gly Tyr Glu Lys Lys Phe
                420                 425                 430

Tyr Asp Glu Leu Asn Lys Ser Glu Tyr Arg Thr Val Asp Lys Phe Leu
                435                 440                 445

Glu Lys Leu Ser Asn Glu Glu Ile Cys Thr Lys Val Lys Asp Glu Glu
                450                 455                 460

Gly Gly Thr Ile Asp Phe Lys Asn Val Asn Ser Asp Ser Thr Ser Gly
465                 470                 475                 480
```

```
Ala Ser Gly Thr Asn Val Glu Ser Gln Gly Thr Phe Tyr Arg Ser Lys
            485                 490                 495
Tyr Cys Gln Pro Cys Pro Tyr Cys Gly Val Lys Lys Val Asn Asn Gly
            500                 505                 510
Gly Ser Ser Asn Glu Trp Glu Lys Asn Asn Gly Lys Cys Lys Ser
            515                 520                 525
Gly Lys Leu Tyr Glu Pro Lys Pro Asp Lys Glu Gly Thr Thr Ile Thr
            530                 535                 540
Ile Leu Lys Ser Gly Lys Gly His Asp Ile Glu Glu Lys Leu Asn
545                 550                 555                 560
Lys Phe Cys Asp Glu Lys Asn Gly Asp Thr Ile Asn Ser Gly Gly Ser
            565                 570                 575
Gly Thr Gly Gly Ser Gly Gly Asn Ser Gly Arg Gln Glu Leu Tyr
            580                 585                 590
Glu Glu Trp Lys Cys Tyr Lys Gly Glu Asp Val Val Lys Val Gly His
            595                 600                 605
Asp Glu Asp Asp Glu Glu Asp Tyr Glu Asn Val Lys Asn Ala Gly Gly
            610                 615                 620
Leu Cys Ile Leu Lys Asn Gln Lys Lys Asn Lys Glu Glu Gly Gly Asn
625                 630                 635                 640
Thr Ser Glu Lys Glu Pro Asp Glu Ile Gln Lys Thr Phe Asn Pro Phe
            645                 650                 655
Phe Tyr Tyr Trp Val Ala His Met Leu Lys Asp Ser Ile His Trp Lys
            660                 665                 670
Lys Lys Leu Gln Arg Cys Leu Gln Asn Gly Asn Arg Ile Lys Cys Gly
            675                 680                 685
Asn Asn Lys Cys Asn Asn Asp Cys Glu Cys Phe Lys Arg Trp Ile Thr
690                 695                 700
Gln Lys Lys Asp Glu Trp Gly Lys Ile Val Gln His Phe Lys Thr Gln
705                 710                 715                 720
Asn Ile Lys Gly Arg Gly Gly Ser Asp Asn Thr Ala Glu Leu Ile Pro
            725                 730                 735
Phe Asp His Asp Tyr Val Leu Gln Tyr Asn Leu Gln Glu Glu Phe Leu
            740                 745                 750
Lys Gly Asp Ser Glu Asp Ala Ser Glu Glu Lys Ser Glu Asn Ser Leu
            755                 760                 765
Asp Ala Glu Glu Ala Glu Leu Lys His Leu Arg Glu Ile Ile Glu
            770                 775                 780
Ser Glu Asp Asn Asn Gln Glu Ala Ser Val Gly Gly Gly Val Thr Glu
785                 790                 795                 800
Gln Lys Asn Ile Met Asp Lys Leu Leu Asn Tyr Glu Lys Asp Glu Ala
            805                 810                 815
Asp Leu Cys Leu Glu Ile His Glu Asp Glu Glu Glu Glu Lys Glu Lys
            820                 825                 830
Gly Asp Gly Asn Glu Cys Ile Glu Glu Gly Glu Asn Phe Arg Tyr Asn
            835                 840                 845
Pro Cys Ser Gly Glu Ser Gly Asn Lys Arg Tyr Pro Val Leu Ala Asn
            850                 855                 860
Lys Val Ala Tyr Gln Met His His Lys Ala Lys Thr Gln Leu Ala Ser
865                 870                 875                 880
Arg Ala Gly Arg Ser Ala Leu Arg Gly Asp Ile Ser Leu Ala Gln Phe
            885                 890                 895
```

```
-continued

Lys Asn Gly Arg Asn Gly Ser Thr Leu Lys Gly Gln Ile Cys Lys Ile
            900                 905                 910
Asn Glu Asn Tyr Ser Asn Asp Ser Arg Gly Asn Ser Gly Gly Pro Cys
            915                 920                 925
Thr Gly Lys Asp Gly Asp His Gly Gly Val Arg Met Arg Ile Gly Thr
            930                 935                 940
Glu Trp Ser Asn Ile Glu Gly Lys Lys Gln Thr Ser Tyr Lys Asn Val
945                 950                 955                 960
Phe Leu Pro Pro Arg Arg Glu His Met Cys Thr Ser Asn Leu Glu Asn
                965                 970                 975
Leu Asp Val Gly Ser Val Thr Lys Asn Asp Lys Ala Ser His Ser Leu
            980                 985                 990
Leu Gly Asp Val Gln Leu Ala Ala Lys Thr Asp Ala Ala Glu Ile Ile
            995                 1000                1005
Lys Arg Tyr Lys Asp Gln Asn Asn Ile Gln Leu Thr Asp Pro Ile Gln
            1010                1015                1020
Gln Lys Asp Gln Glu Ala Met Cys Arg Ala Val Arg Tyr Ser Phe Ala
1025                1030                1035                1040
Asp Leu Gly Asp Ile Ile Arg Gly Arg Asp Met Trp Asp Glu Asp Lys
                1045                1050                1055
Ser Ser Thr Asp Met Glu Thr Arg Leu Ile Thr Val Phe Lys Asn Ile
            1060                1065                1070
Lys Glu Lys His Asp Gly Ile Lys Asp Asn Pro Lys Tyr Thr Gly Asp
            1075                1080                1085
Glu Ser Lys Lys Pro Ala Tyr Lys Lys Leu Arg Ala Asp Trp Trp Glu
            1090                1095                1100
Ala Asn Arg His Gln Val Trp Arg Ala Met Lys Cys Ala Thr Lys Gly
1105                1110                1115                1120
Ile Ile Cys Pro Gly Met Pro Val Asp Asp Tyr Ile Pro Gln Arg Leu
                1125                1130                1135
Arg Trp Met Thr Glu Trp Ala Glu Trp Tyr Cys Lys Ala Gln Ser Gln
            1140                1145                1150
Glu Tyr Asp Lys Leu Lys Lys Ile Cys Ala Asp Cys Met Ser Lys Gly
            1155                1160                1165
Asp Gly Lys Cys Thr Gln Gly Asp Val Asp Cys Gly Lys Cys Lys Ala
            1170                1175                1180
Ala Cys Asp Lys Tyr Lys Glu Glu Ile Glu Lys Trp Asn Glu Gln Trp
1185                1190                1195                1200
Arg Lys Ile Ser Asp Lys Tyr Asn Leu Leu Tyr Leu Gln Ala Lys Thr
            1205                1210                1215
Thr Ser Thr Asn Pro Gly Arg Thr Val Leu Gly Asp Asp Asp Pro Asp
            1220                1225                1230
Tyr Gln Gln Met Val Asp Phe Leu Thr Pro Ile His Lys Ala Ser Ile
            1235                1240                1245
Ala Ala Arg Val Leu Val Lys Arg Ala Ala Gly Ser Pro Thr Glu Ile
            1250                1255                1260
Ala Ala Ala Ala Pro Ile Thr Pro Tyr Ser Thr Ala Ala Gly Tyr Ile
1265                1270                1275                1280
His Gln Glu Ile Gly Tyr Gly Gly Cys Gln Glu Gln Thr Gln Phe Cys
            1285                1290                1295
Glu Lys Lys His Gly Ala Thr Ser Thr Ser Thr Thr Lys Glu Asn Lys
            1300                1305                1310
Glu Tyr Thr Phe Lys Gln Pro Pro Glu Tyr Ala Thr Ala Cys Asp
```

-continued

```
              1315                1320                1325
Cys Ile Asn Arg Ser Gln Thr Glu Pro Lys Lys Lys Glu Glu Asn
    1330                1335                1340
Val Glu Ser Ala Cys Lys Ile Val Glu Lys Ile Leu Glu Gly Lys Asn
1345                1350                1355                1360
Gly Arg Thr Thr Val Gly Glu Cys Asn Pro Lys Glu Ser Tyr Pro Asp
                1365                1370                1375
Trp Asp Cys Lys Asn Asn Ile Asp Ile Ser His Asp Gly Ala Cys Met
            1380                1385                1390
Pro Pro Arg Arg Gln Lys Leu Cys Leu Tyr Tyr Ile Ala His Glu Ser
            1395                1400                1405
Gln Thr Glu Asn Ile Lys Thr Asp Asp Asn Leu Lys Asp Ala Phe Ile
    1410                1415                1420
Lys Thr Ala Ala Ala Glu Thr Phe Leu Ser Trp Gln Tyr Tyr Lys Ser
1425                1430                1435                1440
Lys Asn Asp Ser Glu Ala Lys Ile Leu Asp Arg Gly Leu Ile Pro Ser
                1445                1450                1455
Gln Phe Leu Arg Ser Met Met Tyr Thr Phe Gly Asp Tyr Arg Asp Ile
            1460                1465                1470
Cys Leu Asn Thr Asp Ile Ser Lys Lys Gln Asn Asp Val Ala Lys Ala
            1475                1480                1485
Lys Asp Lys Ile Gly Lys Phe Phe Ser Lys Asp Gly Ser Lys Ser Pro
    1490                1495                1500
Ser Gly Leu Ser Arg Gln Glu Trp Trp Lys Thr Asn Gly Pro Glu Ile
1505                1510                1515                1520
Trp Lys Gly Met Leu Cys Ala Leu Thr Lys Tyr Val Thr Asp Thr Asp
                1525                1530                1535
Asn Lys Arg Lys Ile Lys Asn Asp Tyr Ser Tyr Asp Lys Val Asn Gln
            1540                1545                1550
Ser Gln Asn Gly Asn Pro Ser Leu Glu Glu Phe Ala Ala Lys Pro Gln
            1555                1560                1565
Phe Leu Arg Trp Met Ile Glu Trp Gly Glu Glu Phe Cys Ala Glu Arg
    1570                1575                1580
Gln Lys Lys Glu Asn Ile Ile Lys Asp Ala Cys Asn Glu Ile Asn Ser
1585                1590                1595                1600
Thr Gln Gln Cys Asn Asp Ala Lys His Arg Cys Asn Gln Ala Cys Arg
                1605                1610                1615
Ala Tyr Gln Glu Tyr Val Glu Asn Lys Lys Lys Glu Phe Ser Gly Gln
            1620                1625                1630
Thr Asn Asn Phe Val Leu Lys Ala Asn Val Gln Pro Gln Asp Pro Glu
            1635                1640                1645
Tyr Lys Gly Tyr Glu Tyr Lys Asp Gly Val Gln Pro Ile Gln Gly Asn
    1650                1655                1660
Glu Tyr Leu Leu Gln Lys Cys Asp Asn Lys Cys Ser Cys Met Asp
1665                1670                1675                1680
Gly Asn Val Leu Ser Val Ser Pro Lys Glu Lys Pro Phe Gly Lys Tyr
                1685                1690                1695
Ala His Lys Tyr Pro Glu Lys Cys Asp Cys Tyr Gln Gly Lys His Val
            1700                1705                1710
Pro Ser Ile Pro Pro Pro Pro Pro Val Gln Pro Gln Pro Glu Ala
    1715                1720                1725
Pro Thr Val Thr Val Asp Val Cys Ser Ile Val Lys Thr Leu Phe Lys
    1730                1735                1740
```

```
Asp Thr Asn Asn Phe Ser Asp Ala Cys Gly L eu Lys Tyr Gly Lys Thr
1745                175 0                 1755                1760

Ala Pro Ser Ser Trp Lys Cys Ile Pro Ser A sp Thr Lys Ser Gly Ala
            1765                1770                1775

Gly Ala Thr Thr Gly Lys Ser Gly Ser Asp S er Gly Ser Ile Cys Ile
            1780                1785                1790

Pro Pro Arg Arg Arg Arg Leu Tyr Val Gly L ys Leu Gln Glu Trp Ala
            1795                1800                1805

Thr Ala Leu Pro Gln Gly Glu Gly Ala Ala P ro Ser His Ser Arg Ala
            1810                1815                1820

Asp Asp Leu Arg Asn Ala Phe Ile Gln Ser A la Ala Ile Glu Thr Phe
1825                183 0                 1835                1840

Phe Leu Trp Asp Arg Tyr Lys Glu Glu Lys L ys Pro Gln Gly Asp Gly
            1845                1850                1855

Ser Gln Gln Ala Leu Ser Gln Leu Thr Ser T hr Tyr Ser Asp Asp Glu
            1860                1865                1870

Glu Asp Pro Pro Asp Lys Leu Leu Gln Asn G ly Lys Ile Pro Pro Asp
            1875                1880                1885

Phe Leu Arg Leu Met Phe Tyr Thr Leu Gly A sp Tyr Arg Asp Ile Leu
            1890                1895                1900

Val His Gly Gly Asn Thr Ser Asp Ser Gly A sn Thr Asn Gly Ser Asn
1905                191 0                 1915                1920

Asn Asn Asn Ile Val Leu Glu Ala Ser Gly A sn Lys Glu Asp Met Gln
            1925                1930                1935

Lys Ile Gln Glu Lys Ile Glu Gln Ile Leu P ro Lys Asn Gly Gly Thr
            1940                1945                1950

Pro Leu Val Pro Lys Ser Ser Ala Gln Thr P ro Asp Lys Trp Trp Asn
            1955                1960                1965

Glu His Ala Glu Ser Ile Trp Lys Gly Met I le Cys Ala Leu Thr Tyr
            1970                1975                1980

Thr Glu Lys Asn Pro Asp Thr Ser Ala Arg G ly Asp Glu Asn Lys Ile
1985                199 0                 1995                2000

Glu Lys Asp Asp Glu Val Tyr Glu Lys Phe P he Gly Ser Thr Ala Asp
            2005                2010                2015

Lys His Gly Thr Ala Ser Thr Pro Thr Gly T hr Tyr Lys Thr Gln Tyr
            2020                2025                2030

Asp Tyr Glu Lys Val Lys Leu Glu Asp Thr S er Gly Ala Lys Thr Pro
            2035                2040                2045

Ser Ala Ser Ser Asp Thr Pro Leu Leu Ser A sp Phe Val Leu Arg Pro
            2050                2055                2060

Pro Tyr Phe Arg Tyr Leu Glu Glu Trp Gly G ln Asn Phe Cys Lys Lys
2065                207 0                 2075                2080

Arg Lys His Lys Leu Ala Gln Ile Lys His G lu Cys Lys Val Glu Glu
            2085                2090                2095

Asn Gly Gly Gly Ser Arg Arg Gly Gly Ile T hr Arg Gln Tyr Ser Gly
            2100                2105                2110

Asp Gly Glu Ala Cys Asn Glu Met Leu Pro L ys Asn Asp Gly Thr Val
            2115                2120                2125

Pro Asp Leu Glu Lys Pro Ser Cys Ala Lys P ro Cys Ser Ser Tyr Arg
            2130                2135                2140

Lys Trp Ile Glu Ser Lys Gly Lys Glu Phe G lu Lys Gln Glu Lys Ala
2145                215 0                 2155                2160
```

-continued

```
Tyr Glu Gln Gln Lys Asp Lys Cys Val Asn Gly Ser Asn Lys His Asp
                2165                2170                2175
Asn Gly Phe Cys Glu Thr Leu Thr Thr Ser Ser Lys Ala Lys Asp Phe
            2180                2185                2190
Leu Lys Thr Leu Gly Pro Cys Lys Pro Asn Asn Val Glu Gly Lys Thr
        2195                2200                2205
Ile Phe Asp Asp Lys Thr Phe Lys His Thr Lys Asp Cys Asp Pro
    2210                2215                2220
Cys Leu Lys Phe Ser Val Asn Cys Lys Lys Asp Glu Cys Asp Asn Ser
2225                2230                2235                2240
Lys Gly Thr Asp Cys Arg Asn Lys Asn Ser Ile Asp Ala Thr Asp Ile
            2245                2250                2255
Glu Asn Gly Val Asp Ser Thr Val Leu Glu Met Arg Val Ser Ala Asp
            2260                2265                2270
Ser Lys Ser Gly Phe Asn Gly Asp Gly Leu Glu Asn Ala Cys Arg Gly
        2275                2280                2285
Ala Gly Ile Phe Glu Gly Ile Arg Lys Asp Glu Trp Lys Cys Arg Asn
    2290                2295                2300
Val Cys Gly Tyr Val Val Cys Lys Pro Glu Asn Val Asn Gly Glu Ala
2305                2310                2315                2320
Lys Gly Lys His Ile Ile Gln Ile Arg Ala Leu Val Lys Arg Trp Val
            2325                2330                2335
Glu Tyr Phe Phe Glu Asp Tyr Asn Lys Ile Lys His Lys Ile Ser His
            2340                2345                2350
Arg Ile Lys Asn Gly Glu Ile Ser Pro Cys Ile Lys Asn Cys Val Glu
        2355                2360                2365
Lys Trp Val Asp Gln Lys Arg Lys Glu Trp Lys Glu Ile Thr Glu Arg
    2370                2375                2380
Phe Lys Asp Gln Tyr Lys Asn Asp Asn Ser Asp Asp Asp Asn Val Arg
2385                2390                2395                2400
Ser Phe Leu Glu Thr Leu Ile Pro Gln Ile Thr Asp Ala Asn Ala Lys
            2405                2410                2415
Asn Lys Val Ile Lys Leu Ser Lys Phe Gly Asn Ser Cys Gly Cys Ser
            2420                2425                2430
Ala Ser Ala Asn Glu Gln Asn Lys Asn Gly Glu Tyr Lys Asp Ala Ile
        2435                2440                2445
Asp Cys Met Leu Lys Lys Leu Lys Asp Lys Ile Gly Glu Cys Glu Lys
    2450                2455                2460
Lys His His Gln Thr Ser Asp Thr Glu Cys Ser Asp Thr Pro Gln Pro
2465                2470                2475                2480
Gln Thr Leu Glu Asp Glu Thr Leu Asp Asp Asp Ile Glu Thr Glu Glu
            2485                2490                2495
Ala Lys Lys Asn Met Met Pro Lys Ile Cys Glu Asn Val Leu Lys Thr
            2500                2505                2510
Ala Gln Gln Glu Asp Glu Gly Gly Cys Val Pro Ala Glu Asn Ser Glu
        2515                2520                2525
Glu Pro Ala Ala Thr Asp Ser Gly Lys Glu Thr Pro Glu Gln Thr Pro
    2530                2535                2540
Val Leu Lys Pro Glu Glu Glu Ala Val Pro Glu Pro Pro Pro Pro
2545                2550                2555                2560
Pro Gln Glu Lys Ala Pro Ala Pro Ile Pro Gln Pro Gln Pro Pro Thr
            2565                2570                2575
Pro Pro Thr Gln Leu Leu Asp Asn Pro His Val Leu Thr Ala Leu Val
```

```
                          2580              2585              2590
Thr Ser Thr Leu Ala Trp Ser Val Gly Ile Gly Phe Ala Thr Phe Thr
                2595              2600              2605

Tyr Phe Tyr Leu Lys Val Asn Gly Ser Ile Tyr Met Gly Met Trp Met
    2610              2615              2620

Tyr Val Asp Val Cys Glu Cys Met Trp Met Tyr Val Asp Val Cys Gly
2625              2630              2635              2640

Cys Val Leu Trp Ile Cys Ile Cys Asp Tyr Val Trp Ile Tyr Ile Tyr
                2645              2650              2655

Ile Tyr Ile Cys Leu Cys Ile Cys Val Phe Gly Tyr Ile Tyr Val Tyr
                2660              2665              2670

Val Tyr Asp Phe Leu Tyr Met Tyr Leu Trp Val Lys Asp Ile Tyr Ile
        2675              2680              2685

Trp Met Tyr Leu Tyr Val Phe Tyr Ile Tyr Ile Leu Tyr Ile Cys Ile
    2690              2695              2700

Tyr Ile Lys Lys Glu Ile
2705              2710
```

(2) INFORMATION FOR SEQ ID NO:13:

(i) SEQUENCE CHARACTERISTICS:
        (A) LENGTH: 291 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO:13:

```
Cys Xaa Xaa Xaa Xaa Xaa Xaa Xaa Xaa Xaa Xaa Xaa Cys Xaa Xaa
1               5                   10                  15

Xaa Xaa Xaa Val Cys Ile Pro Asp Arg Arg Tyr Gln Leu Cys Met Lys
            20                  25                  30

Glu Leu Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa Xaa
    50                  55                  60

Xaa Xaa Xaa Xaa Xaa Xaa Xaa Xaa Xaa Xaa Xaa Xaa Xaa Xaa Xaa
65                  70                  75                  80

Xaa Asp Phe Cys Lys Asp Ile Arg Trp Ser Leu Gly Asp Phe Gly Asp
                85                  90                  95

Ile Ile Met Gly Thr Asp Met Glu Gly Ile Gly Tyr Ser Lys Xaa Xaa
            100                 105                 110

Xaa Xaa Xaa Xaa Xaa Xaa Xaa Xaa Thr Asp Glu Lys Ala Gln Gln
        115                 120                 125

Arg Arg Lys Gln Trp Trp Asn Glu Ser Lys Ala Gln Ile Trp Thr Ala
    130                 135                 140

Met Met Tyr Ser Val Xaa Xaa Xaa Xaa Xaa Xaa Xaa Xaa Xaa Xaa
145                 150                 155                 160

Cys Xaa Xaa Xaa Xaa Xaa Xaa Xaa Glu Pro Gln Ile Tyr Arg Trp
            165                 170                 175
```

Ile Arg Glu Trp Gly Arg Asp Tyr Val Ser Glu Leu Pro Thr Glu Val
            180                 185                 190

Gln Lys Leu Lys Glu Lys Cys Xaa Xaa Xaa Xaa Xaa Xaa Xaa Xaa
            195                 200                 205

Xaa Xaa Cys Xaa Val Pro Pro Cys Gln Asn Ala Cys Lys Ser Tyr Asp
        210                 215                 220

Gln Trp Ile Thr Arg Lys Lys Asn Xaa Xaa Xaa Xaa Xaa Xaa Xaa Xaa
225                 230                 235                 240

Xaa Xaa Xaa Xaa Xaa Xaa Xaa Xaa Xaa Xaa Xaa Xaa Xaa Xaa Xaa
                245                 250                 255

Xaa Xaa Xaa Xaa Xaa Xaa Xaa Xaa Xaa Xaa Xaa Xaa Xaa Xaa Xaa
                260                 265                 270

Xaa Xaa Xaa Xaa Xaa Xaa Xaa Xaa Xaa Xaa Xaa Xaa Xaa Xaa Xaa
                275                 280                 285

Cys Xaa Cys
        290

(2) INFORMATION FOR SEQ ID NO:14:

(i) SEQUENCE CHARACTERISTICS:
        (A) LENGTH: 271 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO:14:

Cys Xaa Xaa Xaa Xaa Xaa Xaa Xaa Xaa Xaa Xaa Cys Xaa Xaa Xaa Xaa
1               5                   10                  15

Xaa Xaa Xaa Xaa Xaa Val Cys Ile Pro Asp Arg Arg Ile Gln Leu Cys
            20                  25                  30

Ile Val Asn Leu Xaa Xaa Xaa Xaa Xaa Xaa Xaa Xaa Xaa Xaa Xaa
            35                  40                  45

Xaa Xaa Xaa Xaa Xaa Xaa Xaa Xaa Xaa Xaa Xaa Xaa Xaa Xaa Xaa
        50                  55                  60

Xaa Xaa Xaa Xaa Xaa Xaa Xaa Xaa Lys Phe Cys Asn Asp Leu Lys Asn
65                  70                  75                  80

Ser Phe Leu Asp Tyr Gly His Leu Ala Met Gly Asn Asp Met Asp Phe
                85                  90                  95

Gly Gly Tyr Ser Thr Xaa Xaa Xaa Xaa Xaa Xaa Xaa Xaa Xaa Xaa Xaa
            100                 105                 110

Xaa Xaa Xaa Xaa Xaa Xaa Ser Glu His Lys Ile Lys Asn Phe Arg Lys
        115                 120                 125

Glu Trp Trp Asn Glu Phe Arg Glu Lys Leu Trp Glu Ala Met Leu Ser
130                 135                 140

Glu His Xaa Xaa Xaa Xaa Xaa Xaa Cys Xaa Xaa Xaa Xaa Xaa Xaa Glu
145                 150                 155                 160

Leu Gln Ile Thr Gln Trp Ile Lys Glu Trp His Gly Glu Phe Leu Leu
                165                 170                 175

```
Glu Arg Asp Asn Arg Ser Lys Leu Pro Lys Ser Lys Cys Xaa Xaa Xaa
                180                 185                 190

Xaa Xaa Xaa Xaa Xaa Cys Xaa Glu Lys Glu Cys Ile Asp Pro Cys Met
            195                 200                 205

Lys Tyr Arg Asp Trp Ile Ile Arg Ser Lys Phe Xaa Xaa Xaa Xaa Xaa
            210                 215                 220

Xaa Xaa Xaa Xaa Xaa Xaa Xaa Xaa Xaa Xaa Xaa Xaa Xaa Xaa Xaa Xaa
225                 230                 235                 240

Xaa Xaa Xaa Xaa Xaa Xaa Xaa Xaa Xaa Xaa Xaa Xaa Xaa Xaa Xaa Xaa
            245                 250                 255

Xaa Xaa Xaa Xaa Cys Xaa Xaa Xaa Xaa Xaa Xaa Xaa Cys Xaa Cys
            260                 265                 270
```

(2) INFORMATION FOR SEQ ID NO:15:

(i) SEQUENCE CHARACTERISTICS:
        (A) LENGTH: 277 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO:15:

```
Cys Xaa Xaa Xaa Xaa Xaa Xaa Xaa Xaa Xaa Xaa Xaa Xaa Cys Xaa
1               5                   10                  15

Xaa Xaa Xaa Xaa Xaa Xaa Xaa Xaa Xaa Val Cys Val Pro Pro Arg Arg
            20                  25                  30

Gln Glu Leu Cys Leu Gly Asn Ile Xaa Xaa Xaa Xaa Xaa Xaa Xaa Xaa
            35                  40                  45

Xaa Xaa Xaa Xaa Xaa Xaa Xaa Xaa Xaa Xaa Xaa Xaa Xaa Xaa Xaa Xaa
    50                  55                  60

Xaa Xaa Xaa Xaa Xaa Xaa Xaa Xaa Xaa Xaa Xaa Glu Val Cys Lys
65                  70                  75                  80

Ile Ile Asn Lys Thr Phe Ala Asp Ile Arg Asp Ile Ile Gly Gly Thr
            85                  90                  95

Asp Tyr Trp Asn Asp Leu Ser Asn Arg Xaa Xaa Xaa Xaa Xaa Xaa Xaa
            100                 105                 110

Xaa Xaa Xaa Xaa Xaa Xaa Xaa Xaa Asn Lys Lys Asn Asp Lys Leu Phe
            115                 120                 125

Arg Asp Glu Trp Trp Lys Val Ile Lys Lys Asp Val Trp Asn Val Ile
130                 135                 140

Ser Trp Phe Xaa Xaa Xaa Xaa Xaa Cys Xaa Xaa Xaa Xaa Xaa Xaa Xaa
145                 150                 155                 160

Ile Pro Gln Phe Phe Arg Trp Phe Ser Glu Trp Gly Asp Asp Tyr Cys
            165                 170                 175

Gln Asp Lys Thr Lys Met Ile Glu Thr Leu Lys Val Glu Cys Xaa Xaa
            180                 185                 190

Xaa Xaa Cys Xaa Asp Asp Asn Cys Lys Ser Lys Cys Asn Ser Tyr Lys
            195                 200                 205

Glu Trp Ile Ser Lys Lys Lys Lys Xaa Xaa Xaa Xaa Xaa Xaa Xaa Xaa
```

```
           210                 215                 220
Xaa Xaa Xaa Xaa Xaa Xaa Xaa Xaa Xaa X aa Xaa Xaa Xaa Xaa Xaa
225                 230                 235                 240

Xaa Xaa Xaa Xaa Xaa Xaa Xaa Xaa Xaa X aa Xaa Cys Xaa Xaa Xaa
            245                 250                 255

Xaa Xaa Xaa Xaa Xaa Xaa Xaa Xaa Xaa X aa Xaa Xaa Xaa Xaa Xaa
            260                 265                 270

Xaa Cys Xaa Xaa Cys
        275

(2) INFORMATION FOR SEQ ID NO:16:

(i) SEQUENCE CHARACTERISTICS:
        (A) LENGTH: 282 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO:16:

Cys Xaa Xaa Xaa Xaa Xaa Xaa Xaa Xaa X aa Xaa Xaa Cys Xaa Xaa
1               5                   10                  15

Xaa Xaa Xaa Xaa Xaa Xaa Xaa Xaa Xaa Val C ys Gly Pro Pro Arg Arg
            20                  25                  30

Gln Gln Leu Cys Leu Gly Tyr Ile Xaa Xaa X aa Xaa Xaa Xaa Xaa Xaa
            35                  40                  45

Xaa Xaa Xaa Xaa Xaa Xaa Xaa Xaa Xaa X aa Xaa Xaa Xaa Xaa Xaa
            50                  55                  60

Xaa Xaa Xaa Xaa Xaa Xaa Xaa Xaa Xaa X aa Xaa Lys Ile Cys Asn
65                  70                  75                  80

Ala Ile Leu Gly Ser Tyr Ala Asp Ile Gly A sp Ile Val Arg Gly Leu
            85                  90                  95

Asp Val Trp Arg Asp Ile Asn Thr Asn Xaa X aa Xaa Xaa Xaa Xaa Xaa
            100                 105                 110

Xaa Xaa Xaa Xaa Xaa Xaa Xaa Xaa Xaa L ys Lys Gln Asn Asp Asn
            115                 120                 125

Asn Glu Arg Asn Lys Trp Trp Glu Lys Gln A rg Asn Leu Ile Trp Ser
            130                 135                 140

Ser Met Val Lys His Ile Xaa Xaa Xaa X aa Cys Xaa Xaa Xaa Xaa
145                 150                 155                 160

Xaa Xaa Xaa Xaa Ile Pro Gln Phe Leu Arg T rp Leu Lys Glu Trp Gly
            165                 170                 175

Asp Glu Phe Cys Glu Glu Met Gly Thr Glu V al Lys Gln Leu Glu Lys
            180                 185                 190

Ile Cys Xaa Xaa Xaa Xaa Cys Xaa Glu Lys L ys Cys Lys Asn Ala Cys
            195                 200                 205

Ser Ser Tyr Glu Lys Trp Ile Lys Glu Arg L ys Asn Xaa Xaa Xaa Xaa
            210                 215                 220

Xaa Xaa Xaa Xaa Xaa Xaa Xaa Xaa Xaa X aa Xaa Xaa Xaa Xaa Xaa
225                 230                 235                 240
```

```
Xaa Xaa Xaa Xaa Xaa Xaa Xaa Xaa Xaa Xaa Xaa Xaa Xaa Xaa Xaa
                245                 250                 255

Xaa Xaa Cys Xaa Xaa Xaa Xaa Xaa Xaa Xaa Xaa Xaa Xaa Xaa
                260                 265                 270

Xaa Xaa Xaa Xaa Xaa Xaa Cys Xaa Xaa Cys
        275                 280
```

(2) INFORMATION FOR SEQ ID NO:17:

(i) SEQUENCE CHARACTERISTICS:
        (A) LENGTH: 324 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO:17:

```
Cys Xaa Xaa Xaa Xaa Xaa Xaa Xaa Xaa Xaa Cys Xaa Xaa Xaa Xaa
1                5                  10                  15

Xaa Xaa Xaa Xaa Xaa Xaa Xaa Ala Cys Ile Pro Pro Arg Arg Gln Lys
                20                  25                  30

Leu Cys Leu His Tyr Leu Xaa Xaa Xaa Xaa Xaa Xaa Xaa Xaa Xaa
            35                  40                  45

Xaa Xaa Xaa Xaa Xaa Xaa Xaa Xaa Xaa Xaa Xaa Xaa Xaa Xaa Xaa
            50                  55                  60

Xaa Xaa Xaa Xaa Xaa Xaa Xaa Xaa Xaa Xaa Xaa Xaa Xaa Xaa Xaa
65                  70                  75                  80

Xaa Xaa Xaa Xaa Xaa Xaa Xaa Xaa Xaa Asp Phe Lys Arg Gln Met Phe
                85                  90                  95

Tyr Thr Phe Ala Asp Tyr Arg Asp Ile Cys Leu Gly Thr Asp Ile Ser
                100                 105                 110

Ser Lys Lys Asp Thr Ser Xaa Xaa Xaa Xaa Xaa Xaa Xaa Xaa Xaa
            115                 120                 125

Xaa Xaa Xaa Xaa Xaa Lys Ile Ser Asn Ser Ile Arg Tyr Arg Lys Ser
            130                 135                 140

Trp Trp Glu Thr Asn Gly Pro Val Ile Trp Glu Gly Met Leu Cys Ala
145                 150                 155                 160

Leu Xaa Xaa Xaa Xaa Xaa Xaa Xaa Xaa Xaa Xaa Xaa Xaa Xaa Xaa
            165                 170                 175

Xaa Xaa Xaa Xaa Xaa Xaa Xaa Xaa Xaa Xaa Xaa Xaa Xaa Xaa Xaa
            180                 185                 190

Xaa Xaa Xaa Xaa Xaa Xaa Xaa Xaa Xaa Xaa Arg Pro Gln Phe Leu
            195                 200                 205

Arg Trp Leu Thr Glu Trp Gly Glu Asn Phe Cys Lys Glu Gln Lys Lys
210                 215                 220

Glu Tyr Lys Val Leu Leu Ala Lys Cys Xaa Xaa Xaa Xaa Xaa Xaa Xaa
225                 230                 235                 240

Xaa Xaa Xaa Xaa Cys Xaa Xaa Xaa Cys Val Ala Cys Lys Asp Gln Cys
            245                 250                 255
```

```
Lys Gln Tyr His Ser Trp Ile Gly Ile Trp Ile Asp Xaa Xaa Xaa Xaa
                260                 265                 270

Xaa Xaa Xaa Xaa Xaa Xaa Xaa Xaa Xaa Xaa Xaa Xaa Xaa Xaa Xaa
        275                 280                 285

Xaa Xaa Xaa Xaa Xaa Xaa Xaa Xaa Xaa Xaa Xaa Xaa Xaa Xaa Xaa
        290                 295                 300

Xaa Xaa Xaa Xaa Xaa Xaa Cys Xaa Xaa Xaa Xaa Xaa Xaa Xaa Cys
305                 310                 315                 320

Xaa Xaa Xaa Cys (2) INFORMATION FOR SEQ ID NO:18:

(i) SEQUENCE CHARACTERISTICS:
        (A) LENGTH: 362 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO:18:

Ala Cys Ala Pro Tyr Arg Arg Leu His Leu Cys Asp Tyr Asn Leu Xaa
1               5                   10                  15

Xaa Xaa Xaa Xaa Xaa Xaa Xaa Xaa Xaa Xaa Xaa Xaa Xaa Xaa Xaa
        20                  25                  30

Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Gln Leu Cys Thr Val Leu
        50                  55                  60

Ala Arg Ser Phe Ala Asp Ile Gly Asp Ile Val Arg Gly Lys Asp Leu
65                  70                  75                  80

Tyr Leu Gly Tyr Asp Asn Lys Xaa Xaa Xaa Xaa Xaa Xaa Xaa Xaa
                85                  90                  95

Xaa Xaa Xaa Xaa Xaa Xaa Xaa Xaa Xaa Xaa Xaa Xaa Xaa Xaa Xaa
        100                 105                 110

Xaa Xaa Xaa Xaa Xaa Xaa Xaa Xaa Xaa Xaa Xaa Lys Gly Gly Asp
        115                 120                 125

Phe Phe Gln Leu Arg Glu Asp Trp Trp Thr Ser Asn Arg Glu Thr Val
        130                 135                 140

Trp Lys Ala Leu Ile Cys His Ala Xaa Xaa Xaa Xaa Xaa Xaa Xaa
145                 150                 155                 160

Xaa Xaa Xaa Cys Xaa Xaa Xaa Xaa Xaa Xaa Xaa Xaa Xaa Xaa Xaa
            165                 170                 175

Xaa Xaa Xaa Xaa Xaa Xaa Xaa Xaa Xaa Val Pro Gln Tyr Leu
        180                 185                 190

Arg Trp Phe Glu Glu Trp Ala Glu Asp Phe Cys Arg Lys Lys Lys
        195                 200                 205

Lys Leu Glu Asn Leu Gln Lys Gln Cys Xaa Xaa Xaa Xaa Xaa Xaa Cys
        210                 215                 220

Xaa Xaa Xaa Xaa Xaa Xaa Xaa Xaa Xaa Xaa Xaa Xaa Xaa Xaa Cys
225                 230                 235                 240
```

```
Thr Asn Cys Ser Val Trp Cys Arg Met Tyr Glu Thr Trp Ile Asp Asn
                245                 250                 255

Gln Lys Lys Xaa Xaa Xaa Xaa Xaa Xaa Xaa Xaa Xaa Xaa Xaa
                260                 265                 270

Xaa Xaa Xaa Xaa Xaa Xaa Xaa Xaa Xaa Xaa Xaa Xaa Xaa Xaa
                275                 280             285

Xaa Xaa Xaa Xaa Xaa Xaa Xaa Xaa Xaa Xaa Xaa Xaa Xaa Xaa
    290                 295             300

Xaa Xaa Xaa Xaa Xaa Xaa Xaa Xaa Xaa Xaa Xaa Xaa Xaa Xaa
305             310                 315                 320

Xaa Xaa Xaa Xaa Xaa Xaa Xaa Cys Xaa Xaa Xaa Xaa Xaa Xaa Xaa
                325                 330                 335

Xaa Xaa Xaa Xaa Xaa Xaa Xaa Xaa Xaa Xaa Xaa Xaa Xaa Xaa
                340                 345             350

Xaa Xaa Xaa Xaa Xaa Xaa Cys Xaa Xaa Cys
    355                 360
```

(2) INFORMATION FOR SEQ ID NO:19:

(i) SEQUENCE CHARACTERISTICS:
      (A) LENGTH: 411 amino acids
      (B) TYPE: amino acid
      (C) STRANDEDNESS: single
      (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO:19:

```
Cys Xaa Xaa Xaa Xaa Xaa Xaa Xaa Xaa Xaa Xaa Xaa Xaa Xaa Xaa
1               5                   10                  15

Cys Xaa Xaa Xaa Xaa Xaa Xaa Xaa Xaa Xaa Xaa Xaa Xaa Xaa Xaa
                20                  25                  30

Ala Cys Ala Pro Tyr Arg Arg Leu His Val Cys Asp Gln Asn Leu Xaa
                35                  40                  45

Xaa Xaa Xaa Xaa Xaa Xaa Xaa Xaa Xaa Xaa Xaa Xaa Xaa Xaa
    50                  55                  60

Xaa Xaa Xaa Xaa Xaa Xaa Xaa Xaa Xaa Xaa Xaa Xaa Xaa Xaa Xaa
65                  70                  75                  80

Xaa Xaa Xaa Xaa Xaa Xaa Xaa Xaa Xaa Xaa Xaa Gln Ile Cys Thr
                85                  90                  95

Met Leu Ala Arg Ser Phe Ala Asp Ile Gly Asp Ile Val Arg Gly Arg
                100                 105                 110

Asp Leu Tyr Leu Gly Asn Pro Gln Glu Xaa Xaa Xaa Xaa Xaa Xaa
                115                 120                 125

Xaa Xaa Xaa Xaa Xaa Xaa Xaa Xaa Xaa Xaa Xaa Xaa Xaa Xaa
    130                 135                 140

Xaa Xaa Xaa Xaa Xaa Xaa Xaa Asn Asp Pro Glu Phe Phe Lys Leu Arg
145                 150                 155                 160

Glu Asp Trp Trp Thr Ala Asn Arg Glu Thr Val Trp Lys Ala Ile Thr
                165                 170                 175
```

-continued

```
Cys Asn Ala Xaa Xaa Xaa Xaa Xaa Xaa Xaa Xaa Cys Xaa Xaa Xaa
            180                 185                 190

Xaa Xaa Xaa Xaa Xaa Xaa Xaa Xaa Xaa Xaa Xaa Xaa Xaa Xaa Xaa
            195                 200                 205

Xaa Xaa Xaa Xaa Val Pro Gln Tyr Leu Arg Trp Phe Glu Glu Trp Ala
            210                 215                 220

Glu Asp Phe Cys Arg Lys Lys Asn Lys Lys Ile Lys Asp Val Lys Arg
225                 230                 235                 240

Asn Cys Xaa Xaa Xaa Xaa Xaa Xaa Xaa Xaa Xaa Xaa Xaa Cys Xaa
            245                 250                 255

Xaa Xaa Xaa Xaa Xaa Xaa Xaa Xaa Xaa Xaa Xaa Xaa Xaa Xaa Xaa
            260                 265                 270

Xaa Xaa Xaa Xaa Xaa Cys Ile Ser Cys Leu Tyr Ala Cys Asn Pro Tyr
            275                 280                 285

Val Asp Trp Ile Asn Asn Gln Lys Glu Xaa Xaa Xaa Xaa Xaa Xaa
            290                 295                 300

Xaa Xaa Xaa Xaa Xaa Xaa Xaa Xaa Xaa Xaa Xaa Xaa Xaa Xaa Xaa
305                 310                 315                 320

Xaa Xaa Xaa Xaa Xaa Xaa Xaa Xaa Xaa Xaa Xaa Xaa Xaa Xaa Xaa
            325                 330                 335

Xaa Xaa Xaa Xaa Xaa Xaa Xaa Xaa Xaa Xaa Xaa Xaa Xaa Xaa Xaa
            340                 345                 350

Xaa Xaa Xaa Xaa Xaa Xaa Xaa Xaa Xaa Xaa Xaa Xaa Xaa Cys Xaa
            355                 360                 365

Xaa Xaa Xaa Xaa Xaa Xaa Xaa Xaa Xaa Xaa Xaa Xaa Xaa Xaa Xaa
            370                 375                 380

Xaa Xaa Xaa Xaa Xaa Xaa Xaa Xaa Xaa Xaa Xaa Xaa Xaa Xaa Xaa
385                 390                 395                 400

Xaa Xaa Xaa Xaa Xaa Xaa Xaa Cys Xaa Xaa Cys
            405                 410
```

(2) INFORMATION FOR SEQ ID NO:20:

(i) SEQUENCE CHARACTERISTICS:
        (A) LENGTH: 411 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO:20:

```
Cys Xaa Xaa Xaa Xaa Xaa Xaa Xaa Xaa Xaa Xaa Xaa Xaa Xaa Xaa
1               5                   10                  15

Xaa Xaa Cys Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa
            35                  40                  45

Xaa Xaa Val Phe Leu Pro Pro Arg Arg Glu His Met Cys Thr Ser Asn
            50                  55                  60

Leu Xaa Xaa Xaa Xaa Xaa Xaa Xaa Xaa Xaa Xaa Xaa Xaa Xaa Xaa
```

```
                65                  70                  75                  80
Xaa Xaa Xaa Xaa Xaa Xaa Xaa Xaa Xaa Xaa Xaa Xaa Xaa Xaa Xaa Xaa
                    85                  90                  95

Xaa Xaa Xaa Xaa Xaa Xaa Xaa Xaa Xaa Xaa Xaa Xaa Xaa Xaa Xaa Xaa
                    100                 105                 110

Xaa Xaa Xaa Xaa Xaa Xaa Xaa Xaa Ala Met Cys Arg Ala Val Arg Tyr
                    115                 120                 125

Ser Phe Ala Asp Leu Gly Asp Ile Ile Arg Gly Arg Asp Met Trp Asp
                    130                 135                 140

Glu Asp Lys Ser Ser Xaa Xaa Xaa Xaa Xaa Xaa Xaa Xaa Xaa Xaa Xaa
145                 150                 155                 160

Xaa Xaa Xaa Xaa Xaa Xaa Xaa Xaa Xaa Xaa Xaa Xaa Xaa Xaa Xaa Xaa
                    165                 170                 175

Xaa Xaa Xaa Xaa Xaa Lys Lys Pro Ala Tyr Lys Lys Leu Arg Ala Asp
                    180                 185                 190

Trp Trp Glu Ala Asn Arg His Gln Val Trp Arg Ala Met Lys Cys Ala
                    195                 200                 205

Thr Xaa Xaa Xaa Xaa Cys Xaa Xaa Xaa Xaa Xaa Xaa Xaa Xaa Ile Pro
    210                 215                 220

Gln Arg Leu Arg Trp Met Thr Glu Trp Ala Glu Trp Tyr Cys Lys Ala
225                 230                 235                 240

Gln Ser Gln Glu Tyr Asp Lys Leu Lys Lys Ile Cys Xaa Xaa Xaa Xaa
                    245                 250                 255

Xaa Xaa Xaa Xaa Xaa Xaa Xaa Cys Xaa Xaa Xaa Xaa Xaa Xaa Cys Gly
                    260                 265                 270

Lys Cys Lys Ala Ala Cys Asp Lys Tyr Lys Glu Glu Ile Glu Lys Trp
                    275                 280                 285

Asn Glu Gln Trp Arg Lys Xaa Xaa Xaa Xaa Xaa Xaa Xaa Xaa Xaa Xaa
290                 295                 300

Xaa Xaa Xaa Xaa Xaa Xaa Xaa Xaa Xaa Xaa Xaa Xaa Xaa Xaa Xaa Xaa
305                 310                 315                 320

Xaa Xaa Xaa Xaa Xaa Xaa Xaa Xaa Xaa Xaa Xaa Xaa Xaa Xaa Xaa Xaa
                    325                 330                 335

Xaa Xaa Xaa Xaa Xaa Xaa Xaa Xaa Xaa Xaa Xaa Xaa Xaa Xaa Xaa Xaa
                    340                 345                 350

Xaa Xaa Xaa Xaa Xaa Xaa Xaa Xaa Xaa Xaa Xaa Xaa Xaa Xaa Xaa Cys
                    355                 360                 365

Xaa Xaa Xaa Xaa Xaa Xaa Xaa Cys Xaa Xaa Xaa Xaa Xaa Xaa Xaa Xaa
    370                 375                 380

Xaa Xaa Xaa Xaa Xaa Xaa Xaa Xaa Xaa Xaa Xaa Xaa Xaa Xaa Xaa Xaa
385                 390                 395                 400

Xaa Xaa Xaa Xaa Xaa Xaa Xaa Cys Xaa Xaa Cys
                    405                 410

(2) INFORMATION FOR SEQ ID NO:21:

(i) SEQUENCE CHARACTERISTICS:
        (A) LENGTH: 311 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO
```

(v) FRAGMENT TYPE: internal (vi) ORIGINAL SOURCE:

(xi) SEQUENCE DESCRIPTION: SEQ ID NO:21:

Cys Xaa Xaa Xaa Xaa Xaa Xaa Xaa Xaa Xaa Cys Xaa Xaa Xaa Xaa
 1               5                  10                  15

Xaa Xaa Xaa Xaa Xaa Ala Cys Met Pro Pro Arg Arg Gln Lys Leu
                20              25                  30

Cys Leu Tyr Tyr Ile Xaa Xaa Xaa Xaa Xaa Xaa Xaa Xaa Xaa Xaa
                35              40                  45

Xaa Xaa Xaa Xaa Xaa Xaa Xaa Xaa Xaa Xaa Xaa Xaa Xaa Xaa Xaa
 50                  55                  60

Xaa Xaa Xaa Xaa Xaa Xaa Xaa Xaa Xaa Xaa Xaa Xaa Xaa Xaa Xaa
 65                  70                  75                  80

Xaa Xaa Xaa Xaa Xaa Xaa Xaa Xaa Gln Phe Leu Arg Ser Met Met
                85                  90                  95

Tyr Thr Phe Gly Asp Tyr Arg Asp Ile Cys Leu Asn Thr Asp Ile Ser
                100                 105                 110

Lys Lys Gln Asn Asp Val Xaa Xaa Xaa Xaa Xaa Xaa Xaa Xaa Xaa
                115                 120                 125

Xaa Xaa Xaa Xaa Xaa Ser Lys Ser Pro Ser Gly Leu Ser Arg Gln Glu
 130                 135                 140

Trp Trp Lys Thr Asn Gly Pro Glu Ile Trp Lys Gly Met Leu Cys Ala
 145                 150                 155                 160

Leu Xaa Xaa Xaa Xaa Xaa Xaa Xaa Xaa Xaa Xaa Xaa Xaa Xaa Xaa
                165                 170                 175

Xaa Xaa Xaa Xaa Xaa Xaa Xaa Xaa Xaa Xaa Xaa Xaa Xaa Xaa Xaa
                180                 185                 190

Xaa Xaa Xaa Xaa Xaa Lys Pro Gln Phe Leu Arg Trp Met Ile Glu
                195                 200                 205

Trp Gly Glu Glu Phe Cys Ala Glu Arg Gln Lys Lys Glu Asn Ile Ile
 210                 215                 220

Lys Asp Ala Cys Xaa Xaa Xaa Xaa Xaa Xaa Xaa Xaa Cys Xaa Xaa Xaa
225                 230                 235                 240

Lys His Arg Cys Asn Gln Ala Cys Arg Ala Tyr Gln Glu Tyr Val Glu
                245                 250                 255

Asn Lys Lys Lys Xaa Xaa Xaa Xaa Xaa Xaa Xaa Xaa Xaa Xaa Xaa
                260                 265                 270

Xaa Xaa Xaa Xaa Xaa Xaa Xaa Xaa Xaa Xaa Xaa Xaa Xaa Xaa Xaa
                275                 280                 285

Xaa Xaa Xaa Xaa Xaa Xaa Xaa Xaa Xaa Xaa Xaa Xaa Xaa Xaa Cys
                290                 295                 300

Xaa Xaa Xaa Xaa Cys Xaa Cys
305                 310

(2) INFORMATION FOR SEQ ID NO:22:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (iii) HYPOTHETICAL: NO

```
        (iv) ANTI-SENSE: NO (v) FRAGMENT TYPE: N-terminal (vi) ORIGINAL SOURCE:

(xi) SEQUENCE DESCRIPTION: SEQ ID NO:22:

Pro Arg Arg Gln Xaa Leu Cys
  1               5

(2) INFORMATION FOR SEQ ID NO:23:

(i) SEQUENCE CHARACTERISTICS:
             (A) LENGTH: 20 base pairs
             (B) TYPE: nucleic acid
             (C) STRANDEDNESS: single
             (D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:23:

CCRAGRAGRC AARAAYTATG                                                       20

(2) INFORMATION FOR SEQ ID NO:24:

(i) SEQUENCE CHARACTERISTICS:
             (A) LENGTH: 20 base pairs
             (B) TYPE: nucleic acid
             (C) STRANDEDNESS: single
             (D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:24:

CCSMGSMGSC AGCAGYTSTG                                                       20

(2) INFORMATION FOR SEQ ID NO:25:

(i) SEQUENCE CHARACTERISTICS:
             (A) LENGTH: 7 amino acids
             (B) TYPE: amino acid
             (C) STRANDEDNESS: single
             (D) TOPOLOGY: linear (ii) MOLECULE TYPE: peptide (iii) HYPOTHETICAL: NO (iv) ANTI-SENSE: NO (v) FRAGMENT TYPE: N-terminal (vi) ORIGINAL SOURCE:

(xi) SEQUENCE DESCRIPTION: SEQ ID NO:25:
```

```
Phe Ala Asp Xaa Xaa Asp Ile
  1               5
```

(2) INFORMATION FOR SEQ ID NO:26:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:26:

```
TTTGCWGATW WWSGWGATAT                                          20
```

(2) INFORMATION FOR SEQ ID NO:27:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:27:

```
TTCGCSGATW WCSGSGACAT                                          20
```

(2) INFORMATION FOR SEQ ID NO:28:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: N-terminal (vi) ORIGINAL SOURCE:

(xi) SEQUENCE DESCRIPTION: SEQ ID NO:28:

```
Pro Gln Phe Xaa Arg Trp
  1               5
```

(2) INFORMATION FOR SEQ ID NO:29:

(i) SEQUENCE CHARACTERISTICS:
        (A) LENGTH: 18 base pairs
        (B) TYPE: nucleic acid

```
        (C) STRANDEDNESS: single
        (D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:29:

CCAWCKKARR AATTGWGG                                                   18

(2) INFORMATION FOR SEQ ID NO:30:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:30:

CCASCKGWAG AWCTGSGG                                                   18

(2) INFORMATION FOR SEQ ID NO:31:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: N-terminal (vi) ORIGINAL SOURCE:

(xi) SEQUENCE DESCRIPTION: SEQ ID NO:31:

Glu Trp Gly Xaa Xaa Xaa Cys
  1               5

(2) INFORMATION FOR SEQ ID NO:32:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO
```

(v) FRAGMENT TYPE:

(vi) ORIGINAL SOURCE:

(xi) SEQUENCE DESCRIPTION: SEQ ID NO:32:

CAAWAWTCWT CWCCCCATTC                                              20

(2) INFORMATION FOR SEQ ID NO:33:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:33:

CAGWASTCST CSCCCCACTC                                              20

(2) INFORMATION FOR SEQ ID NO:34:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:34:

ATCGATCAGC TGGGAAGAAA TACTTCATCT                                   30

(2) INFORMATION FOR SEQ ID NO:35:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:35:

ATCGATGGGC CCCGAAGTTT GTTCATTATT                                   30

(2) INFORMATION FOR SEQ ID NO:36:

-continued

```
    (i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:36:

TCTCGTCAGC TGACGATCTC TAGTGCTATT                                     30

(2) INFORMATION FOR SEQ ID NO:37:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:37:

ACGAGTGGGC CCTGTCACAA CTTCCTGAGT                                     30
```

BINDING DOMAINS FROM PLASMODIUM VIVAX AND PLASMODIUM FALCIPARUM ERYTHROCYTE BINDING PROTEINS

This application is a divisional of U.S. patent application Ser. No. 08/568,459, filed Dec. 7, 1995, now U.S. Pat. No. 5,849,306, which is a continuation of U.S. patent application Ser. No. 08/119,677, filed Sep. 10, 1993, abandoned.

BACKGROUND OF THE INVENTION

Malaria infects 200–400 million people each year causing 1–2 million deaths, thus remaining one of the most important infectious diseases in the world. Approximately 25 percent of all deaths of children in rural Africa between the ages of one and four years are caused by malaria. Due to the importance of the disease as a worldwide health problem, considerable effort is being expended to identify and develop malaria vaccines.

Malaria in humans is caused by four species of the parasite Plasmodium: *P. falciparum, P. vivax, P. knowlesi* and *P. malariae*. The major cause of malaria in humans if *P. falciparum* which infects 200 million to 400 million people every year, killing 1 to 4 million.

*P. vivax* (one of the four species infective to humans) cannot be cultured in vitro, as has been possible with *P. knowlesi* (a malarial strain found in old world monkeys which also invade human erythrocytes) and *P. falciparum*. Although *P. vivax* bears substantial phylogenetic similarity to *P. knowlesi*, the two species are different in many important respects. For example, *P. vivax* is not infective of many simian species and infection is poorly established in others, whereas *P. knowlesi* is poorly infective of humans while readily infecting many simian species.

The basis of various potential vaccines to combat malaria is appreciated through an understanding of the life cycle of the parasite. Infection in humans begins when young malarial parasites or "sporozoites" are injected into the bloodstream of a human by the mosquito. Following injection, the parasite localizes to liver cells. After approximately one week the parasites or "merozoites" are released into the bloodstream. The entry of the parasites into the bloodstream begins the "erythrocytic" phase. Each parasite enters the red blood cell in order to grow and develop. When the merozoite matures in the red blood cell, it is known as a trophozoite. The trophozoite undergoes several rounds of nuclear division (schizogony) until it ruptures the erythrocyte, releasing from 6 to 24 merozoites. After several asexual schizogonic cycles, some parasites, instead of becoming schizonts through asexual reproduction, develop into morphologically distinct forms known as "gametocytes" which are long-lived and undergo sexual development.

Sexual development of the malaria parasites involve the female or "macrogametocyte" and the male parasite or "microgametocyte." These gametocytes do not undergo any further development in humans. Upon ingestion of the gametocytes into the mosquito, the complicated sexual cycle begins in the midgut of the mosquito. The red blood cells disintegrate in the midgut of the mosquito after 10 to 20 minutes. The microgametocyte continues to develop through exflagellation and releases 8 highly flagellated microgametes. Fertilization occurs upon fusion of the microgamete and the macrogamete. The fertilized parasite is known as a zygote which develops into an "ookinete." The ookinete embeds in the midgut of the mosquito, transforming into an oocyst within which many small sporozoites form. Before embedding in the midgut, the ookinete must first penetrate the peritrophic membrane which apparently acts as a barrier for invasion of ingested parasites. When the oocyst ruptures the sporozoites migrate to the salivary gland of the mosquito via the hemolymph. Once in the saliva of the mosquito, the parasite can be injected into a host.

The erythrocytic stage of the Plasmodium life cycle is of special relevance to vaccine development because the clinical and pathologic features of malaria in the host are attributable to this stage. In *P. vivax*, and *P. knowlesi*, Duffy blood group determinants present on Duffy positive erythrocytes are essential for invasion of human erythrocytes (Miller et al., Science 189: 561–563, (1975); Miller et al., N. Engl. J. Med. 295: 302–304, (1976)). In *P. falciparum*, invasion of merozoites into erythrocytes appears to be dependent on binding to sialic acids on glycophorins on the erythrocyte (Miller, et al., J. Exp. Med. 146: 277–281, (1971); Pasvol, et al., Lancet. ii: 947–950 (1982); Pasvol, et al., Nature, 279: 64–66 (1982); Perkins, J. Exp. Med. 160: 788–798 (1984)). Studies with the monkey parasite *P. knowlesi* allow a clearer understanding of the multiple events that occur during invasion. It is likely that even though *P. vivax* and *P. falciparum* bind to the Duffy antigen and sialic acids respectively, they share common strategies of invasion with each other and with *P. knowlesi*.

In *P. knowlesi*, during invasion a merozoite first attaches to an erythrocyte on any surface of the merozoite, then reorients so that its apical end is in contact with the erythrocyte (Dvorak et al., Science 187: 748–750, (1975)). Both attachment and reorientation of merozoites occur equally well on Duffy positive and Duffy negative cells. A junction then forms between the apical end of the merozoite and the Duffy positive erythrocyte followed by vacuole formation and entry of the merozoite into the vacuole. Aikawa et al., J. Cell Biol. 77: 72–82 (1978). Junction formation and merozoite entry into the erythrocyte do not occur on Duffy negative cells (Miller et al., J. Exp. Med. 149: 172–184 (1979)), suggesting that a receptor specific for the Duffy determinant is involved in apical junction formation but not initial attachment.

The apical end of the merozoite is defined by the presence of three organelles: rhopteries, dense granules and micronemes. The rhopteries and dense granules release their contents at vacuole formation (Ladda et al., 1969; Aikawa et al., J. Cell Biol., 77: 72–82 (1978); Torn et al., Infection and Immunity 57: 3230–3233 (1989); Bannister and Dluzewski, Blood Cells 16: 257–292 (1990)). To date the function of the microneme is unknown. Nevertheless, the location of the micronemes suggest that they are involved in the invasion process. Duffy Antigen Binding Protein (DABP) and Sialic Acid Binding Protein (SABP) have been localized to the micronemes of *P. knowlesi* and *P. falciparum* respectively (Adams et al., Cell 63.: 141–153 (1990); Sim et al., Mol. Biochem. Parasitol. 51: 157–160. (1992)).

DABP and SABP are soluble proteins that appear in the culture supernatant after infected erythrocytes release merozoites. Immunochemical data indicate that DABP and SABP which are the respective ligands for the *P. vivax* and *P. falciparum* Duffy and sialic acid receptors on erythrocytes, possess specificities of binding which are identical either in soluble or membrane bound form.

DABP is a 135 kDa protein which binds specifically to Duffy blood group determinants (Wertheimer et al., Exp. Parasitol. 69: 340–350 (1989); Barnwell, et al., J. Exp. Med. 169: 1795–1802 (1989)). Thus, binding of DABP is specific to human Duffy positive erythrocytes. There are four major Duffy phenotypes for human erythrocytes: Fy(a), Fy(b), Fy(ab) and Fy(negative), as defined by the anti-Fy$^a$ and anti-Fy$^b$ sera (Hadley et al., In Red Cell Antigens and Antibodies, G. Garratty, ed. (Arlington,. Va.:American Association of Blood Banks) pp. 17–33 (1986)). DABP binds equally to both Fy(a) and Fy(b) erythrocytes which are equally susceptible to invasion by *P. vivax*; but not to Fy(negative) erythrocytes.

In the case of SABP, a 175 kDa protein, binding is specific to the glycophorin sialic acid residues on erythrocytes (Camus and Hadley, Science 230:553–556 (1985); Orlandi, et al., J. Cell Biol. 116:901–909 (1992)). Thus, neuraminidase treatment (which cleaves off sialic acid residues) render erythrocytes, immune to *P. falciparum* invasion.

The specificities of binding and correlation to invasion by the parasite thus indicate that DABP and SABP are the proteins of *P. vivax* and *P. falciparum* which interact with sialic acids and the Duffy antigen on the erythrocyte. The genes encoding both proteins have been cloned and the DNA and predicted protein sequences have been determined (B. Kim Lee Sim, et al., J. Cell Biol. 111. 1877–1884 (1990); Fang, X., et al., Mol. Biochem Parasitol. 44: 125–132 (1991)).

Despite considerable research efforts worldwide, because of the complexity of the Plasmodium parasite and its interaction with its host, it has not been possible to discover a satisfactory solution for prevention or abatement of the blood stage of malaria. Because malaria is a such a large worldwide health problem, there is a need for methods that abate the impact of this disease. The present invention provides effective preventive and therapeutic measures against Plasmodium invasion.

SUMMARY OF THE INVENTION

The present invention provides compositions comprising an isolated DABP binding domain polypeptides and/or isolated SABP binding domain polypeptides. The DABP binding domain polypeptides preferably comprise between about 200 and about 300 amino acid residues while the SABP binding domain polypeptides preferably comprises between about 200 and about 600 amino acid residues. A preferred DABP binding domain polypeptide has residues 1 to about 325 of the amino acid sequence found in SEQ ID NO:2. A preferred SABP binding domain polypeptide has residues 1 to about 616 of the amino acid sequence of SEQ ID NO:4.

The present invention also includes pharmaceutical compositions comprising a pharmaceutically acceptable carrier and an isolated DABP binding domain polypeptide in an amount sufficient to induce a protective immune response to *Plasmodium vivax* merozoites in an organism. In addition, isolated SABP binding domain polypeptide in an amount sufficient to induce a protective immune response to *Plasmodium falciparum* may be added to the pharmaceutical composition.

Also provided are pharmaceutical compositions comprising a pharmaceutically acceptable carrier and an isolated SABP binding domain polypeptide in an amount sufficient to induce a protective immune response to *Plasmodium falciparum* merozoites in an organism. In addition, isolated DABP binding domain polypeptide in an amount sufficient to induce a protective immune response to *Plasmodium vivax* may be added to the pharmaceutical composition.

Isolated polynucleotides which encode a DABP binding domain polypeptides or SABP binding domain polypeptides are also disclosed. In addition the present invention includes a recombinant cell comprising the polynucleotide encoding the DABP binding domain polypeptide.

The current invention further includes methods of inducing a protective immune response to *Plasmodium merozoites* in a patient. The methods comprise administering to the, patient an immunologically effective amount of a pharmaceutical composition comprising a pharmaceutically acceptable carrier and an isolated DABP binding domain polypeptide, an SABP binding domain polypeptide or a combination thereof.

The present disclosure also provides DNA sequences from additional *P. falciparum* genes in the erythrocyte binding ligand (EBL) family that have regions conserved with the *P. falciparum* 175 kD and *P. vivax* 135 kD binding proteins.

DEFINITIONS

As used herein a "DABP binding domain polypeptide" or a "SABP binding domain polypeptide" are polypeptides substantially identical (as defined below) to a sequence from the cysteine-rich, amino-terminal region of the Duffy antigen binding protein (DABP) or sialic acid binding protein (SABP), respectively. Such polypeptides are capable of binding either the Duffy antigen or sialic acid residues on glycophorin. In particular, DABP, binding domain polypeptides consist of amino acid residues substantially similar to a sequence of SABP within a binding domain from the N-terminal amino acid (residue 1) to about residue 325. SABP binding domain polypeptides consist of residues substantially similar to a sequence of DABP within a binding domain from the N-terminal amino acid (residue 1) to about residue 616.

The binding domain polypeptides encoded by the genes of the EBL family consist of those residues substantially identical to the sequence of the binding domains of DABP and SABP as defined above. The EBL family comprises sequences with substantial similarity to the conserved regions of the DABP and SABP. These include those sequences reported here as EBL-e1 (SEQ ID NO:5 and SEQ ID NO:6), E31a (SEQ ID NO:7 and SEQ ID No:8), EBL-e2 (SEQ ID NO:9 and SEQ ID NO:10) and Proj3 (SEQ ID NO:11 and SEQ ID NO:12).

The polypeptides of the invention can consist of the full length binding domain or a fragment thereof. Typically DABP binding domain polypeptides will consist of from about 50 to about 325 residues, preferably between about 75 and 300, more preferably between about 100 and about 250 residues. SABP binding domain polypeptides will consist of from about 50 to about 616 residues, preferably between about 75 and 300, more preferably between about 100 and about 250 residues.

Particularly preferred polypeptides of the invention are those within the binding domain that are conserved between SABP and the EBL family. Residues within these conserved domains are shown in FIG. 1, below.

Two polynucleotides or polypeptides are said to be "identical" if the sequence of nucleotides or amino acid residues in the two sequences is the same when aligned for maximum correspondence. Optimal alignment of sequences for comparison may be conducted by the local homology algorithm of Smith and Waterman *Adv. Appl. Math.* 2: 482.(1981), by the homology alignment algorithm of Needleman and Wunsch *J. Mol. Biol.* 48:443 (1970), by the search for similarity method of Pearson and Lipman *Proc. Natl. Acad. Sci.* (U.S.A.) 85: 2444 (1988), by computerized implementations of these algorithms (GAP, BESTFIT, FASTA, and TFASTA in the Wisconsin Genetics Software Package, Genetics Computer Group, 575 Science: Dr., Madison, Wis.), or by inspection. These references are incorporated herein by reference.

The term "substantial identity" means that a polypeptide comprises a sequence that has at least 80% sequence identity, preferably 90%, more preferably 95% or more, compared to a reference sequence over a comparison window of about 20 residues to about 600 residues—typically about 50 to about 500 residues usually about 250 to 300 residues. The values of percent identity are determined using the programs above. Particularly preferred peptides of the present invention comprise a sequence in which at least 70% of the cysteine residues conserved in DABP and SABP are present. Additionally, the peptide will comprise a sequence in which at least 50% of the Tryptophan residues conserved in DABP and SABP are present. The term substantial similarity is also specifically defined here with respect to those amino acid residues found to be conserved between DABP, SABP and the sequences of the EBL family. These conserved amino acids consist prominently of tryptophan and cysteine residues conserved among all sequences reported here. In addition the conserved amino acid residues include phenylalanine residues which may be substituted with tyrosine. These amino acid residues may be determined to be conserved after the sequences have been aligned using methods outlined above by someone skilled in the art.

Another indication that polypeptide sequences are substantially identical is if one protein is immunologically reactive with antibodies raised against the other protein. Thus, the polypeptides of the invention include polypeptides immunologically reactive with antibodies raised against the SABP binding domain, the DABP binding domain or raised against the conserved regions of the EBL family.

Another indication that nucleotide sequences are substantially identical is if two molecules hybridize to each other under stringent conditions. Stringent conditions are sequence dependent and will be different in different circumstances. Generally, stringent conditions are selected to be about 5° C. lower than the thermal melting point (Tm) for the specific sequence at a defined ionic strength and pH. The Tm is the temperature (under defined ionic strength and pH) at which 50% of the target sequence hybridizes to a perfectly matched probe. Typically, stringent conditions will be those in which the salt concentration is at least about 0.02 molar at pH 7 and the temperature is at least about 60° C.

The phrases "isolated" or "biologically pure" refer to material which is substantially or essentially free from components which normally accompany it as found in its native state. Thus, the binding domain polypeptides of this invention do not contain materials normally associated with their in situ environment, e.g., other proteins from a merozoite membrane. However, even where a protein has been isolated to a homogenous or dominant band by PAGE, there can be trace contaminants in the range of 5–10% of native protein which co-purify with the desired protein. Isolated polypeptides of this invention do not contain such endogenous co-purified protein.

Protein purity or homogeneity may be indicated by a number of means well known in the art, such as polyacrylamide gel electrophoresis of a protein sample, followed by visualization upon staining. For certain purposes high resolution will be needed and HPLC or a similar means for purification utilized.

The term "residue" refers to an amino acid (D or L) or amino acid mimetic incorporated in a oligopeptide by an amide bond or amide bond mimetic. An amide bond mimetic of the invention includes peptide backbone modifications well known to those skilled in the art.

BRIEF DESCRIPTION OF THE DRAWINGS

Figures 1, 1A:
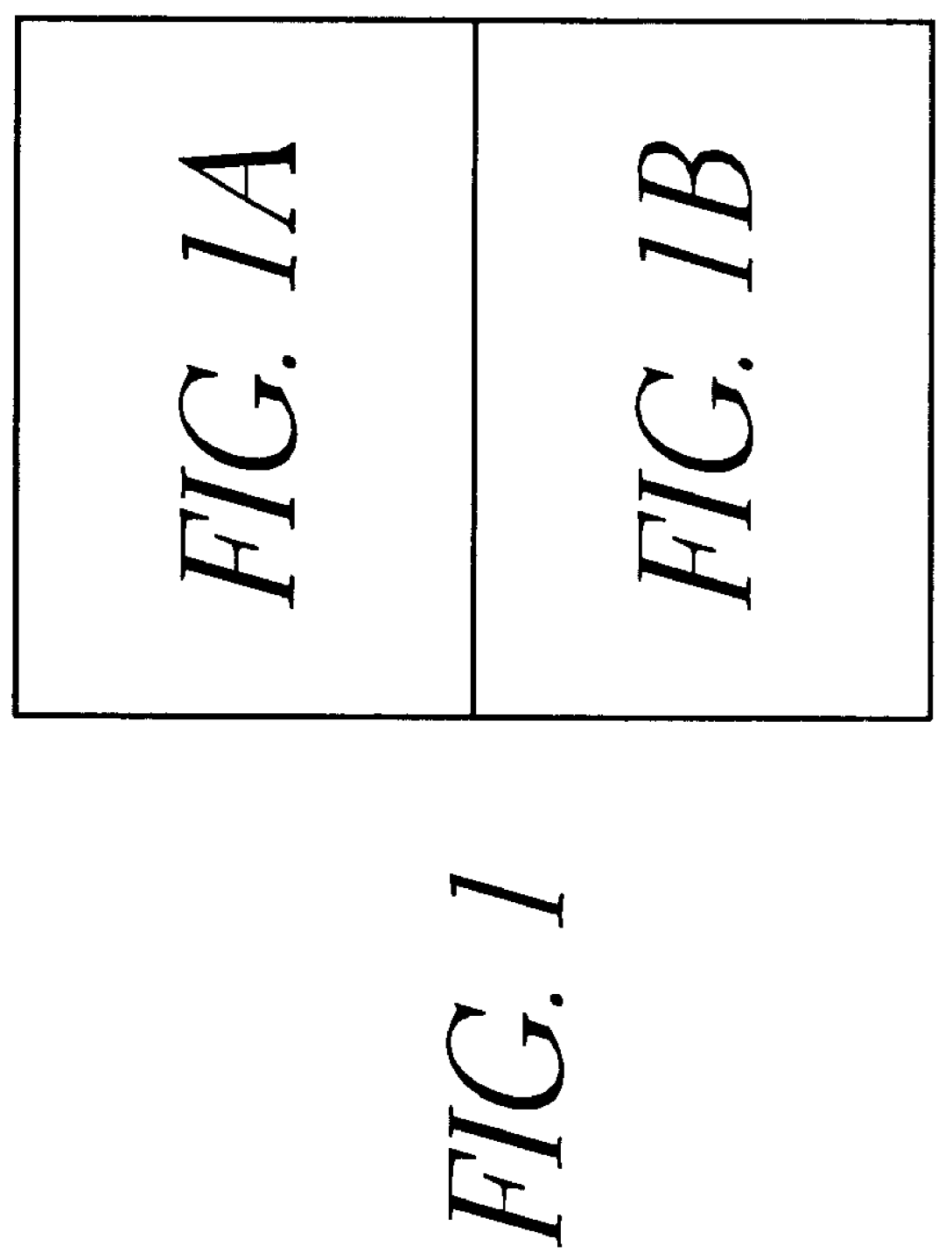

FIGS. 1A–1B represent an alignment of the predicted amino acid sequences of the DABP binding domain (SEQ ID NO:13 (Vivax), the two homologous SABP domains (SABP F1 (SEQ ID NO:14) and SABP F2 (SEQ ID NO:15) and the sequenced members of the EBL gene family (ebl-e1 (SEQ ID NO:16), E31a (SEQ ID NO:17), EBL-e2 (SEQ ID NO:18) and the three homologous Proj3 domains.

FIG. 3 shows primers (SEQ ID NO:24, SEQ ID NO:24, SEQ ID NO:26, SEQ ID NO:27, SEQ ID NO:29, SEQ ID NO:30, SEQ ID NO:32 and SEQ ID NO:33) useful for isolating sequences encoding the conserved motifs of the invention.

DESCRIPTION OF THE PREFERRED EMBODIMENT

Figure 2:
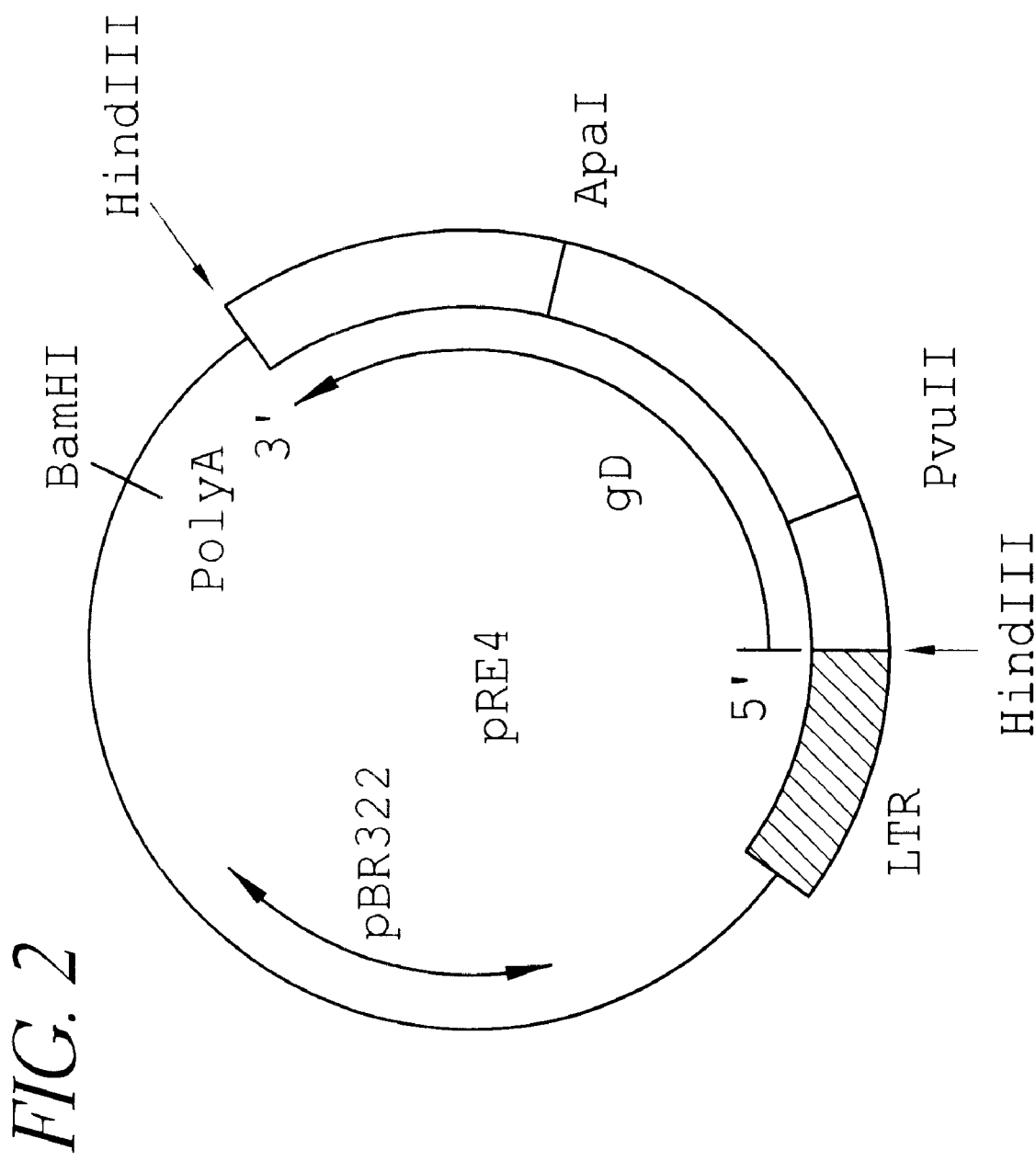
FIG. 2 represents a schematic of the pRE4 cloning vector.

The binding of merozoites and schizonts to erythrocytes is mediated by specific binding proteins on the surface of the merozoite or schizont and is necessary for erythrocyte invasion. In the case of *P. falciparum*, this binding involves specific interaction between sialic acid glycophorin residues on the erythrocyte and the sialic acid binding protein (SABP) on the surface of the merozoite or schizont. The ability of purified SABP to bind erythrocytes with chemically or enzymatically altered sialic acid residues paralleled the ability of *P. falciparum* to invade these erythrocytes. Furthermore, sialic acid deficient erythrocytes neither bind SABP nor support invasion by *P. falciparum*. The DNA encoding SABP from *P. falciparum* has also been cloned and sequenced.

In *P. vivax*, specific binding to the erythrocytes involves interaction between the Duffy blood group antigen on the erythrocyte and the Duffy antigen binding protein (DABP) on the merozoite. Duffy binding proteins were defined biologically as those soluble proteins that appear in the culture supernatant after the infected erythrocytes release merozoites which bind to human Duffy positive, but not to human Duffy negative erythrocytes. It has been shown that binding of the *P. vivax* DABP protein to Duffy positive erythrocytes is blocked by antisera to the Duffy blood group determinants. Purified Duffy blood group antigens also block the binding to erythrocytes. DABP has also been shown to bind Duffy blood group determinants on Western blots.

Duffy positive blood group determinants on human erythrocytes are essential for invasion of human erythrocytes by *Plasmodium vivax*. Both attachment and reorientation of *P. vivax* merozoites occur equally well on Duffy positive and negative erythrocytes. A junction then forms between the apical end of the merozoite and the Duffy-positive erythrocyte, followed by vacuole formation and entry of the merozoite into the vacuole. Junction formation and merozoite entry into the erythrocyte do not occur on Duffy negative cells, suggesting that the receptor specific for the Duffy determinant is involved in apical junction formation but not initial attachment. The DNA sequences encoding the DABP from *P. vivax* and *P. knowlesi* have been cloned and sequenced.

*P. vivax* red cell invasion has an absolute requirement for the Duffy blood group antigen. Isolates of *P. falciparum*, however, vary in their dependency on sialic acid for invasion. Certain *P. falciparum* clones have been developed which invade sialic acid deficient erythrocytes at normal rates. This suggests that certain strains of *P. falciparum* can interact with other ligands on the erythrocyte and so may possess multiple erythrocyte binding proteins with differing specificities.

A basis for the present invention is the discovery of the binding domains in both DABP and SABP. Comparison of the predicted protein sequences of DABP and SABP reveals an amino-terminal, cysteine-rich region in both proteins with a high degree of similarity between the two proteins. The amino-terminal, cysteine-rich region of DABP contains about 325 amino acids, whereas the amino-terminal, cysteine-rich region of SABP contains about 616 amino acids. This is due to an apparent duplication of the amino-terminal, cysteine-rich region in the SABP protein. The cysteine residues are conserved between the two regions of SABP and DABP, as are the amino acids surrounding the cysteine residues and a number of aromatic amino acid residues in this region. The amino-terminal cysteine-rich region and another cysteine-rich region near the carboxyl-terminus show the most similarity between the DABP and SABP proteins. The region of the amino acid sequence between these two cysteine-rich regions show only limited similarity between DABP and SABP.

Other *P. falciparum* open reading frames and genes with regions that have substantial identity to binding domains of SABP and DABP have been identified. Multiple copies of these sequences exist in the parasite genome, indicating their important activity in host-parasite interactions. A family of these sequences (the EBL family) have been cloned from chromosome 7 subsegment libraries that were constructed during genetic studies of the chloroquine resistance locus (Wellems et. al., *PNAS* 88: 3382–3386 (1991)). Alignment of EBL sequences identified domains highly conserved with the *P. falciparum* 175 kD protein; these conserved domains have in turn been used to identify genes (ebl-e1, ebl-e2) one of which (ebl-e1) resides on chromosome 13. Genetic linkage studies have placed this gene within a region of chromosome 13 that affects invasion of malarial parasites in human red blood cells (Wellems et al., *Cell* 49:633–642 (1987)).

Southern hybridization experiments using probes from these open reading frames have indicated that additional copies of these conserved sequences are located elsewhere in the genome. The largest of the open reading frames on chromosome 7 is 8 kilobases and contains four tandem repeats homologous to the N-terminal, cysteine-rich unit of SABP and DABP.

FIG. 1 represents an alignment of the EBL family with the DABP binding domain (SEQ ID NO:13) and two homologous regions of SABP (F1 (SEQ ID NO:14) and F2 (SEQ ID NO:15). The EBL family is divided into two sub-families to achieve optimal alignment. Conserved cysteine residues are shown in bold face and conserved aromatic residues are underlined.

The polypeptides of the invention can be used to raise monoclonal antibodies specific for the binding domains of SABP, DABP or the conserved regions in the EBL gene family. The antibodies can be used for diagnosis of malarial infection or as therapeutic agents to inhibit binding of merozoites to erythrocytes. The production of monoclonal antibodies against a desired antigen is well known to those of skill in the art and is not reviewed in detail here.

The multitude of techniques available to those skilled in the art for production and manipulation of various immunoglobulin molecules can thus be readily applied to inhibit binding. As used herein, the terms "immunoglobulin" and "antibody" refer to a protein consisting of one or more polypeptides substantially encoded by immunoglobulin genes. Immunoglobulins may exist in a variety of forms besides antibodies, including for example, Fv, Fab, and F(ab)$_2$, as well as in single chains. For a general review of immunoglobulin structure and function see, *Fundamental Immunology*, 2d Ed., W. E. Paul ed., Ravens Press, N.Y., (1989).

Antibodies which bind polypeptides of the invention may be produced by a variety of means. The production of non-human monoclonal antibodies, e.g., murine, lagomorpha, equine, etc., is well known and may be accomplished by, for example, immunizing the animal with a preparation containing the polypeptide. Antibody-producing cells obtained from the immunized animals are immortalized and screened, or screened first for the production of antibody which inhibits binding between and meroxoites and erythrocytes and then immortalized. For a discussion of general procedures of monoclonal antibody production see Harlow and Lane, Antibodies, *A Laboratory Manual* Cold Spring Harbor Publications, N.Y. (1988).

Thus, the present invention allows targeting of protective immune responses or monoclonal antibodies to sequences in the binding domains that are conserved between SABP, DABP and encoded regions of the EBL family. Identification of the binding regions of these proteins facilitates vaccine development because it allows for a focus of effort upon the functional elements of the large molecules. The particular sequences within the binding regions refine the target to critical regions that have been conserved during evolution, and are thus preferred for use as vaccines against the parasite.

The genes of the EBL family (which have not previously been sequenced) can be used as markers to detect the presence of the *P. falciparum* parasite in patients. This can be accomplished by means well known to practitioners in the art using tissue or blood from symptomatic patients in PCR reactions with oligonucleotides complementary to portions of the genes of the EBL family. Furthermore, sequencing the EBL family provides a means for skilled practitioners to generate defined probes to be used as genetic markers in a variety of applications.

Figures 3, 3A:
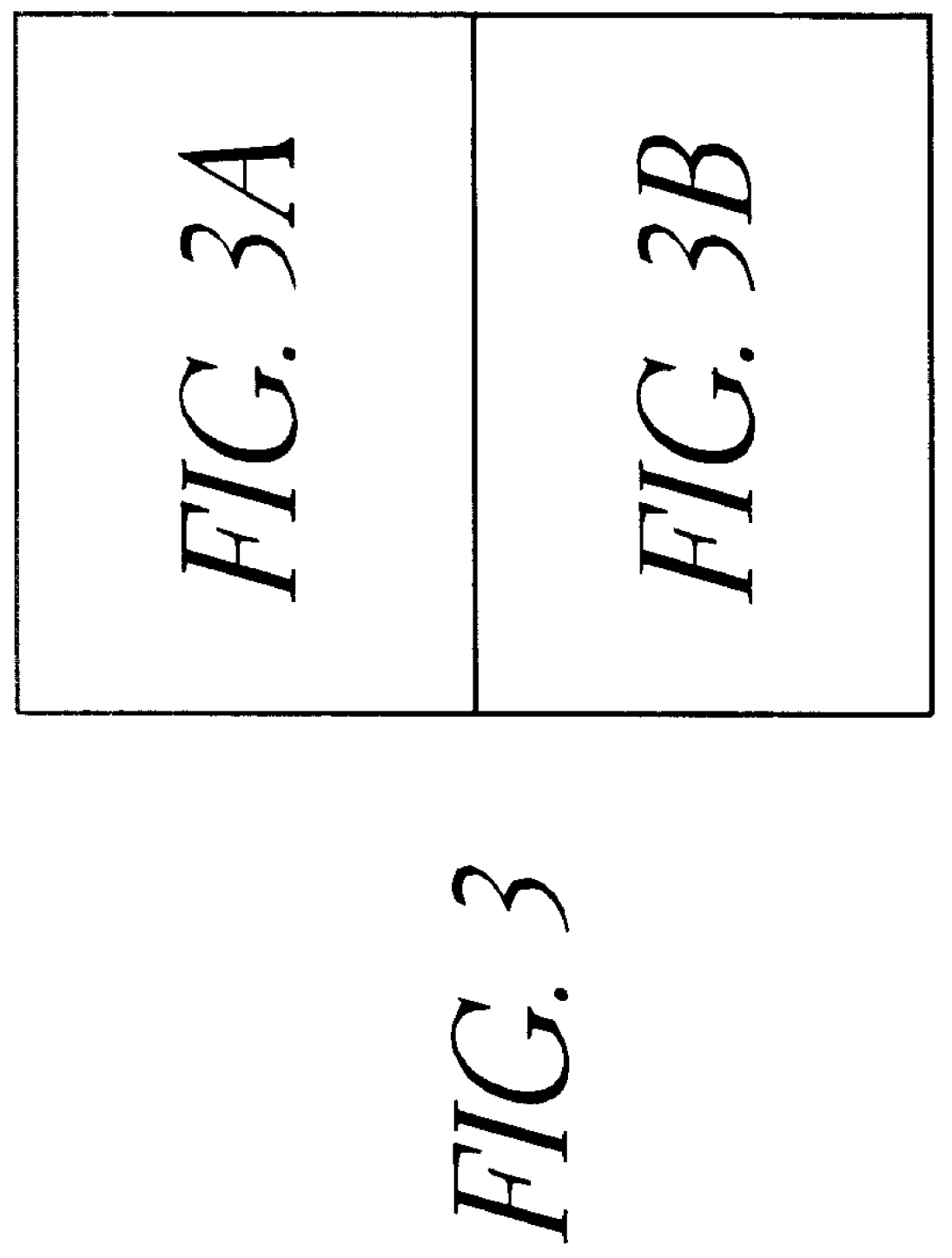

Additionally, the present invention defines a conserved motif present in, but not restricted to other members of the subphylum Apicomplexa which participates in host parasite interaction. This motif can be identified in *Plasmodium* species and other parasitic protozoa by the polymerase chain reaction using the synthetic oligonucleotide primers shown in FIG. 3 (SEQ ID NO:23, SEQ ID NO:24, SEQ ID NO:26, SEQ ID NO:27, SEQ ID NO:29, SEQ ID NO:30, SEQ ID NO:32 and SEQ ID NO:33). PCR methods are described in detail below. These primers are designed from regions in the conserved motif showing the highest degree of conservation among DABP, SABP and the EBL family. FIG. 3 shows these regions and the consensus amino acid sequences derived from them (SEQ ID NO:22, SEQ ID NO:5, SEQ ID NO:28, and SEQ ID NO:31).

A. General Methods

Much of the nomenclature and general laboratory procedures required in this application can be found in Sambrook, et al., Molecular Cloning *A Laboratory Manual* (2nd Ed.), Vol. 1–3, Cold Spring Harbor Laboratory, Cold Spring Harbor, N.Y., 1989. The manual is hereinafter referred to as "Sambrook, et al."

B. Methods for Isolating DNA Encoding SABP, DABP and EBL Binding Regions

The nucleic acid compositions of this invention, whether RNA, cDNA, genomic DNA, or a hybrid of the various combinations, may be isolated from natural sources or may be synthesized in vitro. The nucleic acids claimed may be present in transformed or transfected whole cells, in a transformed or transfected cell lysate, or in a partially purified or substantially pure form.

Techniques for nucleic acid manipulation of genes encoding the binding domains of the invention, such as subcloning nucleic acid sequences encoding polypeptides into expression vectors, labelling probes, DNA hybridization, and the like are described generally in Sambrook et al., incorporated herein by reference.

Recombinant DNA techniques can be used to produce the binding domain polypeptides. In general, the DNA encoding the SABP and DABP binding domains are first cloned or isolated in a form suitable for ligation into an expression vector. After ligation, the vectors containing the DNA fragments or inserts are introduced into a suitable host cell for expression of the recombinant binding domains. The polypeptides are then isolated from the host cells.

There are various methods of isolating the DNA sequences encoding the SABP, DABP and EBL binding domains. Typically, the DNA is isolated from a genomic or cDNA library using labelled oligonucleotide probes specific for sequences in the DNA. Restriction endonuclease digestion of genomic DNA or cDNA containing the appropriate genes can be used to isolate the DNA encoding the binding domains of these proteins. Since the DNA sequences of the SABP and DABP genes are known, a panel of restriction endonucleases can be constructed to give cleavage of the DNA in the desired regions. After restriction endonuclease digestion, DNA encoding SABP binding domain or DABP binding domain is identified by its ability to hybridize with nucleic acid probes, for example on Southern blots, and these DNA regions are isolated by standard methods familiar to those of skill in the art. See Sambrook, et al.

The polymerase chain reaction can also be used to prepare DABP, SABP and EBL binding domain DNA. Polymerase chain reaction technology (PCR) is used to amplify nucleic acid sequences of the DABP and SABP binding domains directly from mRNA, from cDNA, and from genomic libraries or cDNA libraries. The primers shown in FIG. 3 are particularly preferred for this process.

Appropriate primers and probes for amplifying the SABP and DABP binding region DNA s are generated from analysis of the DNA sequences. In brief, oligonucleotide primers complementary to the two 3' borders of the DNA region to be amplified are synthesized. The polymerase chain reaction is then carried out using the two primers. See *PCR Protocols: A Guide to Methods and Applications.* (Innis, M, Gelfand, D., Sninsky, J. and White, T., eds.), Academic Press, San Diego (1990). Primers can be selected to amplify the entire DABP regions or to amplify smaller segments of the DABP and SABP binding domains, as desired.

Oligonucleotides for use as probes are chemically synthesized according to the solid phase phosphoramidite triester method first described by Beaucage, S. L. and Caruthers, M. H., 1981, Tetrahedron Letts., 22(20):1859–1862 using an automated synthesizer, as described in Needham-VanDevanter, D. R., et al. 1984, Nucleic Acids Res., 12:6159–6168. Purification of oligonucleotides is by either native acrylamide gel electrophoresis or by anion-exchange HPLC as described in Pearson, J. D. and Regnier, F. E., 1983, J. Chrom., 255:137–149.

The sequence of the synthetic oligonucleotides can be verified using the chemical degradation method of Maxam, A. M. and Gilbert, 1980, in W., Grossman,. L. and Moldave, D., eds. Academic Press, New York, Methods in Enzymology, 65:499–560.

Other methods known to those of skill in the art may also be used to isolate DNA encoding all or part of the SABP or DABP binding domains. See Sambrook, et al.

C. Expression of DABP, SABP and EBL Binding Domain Polypeptides

Once the binding domain DNAs are isolated and cloned, one may express the desired polypeptides in a recombinantly engineered cell such as bacteria, yeast, insect (especially employing baculoviral vectors), and mammalian cells. It is expected that those of skill in the art are knowledgeable in the numerous expression systems available for expression of the DNA encoding the DABP and SABP binding domains. No attempt to describe in detail the various methods known for the expression of proteins in prokaryotes or eukaryotes will be made.

In brief summary, the expression of natural or synthetic nucleic acids encoding binding domains will typically be achieved by operably linking the DNA or cDNA to a promoter (which is either constitutive or inducible), followed by incorporation into an expression vector. The vectors can be suitable for replication and-integration in either prokaryotes or eukaryotes. Typical expression vectors contain transcription and translation terminators, initiation sequences, and promoters useful for regulation of the expression of the DNA encoding the binding domains. To obtain high level expression of a cloned gene, it is desirable to construct expression plasmids which contain, at the minimum, a strong promoter to direct transcription, a ribosome binding site for translational initiation, and a transcription/translation terminator.

1. Expression in Prokaryotes

Examples of regulatory regions suitable for this purpose in *E. coli* are the promoter and operator region of the *E. coli* tryptophan biosynthetic pathway as described by Yanofsky, C., 1984, J. Bacteriol., 158:1018–1024 and the leftward promoter of phage lambda ($P_L$) as described by Herskowitz, I. and Hagen, D., 1980, Ann. Rev. Genet., 14:399–445. The inclusion of selection markers in DNA vectors transformed in *E. coli* is also useful. Examples of such markers include genes specifying resistance to ampicillin, tetracycline, or chloramphenicol. See Sambrook et al. for details concerning selection markers for use in *E. coli*.

The vector is selected to allow introduction into the appropriate host cell. Bacterial vectors are typically of plasmid or phage origin. Appropriate bacterial cells are infected with phage vector particles or transfected with naked phage vector DNA. If a plasmid vector is used, the bacterial cells are transfected with the plasmid vector DNA.

Expression systems for expressing the DABP and SABP binding domains are available using *E. coli*, Bacillus sp. (Palva, I et al., 1983, Gene 22:229–235; Mosbach, K. et al. Nature, 302:543–545)) and Salmonella. *E. coli* systems are preferred.

The binding domain polypeptides produced by prokaryote cells may not necessarily fold properly. During purification from *E. coli*, the expressed polypeptides may first be denatured and then renatured. This can be accomplished by solubilizing the bacterially produced proteins in a chaotropic agent such as guanidine HCl and reducing all the cysteine residues with a reducing agent such as beta-mercaptoethanol. The polypeptides are then renatured, either by slow dialysis or by gel filtration. U.S. Pat. No. 4,511,503.

Detection of the expressed antigen is achieved by methods known in the art as radioimmunoassays, Western blotting techniques or immunoprecipitation. Purification from *E. coli* can be achieved following procedures described in U.S. Pat. No. 4,511,503.

2. Synthesis of SABP, DABP and EBL Binding Domains in Eukaryotes

A variety of eukaryotic expression systems such as yeast, insect cell lines and mammalian cells, are known to those of skill in the art. As explained briefly below, the DABP and SABP binding domains may also be expressed in these eukaryotic systems.

a. Expression in Yeast

Synthesis of heterologous proteins in yeast is well known and described. *Methods in Yeast Genetics,* Sherman, F., et al., Cold Spring Harbor Laboratory, (1982) is a well recognized work describing the various methods available to produce the binding domains in yeast.

Examples of promoters for use in yeast include GAL1,10 (Johnson, M., and Davies, R. W., 1984, Mol. and Cell. Biol., 4:1440–1448) ADH2 (Russell, D., et al. 1983, J. Biol. Chem., 258:2674–2682), PH05 (EMBO J. 6:675–680, 1982), and MFαl (Herskowitz, I. and Oshima, Y., 1982, in The Molecular Biology of the Yeast Saccharomyces, (eds. Strathern, J. N. Jones, E. W., and Broach, J. R., Cold Spring Harbor Lab., Cold Spring Harbor, N.Y., pp. 181–209. A multicopy plasmid with a selective marker such as Leu-2, URA-3, Trp-1, and His-3 is also desirable.

A number of yeast expression plasmids like YEp6, YEp13, YEp4 can be used as vectors. A gene of interest can be fused to any of the promoters in various yeast vectors. The above-mentioned plasmids have been fully described in the literature (Botstein, et al., 1979, Gene, 8:17–24; Broach, et al., 1979, Gene, 8:121–133).

Two procedures are used in transforming yeast cells. In one case, yeast cells are first converted into protoplasts using zymolyase, lyticase or glusulase, followed by addition of DNA and polyethylene glycol (PEG). The PEG-treated protoplasts are then regenerated in a 3% agar medium under selective conditions. Details of this procedure are given in the papers by J. D. Beggs, 1978, Nature (London), 275:104–109; and Hinnen, A., et al., 1978, Proc. Natl. Acad. Sci. USA, 75:1929–1933. The second procedure does not involve removal of the cell wall. Instead the cells are treated with lithium chloride or acetate and PEG and put on selective plates (Ito, H., et al., 1983, J. Bact., 153:163–168).

The binding domains can be isolated from yeast by lysing the cells and applying standard protein isolation techniques to the lysates. The monitoring of the purification process can be accomplished by using Western blot techniques or radioimmunoassays of other standard immunoassay techniques.

b. Expression in Mammalian and Insect Cell Cultures

Illustrative of cell cultures useful for the production of the binding,domains are cells of insect or mammalian origin. Mammalian cell systems often will be in the form of monolayers of cells although mammalian cell suspensions may also be used. Illustrative examples of mammalian cell lines include VERO and HeLa cells, Chinese hamster ovary (CHO) cell lines, W138, BHK, Cos-7 or MDCK cell lines.

As indicated above, the vector, e.g., a plasmid, which is used to transform the host cell, preferably contains DNA sequences to initiate transcription and sequences to control the translation of the antigen gene sequence. These sequences are referred to as expression control sequences. When the host cell is of insect or mammalian origin illustrative expression control sequences are obtained from the SV-40 promoter (Science, 222:524–527, 1983), the CMV I.E. Promoter (Proc. Natl. Acad. Sci. 81:659–663, 1984) or the metallothionein promoter (Nature 296:39–42, 1982). The cloning vector containing the expression control sequences is cleaved using restriction enzymes and adjusted in size as necessary or desirable and ligated with DNA coding for the SABP or DABP polypeptides by means well known in the art.

As with yeast, when higher animal host cells are employed, polyadenlyation or transcription terminator sequences from known mammalian genes need to be incorporated into the vector. An example of a terminator sequence is the polyadenlyation sequence from the bovine growth hormone gene. Sequences for accurate splicing of the transcript may also be included. An example of a splicing sequence is the VPl intron from SV40 (Sprague, J. et al., 1983, J. Virol. 45: 773–781).

Additionally, gene sequences to control replication in the host cell may be incorporated into the vector such as those found in bovine papilloma virus type-vectors. Saveria-Campo, M., 1985, "Bovine Papilloma virus DNA a Eukaryotic Cloning Vector" in DNA Cloning Vol. II a Practical Approach Ed. D. M. Glover, IRL Press, Arlington, Va. pp. 213–238.

The host cells are competent or rendered competent for transformation by various means. There are several well-known methods of introducing DNA into animal cells. These include: calcium phosphate precipitation, fusion of the recipient cells with bacterial protoplasts containing the DNA, treatment of the recipient cells with liposomes containing the DNA, DEAE dextran, electroporation and microinjection of the DNA directly into the cells.

The transformed cells are cultured by means well known in the art. Biochemical Methods in Cell Culture and Virology, Kuchler, R. J., Dowden, Hutchinson and Ross, Inc., (1977). The expressed DABP and SABP binding domain polypeptides are isolated from cells grown as suspensions or as monolayers. The latter are recovered by well known mechanical, chemical or enzymatic means.

c. Expression in Recombinant Vaccinia Virus-or Adenovirus-infected Cells

In addition to use in recombinant expression systems, the isolated binding domain DNA sequences can also be used to transform viruses that transfect host cells in the patient. Live attenuated viruses, such as vaccinia or adenovirus, are convenient alternatives for vaccines because they are inexpensive to produce and are easily transported and administered. Vaccinia vectors and methods useful in immunization protocols are described, for example, in U.S. Pat. No. 4,722,848, incorporated herein by reference.

Suitable viruses for use in the present invention include, but are not limited to, pox viruses, such as canarypox and cowpox viruses, and vaccinia viruses, alpha viruses, adenoviruses, and other animal viruses. The recombinant viruses can be produced by methods well known in the art, for example, using homologous recombination or ligating two plasmids. A recombinant canarypox or cowpox virus can be made, for example, by inserting the DNA's encoding the DABP and SABP binding domain polypeptides into plasmids so that they are flanked by viral sequences on both sides. The DNA's encoding the binding domains are then inserted into the virus genome through homologous recombination.

A recombinant adenovirus can be produced, for example, by ligating together two plasmids each containing about 50% of the viral sequence and the DNA sequence encoding erythrocyte binding domain polypeptide. Recombinant RNA viruses such as the alpha virus can be made via a CDNA intermediate using methods known in the art.

In the case of vaccinia virus (for example, strain WR), the DNA sequence encoding the binding domains can be inserted in the genome by a number of methods including homologous recombination using a transfer vector, pTKgpt-OFIS as described in Kaslow, et. al., *Science* 252:1310–1313 (1991), which is incorporated herein by reference.

Alternately the DNA encoding the SABP and DABP binding domains may be inserted into another plasmid designed for producing recombinant vaccinia, such as pGS62, Langford, C. L., et al., 198.6, *Mol. Cell. Biol.* 6:3191–3199. This plasmid consists of a cloning site for insertion of foreign genes, the P7.5 promoter of vaccinia to direct synthesis of the inserted gene, and the vaccinia TK gene flanking both ends of the foreign gene.

Confirmation of production of recombinant virus can be achieved by DNA hybridization using CDNA encoding the DABP and SABP binding domain polypeptides and by immunodetection techniques using antibodies specific for the expressed binding domain polypeptides. Virus stocks may be prepared by infection of cells such as HELA S3 spinner cells and harvesting of virus progeny.

The recombinant virus of the present invention can be used to induce anti-SABP and anti-DABP binding domain antibodies in mammals, such as mice or humans. In addition, the recombinant virus can be used to produce the SABP and DABP binding domains by infecting host cells in vitro, which in turn express the polypeptide (see section on expression of SABP and DABP binding domains in eukaryotic cells, above).

The present invention also relates to host cells infected with the recombinant virus. The host cells of the present invention are preferably mammalian, such as BSC-1 cells. Host cells infected with the recombinant virus express the DABP and SABP binding domains on their cell surfaces. In addition, membrane extracts of the infected cells induce protective antibodies when used to inoculate or boost previously inoculated mammals.

D. Purification of the SABP, DABP and EBL Binding Domain Polypeptides

The binding domain polypeptides produced by recombinant DNA technology may be purified by standard techniques well known to those of skill in the art. Recombinantly produced binding domain polypeptides can be directly expressed or expressed as a fusion protein. The protein is then purified by a combination of cell lysis (e.g., sonication) and affinity chromatography. For fusion products, subsequent digestion of the fusion protein with an appropriate proteolytic enzyme release the desired SABP and DABP binding domains.

The polypeptides of this invention may be purified to substantial purity by standard techniques well known in the art, including selective precipitation with such substances as ammonium sulfate, column chromatography, immunopurification methods, and others. See, for instance, R. Scopes, *Protein Purification: Principles and Practice*, Springer-Verlag: New York (1982), incorporated herein by reference.

E. Production of Binding Domains by Protein Chemistry Techniques

The polypeptides of the invention can be synthetically prepared in a wide variety of ways. For instance polypeptides of relatively short size, can be synthesized in solution or on a solid support in accordance with conventional techniques. Various automatic synthesizers are commercially available and can be used in accordance with known protocols. See, for example, Stewart and Young, *Solid Phase Peptide Synthesis,* 2d. ed., Pierce Chemical Co. (1984).

Alternatively, purified and isolated SABP, DABP or EBL family proteins may be treated with proteolytic enzymes in order to produce the binding domain polypeptides. For example, recombinant DABP and SABP proteins may be used for this purpose. The DABP and SABP protein sequence may then be analyzed to select proteolytic enzymes to be used to generate polypeptides containing desired regions of the DABP and SABP binding domain. The desired polypeptides are then purified by using standard techniques for protein and peptide purification. For a review of standard techniques see, *Methods in Enzymology*, "Guide to Protein Purification", M. Deutscher, ed. Vol. 182 (1990), pages 619–626, which is incorporated herein by reference.

F. Modification of Nucleic Acid and Polypeptide Sequences

The nucleotide sequences used to transfect the host cells used for production of recombinant binding domain polypeptides can be modified according to standard techniques to yield binding domain polypeptides, with a variety of desired properties. The binding domain polypeptides of the present invention can be readily designed and manufactured utilizing various recombinant DNA techniques well known to those skilled in the art. For example, the binding domain polypeptides can vary from the naturally-occurring sequence at the primary structure level by amino acid insertions, substitutions, deletions, and the like. These modifications can be used in a number of combinations to produce the final modified protein chain.

The amino acid sequence variants can be prepared with various objectives in mind, including facilitating purification and preparation of the recombinant polypeptides. The modified polypeptides are also useful for modifying plasma half-life, improving therapeutic efficacy, and lessening the severity or occurrence of side effects during therapeutic use. The amino acid sequence variants are usually predetermined variants not found in nature but exhibit the same immunogenic activity as naturally occurring polypeptides. For instance, polypeptide fragments comprising only a portion (usually at least about 60–80%, typically 90–95%) of the primary structure may be produced. For use as vaccines, polypeptide fragments are typically preferred so long as at least one epitope capable of eliciting production of blocking antibodies remains.

In general, modifications of the sequences encoding the binding domain polypeptides may be readily accomplished by a variety of well-known techniques, such as site-directed mutagenesis (see, Giliman and Smith, *Gene* 8:81–97 (1979) and Roberts, S. et al., *Nature* 328:731–734 (1987)). One of ordinary skill will appreciate that the effect of many mutations is difficult to predict. Thus, most modifications are evaluated by routine screening in a suitable assay for the desired characteristic. For instance, changes in the immunological character of the polypeptide can be detected by an appropriate competitive binding assay. Modifications of other properties such as redox or thermal stability, hydrophobicity, susceptibility to proteolysis, or the tendency to aggregate are all assayed according to standard techniques.

G. Diagnostic and Screening Assays

The polypeptides of the invention can be used in diagnostic applications for the detection of merozoites in a biological sample. The presence of parasites can be detected using several well recognized specific binding assays based on immunological results. (See U.S. Pat. Nos. 4,366,241; 4,376,110; 4,517,288; and 4,837,168, which are hereby incorporated by reference.) For instance, labeled monoclonal antibodies to polypeptides of the invention can be used to detect merozoites in a biological sample. Alternatively, labelled polypeptides of the invention can be used to detect the presence of antibodies to SABP or DABP in a biological sample. For a review of the general procedures in diagnostic immunoassays, see also *Basic and Clinical Immunology* 7th Edition (D. Stites and A. Terr ed.) 1991, which is hereby incorporated by reference.

In addition, modified polypeptides, antibodies or other compounds capable of inhibiting the interaction between SABP or DABP and erythrocytes can be assayed for biological activity. For instance, polypeptides can be recombinantly expressed on the surface of cells and the ability of the cells to bind erythrocytes can be measured as described below. Alternatively, peptides or antibodies can tested for the ability to inhibit binding between erythrocytes and merozoites or SABP and DABP.

Cell-free assays can also be used to measure binding of DABP or SABP polypeptides to isolated Duffy antigen or glycophorin polypeptides. For instance, the erythrocyte proteins can be immobilized on a solid surface and binding of labelled SABP or DABP polypeptides can be measured.

Many assay formats employ labelled assay components. The labelling systems can be in a variety of forms. The label may be coupled directly or indirectly to the desired component of the assay according to methods well known in the art. A wide variety of labels may be used. The component may be labelled by any one of several methods. The most common method of detection is the use of autoradiography with $^3$H, $^{125}$I, $^{35}$S, $^{14}$C, or $^{32}$p labelled compounds or the like. Non-radioactive labels include ligands which bind to labelled antibodies, fluorophores, chemiluminescent agents, enzymes, and antibodies which can serve as specific binding pair members for a labelled ligand. The choice of label depends on sensitivity required, ease of conjugation with the compound, stability requirements, and available instrumentation.

In addition, the polypeptides of the invention can be assayed using animal models, well known to those of skill in the art. For *P. falciparum* the in vivo models include Aotus sp. monkeys or chimpanzees; for *P. vivax* the in vivo models include Saimiri monkeys.

H. Pharmaceutical Compositions Comprising Binding Domain Polypeptides

The polypeptides of the invention are useful in therapeutic and prophylactic applications for the treatment of malaria. Pharmaceutical compositions of the invention are suitable for use in a variety of drug delivery systems. Suitable formulations for use in the present invention are found in *Remington's Pharmaceutical Sciences*, Mack Publishing Company, Philadelphia, Pa., 17th ed. (1985), which is incorporated herein by reference. For a brief review of methods for drug delivery, see, Langer, *Science* 249:1 527–1533 (1990), which is incorporated herein by reference.

The polypeptides of the present invention can be used in pharmaceutical and vaccine compositions that are useful for administration to mammals, particularly humans. The polypeptides can be administered together in certain circumstances, e.g. where infection by both *P. falciparum* and *P. vivax* is likely. Thus, a single pharmaceutical composition can be used for the treatment or prophylaxis of malaria caused by both parasites.

The compositions are suitable for single administrations or a series of administrations. When given as a series, inoculations subsequent to the initial administration are given to boost the immune response and are typically referred to as booster inoculations.

The pharmaceutical compositions of the invention are intended for parenteral, topical, oral or local administration. Preferably, the pharmaceutical compositions are administered parenterally, e.g., intravenously, subcutaneously, intradermally, or intramuscularly. Thus, the invention provides compositions for parenteral administration that comprise a solution of the agents described above dissolved or suspended in an acceptable carrier, preferably an aqueous carrier. A variety of aqueous carriers may be used, e.g., water, buffered water, 0.4% saline, 0.3% glycine, hyaluronic acid and the like. These compositions may be sterilized by conventional, well known sterilization techniques, or may be sterile filtered. The resulting aqueous solutions may be packaged for use as is, or lyophilized, the lyophilized preparation being combined with a sterile solution prior to administration. The compositions may contain pharmaceutically acceptable auxiliary substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, triethanolamine oleate, etc.

For solid compositions, conventional nontoxic solid carriers may be used which include, for example, pharmaceutical grades of mannitol, lactose, starch, magnesium stearate, sodium saccharin, talcum, cellulose, glucose, sucrose, magnesium carbonate, and the like. For oral administration, a pharmaceutically acceptable nontoxic composition is formed by incorporating any of the normally employed excipients, such as those carriers previously listed, and generally 10–95% of active ingredient and more preferably at a concentration of 25%–75%.

For aerosol administration, the polypeptides are preferably supplied in finely divided form along with a surfactant and propellant. The surfactant must, of course, be nontoxic, and preferably soluble in the propellant. Representative of such agents are the esters or partial esters of fatty acids containing from 6 to 22 carbon atoms, such as caproic, octanoic, lauric, palmitic, stearic, linoleic, linolenic, olesteric and oleic acids with an aliphatic polyhydric alcohol or its cyclic anhydride. Mixed esters, such as mixed or natural glycerides may be employed. A carrier can also be included, as desired, as with, e.g., lecithin for intranasal delivery.

In certain embodiments patients with malaria may be treated with SABP or DABP polypeptides or other specific blocking agents (e.g. monoclonal antibodies) that prevent binding of *Plasmodium merozoites* and schizonts to the erythrocyte surface.

The amount administered to the patient will vary depending upon what is being administered, the state of the patient and the manner of administration. In therapeutic applications, compositions are administered to a patient already suffering from malaria in an amount sufficient to inhibit spread of the parasite through erythrocytes and thus cure or at least partially arrest the symptoms of the disease and its complications. An amount adequate to accomplish this is defined as "therapeutically effective dose." Amounts effective for this use will depend on the severity of the disease and the weight and general state of the patient. But will generally be in the range of about 1 mg to about 5 gm per day, preferably about 100 mg per day, for a 70 kg patient.

Alternatively, the polypeptides of the invention can be used prophylactically as vaccines. The vaccines of the invention contain as an active ingredient an immunogenically effective amount of the binding domain polypeptide or of a recombinant virus as described herein. The immune response may include the generation of antibodies; activation of cytotoxic T lymphocytes (CTL) against cells presenting peptides derived from the peptides encoded by the SABP, DABP or EBL sequences of the present invention, or other mechanisms well known in the art. See e.g. Paul *Fundamental Immunology Second Edition* published by Raven press New York (incorporated herein by reference) for a description of immune response. Useful carriers are well known in the art, and include, for example, thyroglobulin, albumins such as human serum albumin, tetanus toxoid, polyamino acids such as poly(D-lysine:D-glutamic acid), influenza, hepatitis B virus core protein, hepatitis B virus recombinant vaccine. The vaccines can also contain a physiologically tolerable (acceptable) diluent such as water, phosphate buffered saline, or saline, and further typically include an adjuvant. Adjuvants such as incomplete Freund's adjuvant, aluminum phosphate, aluminum hydroxide, or alum are materials well known in the art.

The DNA or RNA encoding the SABP or DABP binding domains and the EBL gene family motifs may be introduced into patients to obtain an immune response to the polypeptides which the nucleic acid encodes. Wolff et. al., *Science* 247: 1465–1468 (1990) which is incorporated herein by reference describes the use of nucleic acids to produce expression of the genes which the nucleic acids encode.

Vaccine compositions containing the polypeptides, nucleic acids or viruses of the invention are administered to a patient to elicit a protective immune response against the polypeptide. A "protective immune response" is one which prevents or inhibits the spread of the parasite through erythrocytes and thus at least partially prevent the symptoms of the disease and its complications. An amount sufficient to accomplish this is defined as an "immunogenically effective dose." Amounts effective for this use will depend on the composition, the manner of administration, the weight and general state of health of the patient, and the judgment of the prescribing physician. For peptide compositions, the general range for the initial immunization (that is for therapeutic or prophylactic administration) is from about 100 μg to about 1 gm of peptide for a 70 kg patient, followed by boosting dosages of from about 100 μg to about 1 gm of the polypeptide pursuant to a boosting regimen over weeks to months depending upon the patient's response and condition e.g. by measuring levels of parasite in the patient's blood. For nucleic acids, typically 30–1,000 μg of nucleic acid is injected into a 7.0 Kg patient, more typically about 50–∥g of nucleic acid is injected into a 70 Kg patient followed by boosting doses as appropriate.

The following example is offered by way of illustration, not by way of limitation.

EXAMPLE

Identification of the Amino-terminal, Cysteine-rich Region of SABP and DABP as Binding Domains for Erythrocytes 1. Expression of the SABP Binding Domain Polypeptide on the Surface of Cos Cells To demonstrate that the amino-terminal, cysteine-rich region of the SABP protein is the sialic acid binding region, this region of the protein was expressed on the surface of mammalian Cos cells in vitro. This DNA sequence is from position 1 to position 1848 of the SABP DNA sequence (SEQ ID NO:3). Polymerase chain reaction technology (PCR) was used to amplify this region of the SABP DNA directly from the cloned gene.

Sequences corresponding to restriction endonuclease sites for PvuII or ApaI were incorporated into the oligonucleotide sequence of the probes used in PCR amplification in order to facilitate insertion of the PCR-amplified regions into the pRE4 vector (see below). The specific oligonucleotides, 5'-ATCGATCAGCTGGGAAGAAATACTTCATCT-3' (SEQ ID NO:34) and 5'-ATCGATGGGCCCCGAAGTTTGTTCATTATT-3' (SEQ ID NO:35) were synthesized. These oligonucleotides were used as primers to PCR-amplify the region of the DNA sequence encoding the cysteine-rich amino terminal region of the SABP protein.

PCR conditions were based on the standard described in Saiki, et al., Science 239: 487–491 (1988). Template DNA was provided from cloned fragments of the gene encoding SABP which had been spliced and re-cloned as a single open-reading frame piece.

The vector, pRE4, used for expression in Cos cells is shown in FIG. 1. The vector has an SV40 origin of replication, an ampicillin resistance marker and the Herpes simplex virus glycoprotein D gene (HSV glyd) cloned downstream of the Rous sarcoma virus long terminal repeats (RSV LTR). Part of the extracellular domain of the HSV glyd gene was excised using the PvuII and ApaI sites in HSV glyd.

As described above, the PCR oligonucleotide primers contained the PvuII or ApaI restriction sites. The PCR-amplified DNA fragments obtained above were digested with the restriction enzymes PvuII and ApaI and cloned into the PvuII and ApaI sites of the vector pRE4. These constructs were designed to express regions of the SABP protein as chimeric proteins with the signal sequence of HSV glyd at the N-terminal end and the transmembrane and cytoplasmic domain of HSV glyd at the C-terminal end. The signal sequence of HSV glyd targets these chimeric proteins to the surface of Cos cells and the transmembrane segment of HSV glyd anchors these chimeric proteins to the Cos cell surface.

Mammalian Cos cells were transfected with the pRE4 constructs containing the PCR-amplified SABP DNA regions, by calcium phosphate precipitation according to standard techniques.

2. Expression of the DABP Binding Domain Polypeptide on the Surface of Cos Cells To demonstrate that the amino-terminal, cysteine-rich region of the DABP protein is the binding domain, this region was expressed on the surface of Cos cells. This region of the DNA sequence from position 1–975 was first PCR-amplified (SEQ ID NO:1).

Sequences corresponding to restriction endonuclease sites for PvuII or ApaI were incorporated into the oligonucleotide probes used for PCR amplification in order to facilitate subsequent insertion of the amplified DNA into the pRE4 vector, as described above. The oligonucleotides, 5'-TCTCGTCAGCTGACGATCTCTAGTGCTATT-3' (SEQ ID NO:36) and 5'-ACGAGTGGGCCCTGTCACAACTTCCTGAGT-3' (SEQ ID NO:37) were synthesized. These oligonucleotides were used as primers to amplify the region of the DABP DNA sequence encoding the cysteine-rich, amino-terminal region of the DABP protein directly from the cloned DABP gene, using the same conditions described above.

The same pRE4 vector described above in the section on expression of SABP regions in Cos cells was also used as a vector for the DABP DNA regions.

3. Binding Studies with Erythrocytes

To demonstrate their ability to bind human erythrocytes, the transfected Cos cells expressing binding domains from DABP and SABP were incubated with erythrocytes for two hours at 37° C. in culture media (DMEM/10% FBS). The non-adherent erythrocytes were removed with five washes of phosphate-buffered saline and the bound erythrocytes were observed by light microscopy. Cos cells expressing the amino terminal, cysteine-rich SABP polypeptides on their surface bound untreated human erythrocytes, but did not bind neuraminidase treated erythrocytes, that is, erythrocytes which lack sialic acid residues on their surface (data not shown). Cos cells expressing other regions of the SABP protein on their surface did not bind human erythrocytes (data not shown). These results identified the amino-terminal, cysteine-rich region of SABP as the erythrocyte binding domain and indicated that the binding of Cos cells expressing these regions to human erythrocytes is specific. Furthermore, the binding of the expressed region to erythrocytes is identical to the binding pattern seen for the authentic SABP-175 molecule upon binding to erythrocytes.

Similarly, Cos cells expressing the amino-terminal cysteine-rich region of DABP on their surface bound Duffy-positive human erythrocytes, but did not bind Duffy-negative human erythrocytes, that is erythrocytes which lack the Duffy blood group antigen (data not shown). Cos cells expressing other regions of the DABP protein on their surface did not bind human erythrocytes (data not shown). These results identified the amino-terminal cysteine rich region of DABP as the erythrocyte binding domain and indicated that the binding of the Cos cells was specific.

What is claimed is:

1. An isolated nucleotide sequence encoding a cysteine-rich binding domain polypeptide derived from the *P. falciparum* 175 kDa sialic acid binding protein of SEQ ID NO:4, wherein said nucleotide sequence encodes a cysteine-rich binding domain polypeptide of about 50 to about 616 residues comprising cysteine residues that are in substantially similar relative positions as positions of cysteine residues in an amino acid sequence of a *P. vivax* Duffy Antigen binding protein of SEQ ID NO: 2.

2. The nucleic acid sequence of claim 1, wherein the nucleic acid sequence encodes a cysteine-rich binding domain polypeptide having between about 200 and about 600 amino acid residues.

3. The nucleic acid sequence of claim 1, wherein the nucleic acid sequence encodes a cysteine-rich binding domain polypeptide having the amino acid sequence of residues 158 to 739 of SEQ ID NO. 4.

4. The nucleic acid sequence of claim 1, wherein the nucleic acid sequence encodes a cysteine-rich binding domain polypeptide having the amino acid sequence of residues 158 to 427 of SEQ ID NO:4.

5. The nucleic acid sequence of claim 1, wherein the nucleic acid sequence encodes a cysteine-rich binding domain polypeptide having the amino acid sequence of residues 462 to 739 of SEQ ID NO:4.

6. The nucleic acid sequence of claim 1, wherein the nucleic acid sequence is derived from the nucleotide sequence of SEQ ID NO:3.

7. The nucleic acid sequence of claim 1, wherein said cysteine-rich binding domain polypeptide comprises a sequence of amino acid residues in which at least 70% of cysteine residues conserved in the *P. falciparum* sialic acid binding protein of SEQ ID NO:4 and the *P. vivax* Duffy antigen binding protein of SEQ ID NO:2 are present.

8. A pharmaceutical composition comprising a pharmaceutically acceptable carrier and a nucleic acid sequence encoding a cysteine-rich binding domain polypeptide derived from the *P. falciparum* 175 kDa sialic acid binding protein of SEQ ID NO: 4, wherein said nucleic acid sequence encodes an amino acid sequence of about 50 to about 616 residues comprising cysteine residues that are in substantially similar relative positions as positions of cysteine residues in an amino acid sequence of a *P. vivax* Duffy Antigen binding protein of SEQ ID NO: 2.

9. The pharmaceutical composition of claim 8, wherein the nucleic acid sequence encodes a cysteine-rich binding domain polypeptide having between about 200 and about 600 amino acid residues.

10. The pharmaceutical composition of claim 8, wherein the nucleic acid sequence encodes a cysteine-rich binding domain polypeptide having the amino acid sequence of residues 158 to 739 of SEQ ID NO.4.

11. The pharmaceutical composition of claim 8, wherein the nucleic acid sequence encodes a cysteine-rich binding domain polypeptide having the amino acid sequence of residues 158 to 427 of SEQ ID NO:4.

12. The pharmaceutical composition of claim 8, wherein the nucleic acid sequence encodes a cysteine-rich binding domain polypeptide having the amino acid sequence of residues 462 to 739 of SEQ ID NO:4.

13. The pharmaceutical composition of claim 8, wherein the nucleic acid sequence is derived from the nucleotide sequence of SEQ ID NO:3.

14. The pharmaceutical composition of claim 8, wherein said cysteine-rich binding domain polypeptide comprises a sequence of amino acid residues in which at least 70% of cysteine residues conserved in the *P. falciparum* sialic acid binding protein of SEQ ID NO:4 and the *P. vivax* Duffy antigen binding protein of SEQ ID NO:2 are present.

15. A method of inducing a partially protective immune response to *Plasmodium falciparum* merozoites in a patient, the method comprising administration to the patient of a pharmaceutical composition comprising a pharmaceutically acceptable carrier and a nucleic acid sequence encoding an isolated cysteine-rich binding domain polypeptide derived from a *P. falciparum* 175 kDa sialic acid binding protein of SEQ ID NO:4, wherein the nucleic acid sequence encodes an amino acid sequence of about 50 to about 616 residues comprising cysteine residues that are in substantially similar relative positions as positions of cysteine residues in an amino acid sequence of a Duffy Antigen binding protein of *P. vivax* of SEQ ID NO:2.

16. The method of claim 15, wherein the patient is a human.

17. A method of inducing a partially protective immune response to *Plasmodium falciparum* merozoites in a patient, the method comprising administration to the patient of a pharmaceutical composition comprising a pharmaceutically acceptable carrier and a nucleic acid sequence encoding an isolated cysteine-rich binding domain polypeptide derived from a *P. falciparum* 175 kDa sialic acid binding protein of SEQ ID NO:4, wherein the nucleic acid sequence encodes an amino acid sequence of about 50 to about 325 residues comprising cysteine residues that are in substantially similar relative positions as positions of cysteine residues in an amino acid sequence of a Duffy Antigen binding protein of *P. vivax* of SEQ ID NO:2.

18. The method of claim 17, wherein the patient is a human.

\* \* \* \* \*